(12) United States Patent
Nelson et al.

(10) Patent No.: US 7,560,250 B2
(45) Date of Patent: Jul. 14, 2009

(54) SOLUBLE FUSION PROTEINS COMPRISING HETEROLOGOUS POLYPEPTIDES

(75) Inventors: Nathan Nelson, Tel Aviv (IL); Anat Lavi, Tel Aviv (IL); Shani Leviatan, Mishmar HaSharon (IL)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 38 days.

(21) Appl. No.: 11/705,106

(22) Filed: Feb. 12, 2007

(65) Prior Publication Data
US 2007/0202573 A1 Aug. 30, 2007

Related U.S. Application Data

(63) Continuation-in-part of application No. PCT/IL2005/000874, filed on Aug. 11, 2005.

(60) Provisional application No. 60/600,363, filed on Aug. 11, 2004.

(51) Int. Cl.
C07K 19/00 (2006.01)
C12N 15/62 (2006.01)
C12N 15/70 (2006.01)
C12N 15/31 (2006.01)

(52) U.S. Cl. .................. 435/69.7; 530/350; 536/23.4
(58) Field of Classification Search .............. None
See application file for complete search history.

(56) References Cited

U.S. PATENT DOCUMENTS 6,207,420 B1    3/2001    Harrison et al.

OTHER PUBLICATIONS

Davis et al. "New Fusion Protein Systems Designed to Give Soluble Expression in *Escherichia coli*", Biotechnology and Bioengineering, 65(4): 382-388, 1999. Abstract, Table I.
Kapust et al. "*Escherichia coli* Maltose-Binding Protein Is Umcommonly Effective at Promoting the Solubility of Polypeptides to Which It Is Fused", Protein Science, Cambridge University Press, GB, 8(8): 1668-1674, 1999. Abstract, Table I, Fig.2.

*Primary Examiner*—John D Ulm

(57) ABSTRACT

A soluble fusion protein is disclosed. The soluble fusion protein comprises at least one soluble polypeptide and a heterologous polypeptide being fused thereto, the heterologous polypeptide being normally insoluble and/or suboptimally expressed when expressed in a cell, wherein the at least one soluble polypeptide has an amino acid sequence at least 65 percent similar to SEQ ID NO: 1 and/or 2, as determined using the Standard protein-protein BLAST [blastp] software of the NCBI.

46 Claims, 28 Drawing Sheets
(22 of 28 Drawing Sheet(s) Filed in Color)

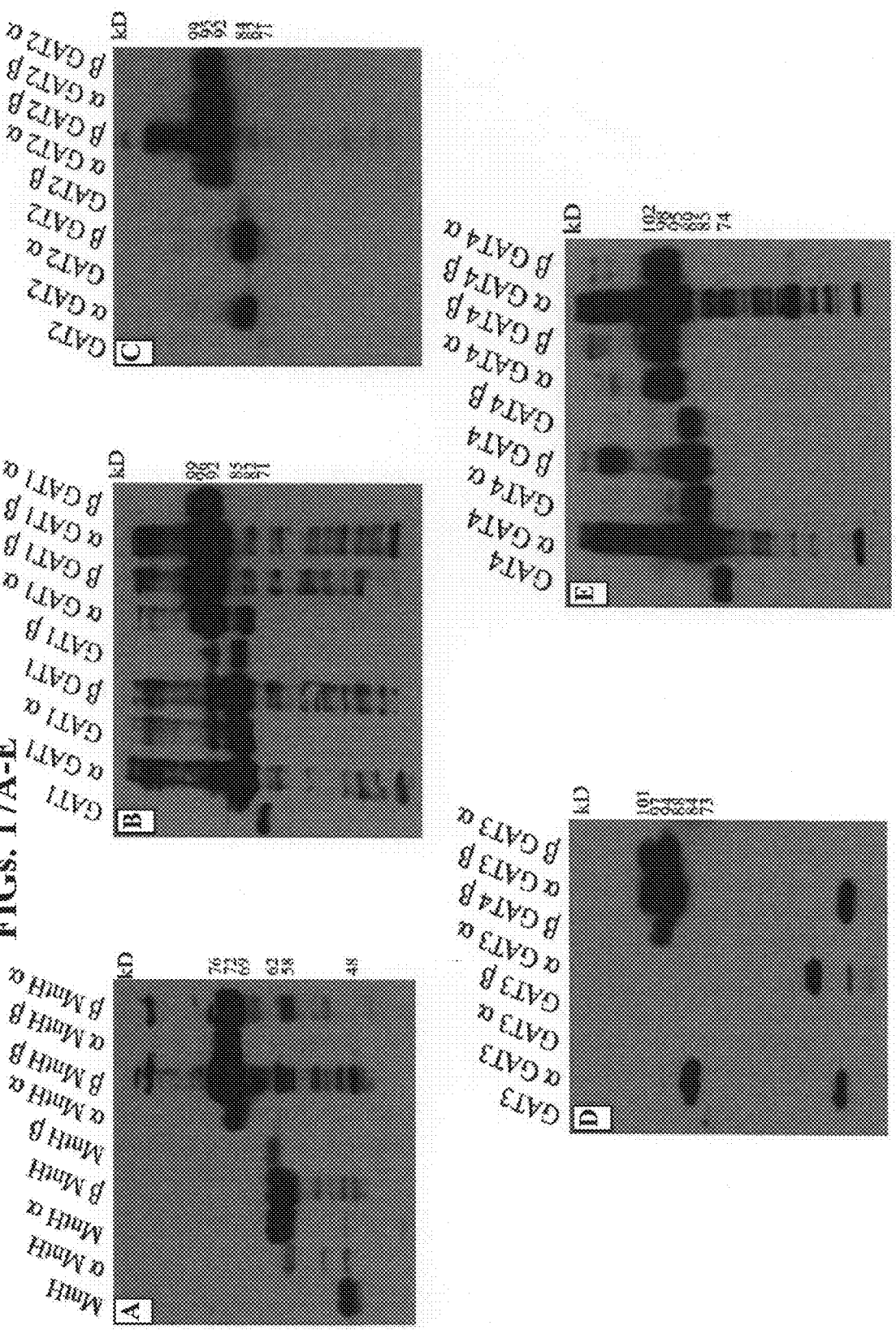
FIGs. 17A-E

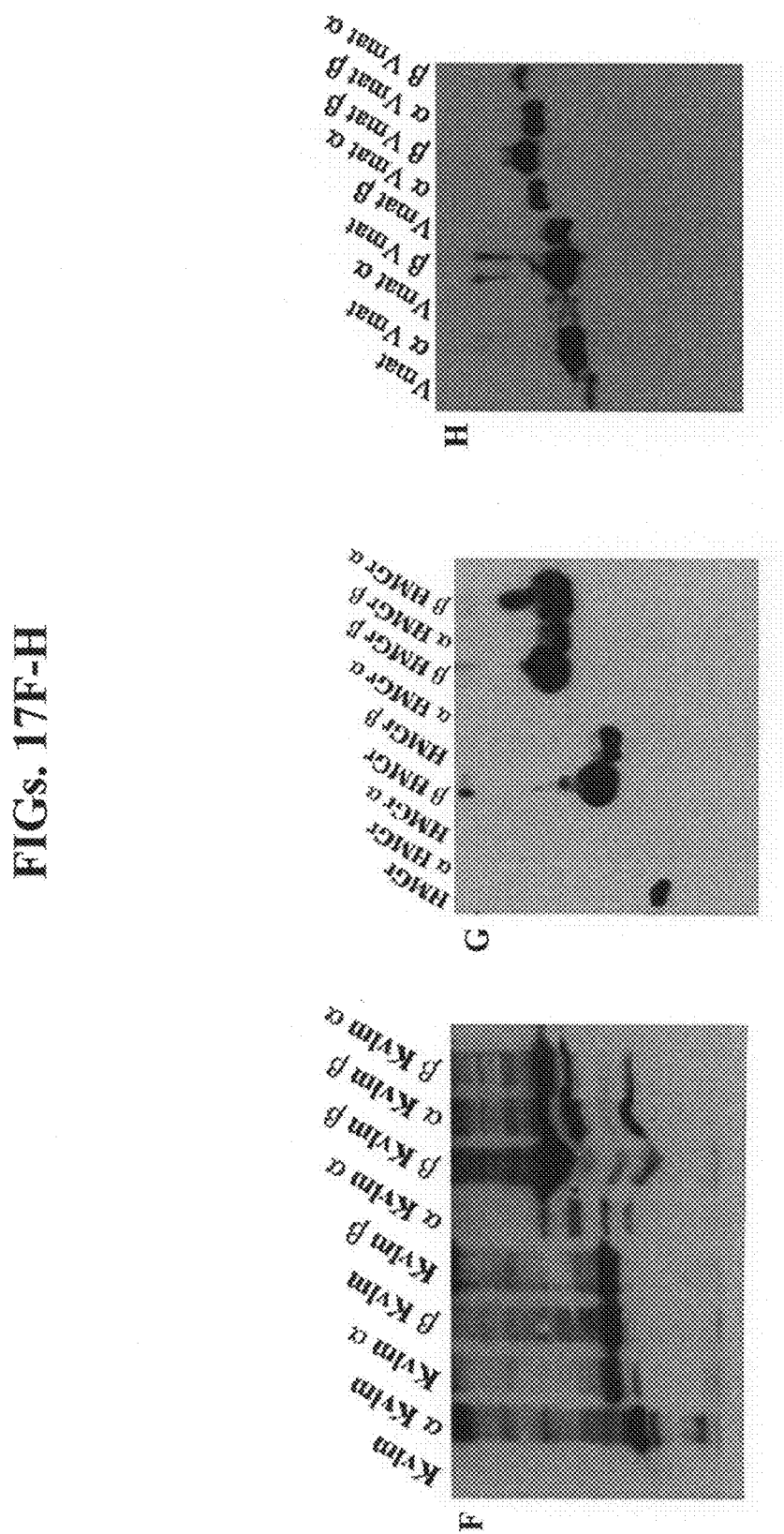
FIGs. 17F-H

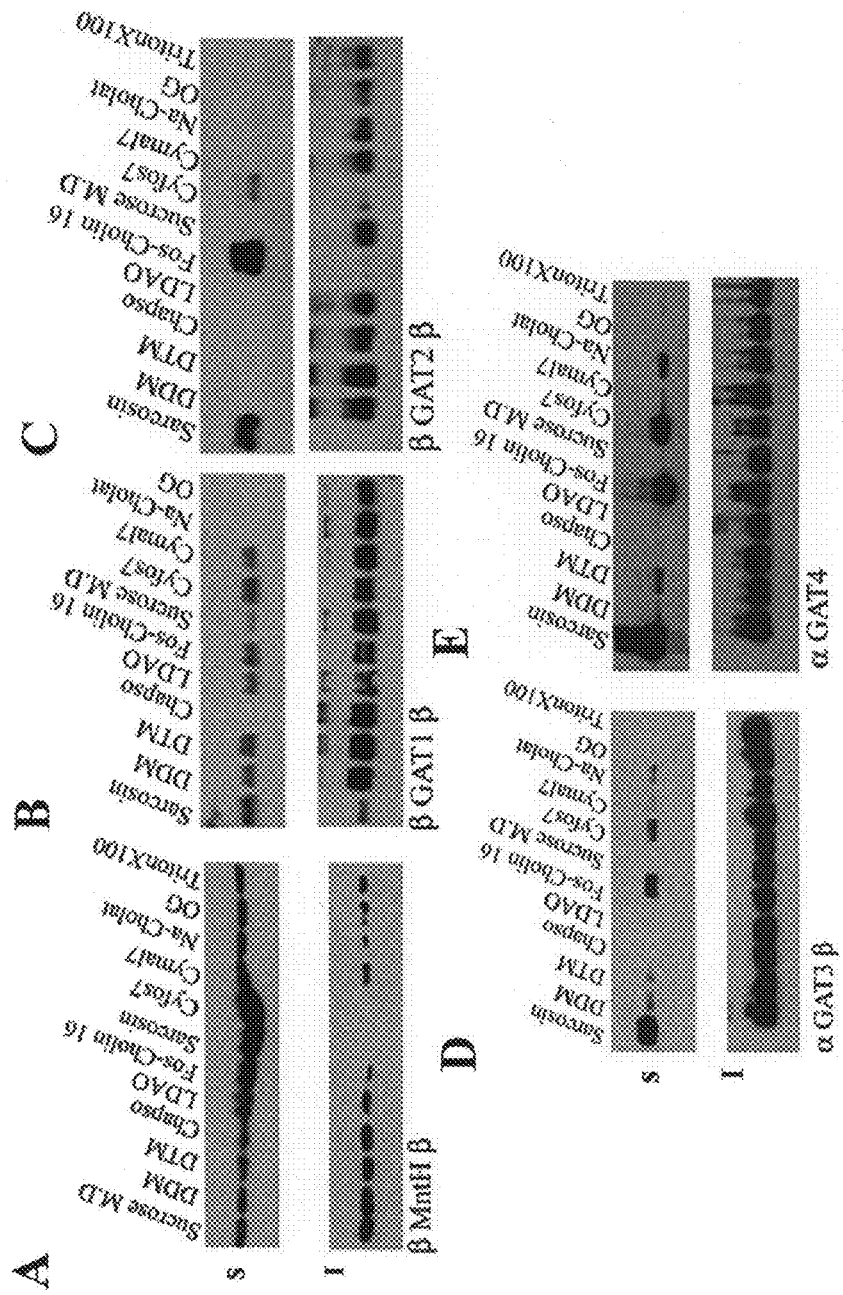
FIGs. 18A-E

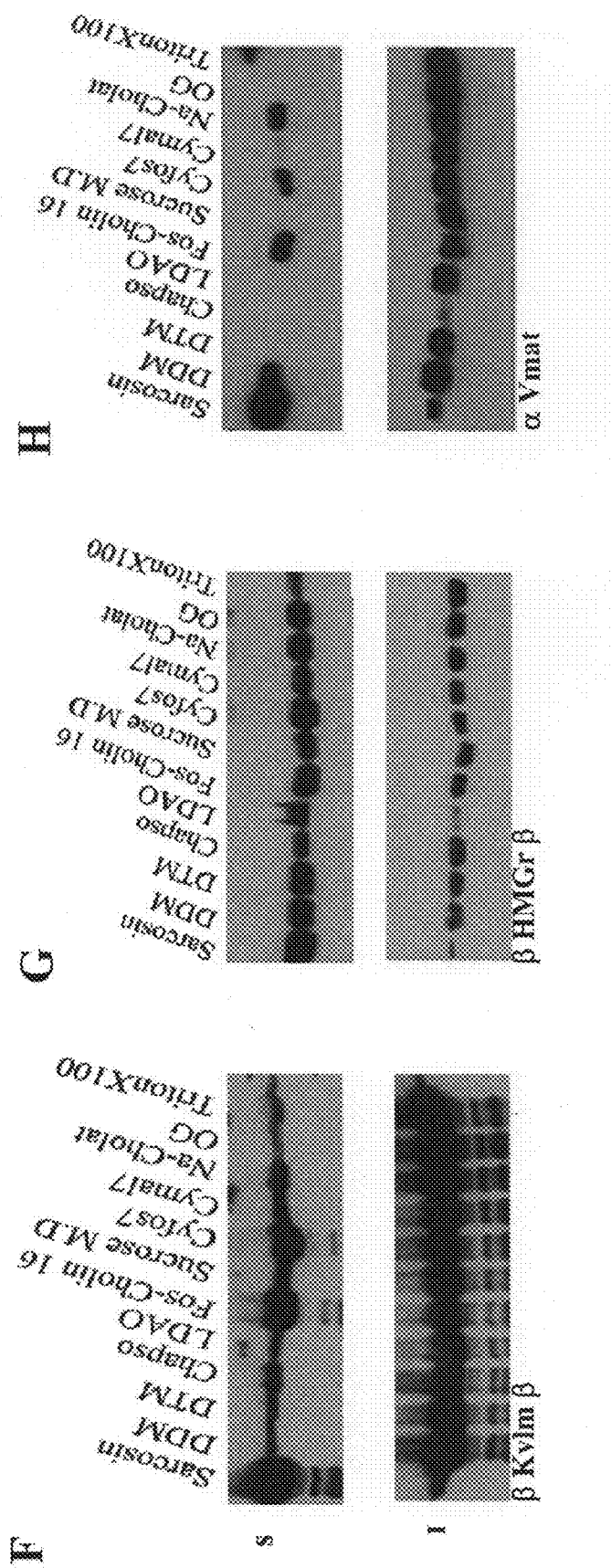
FIGs. 18F-H

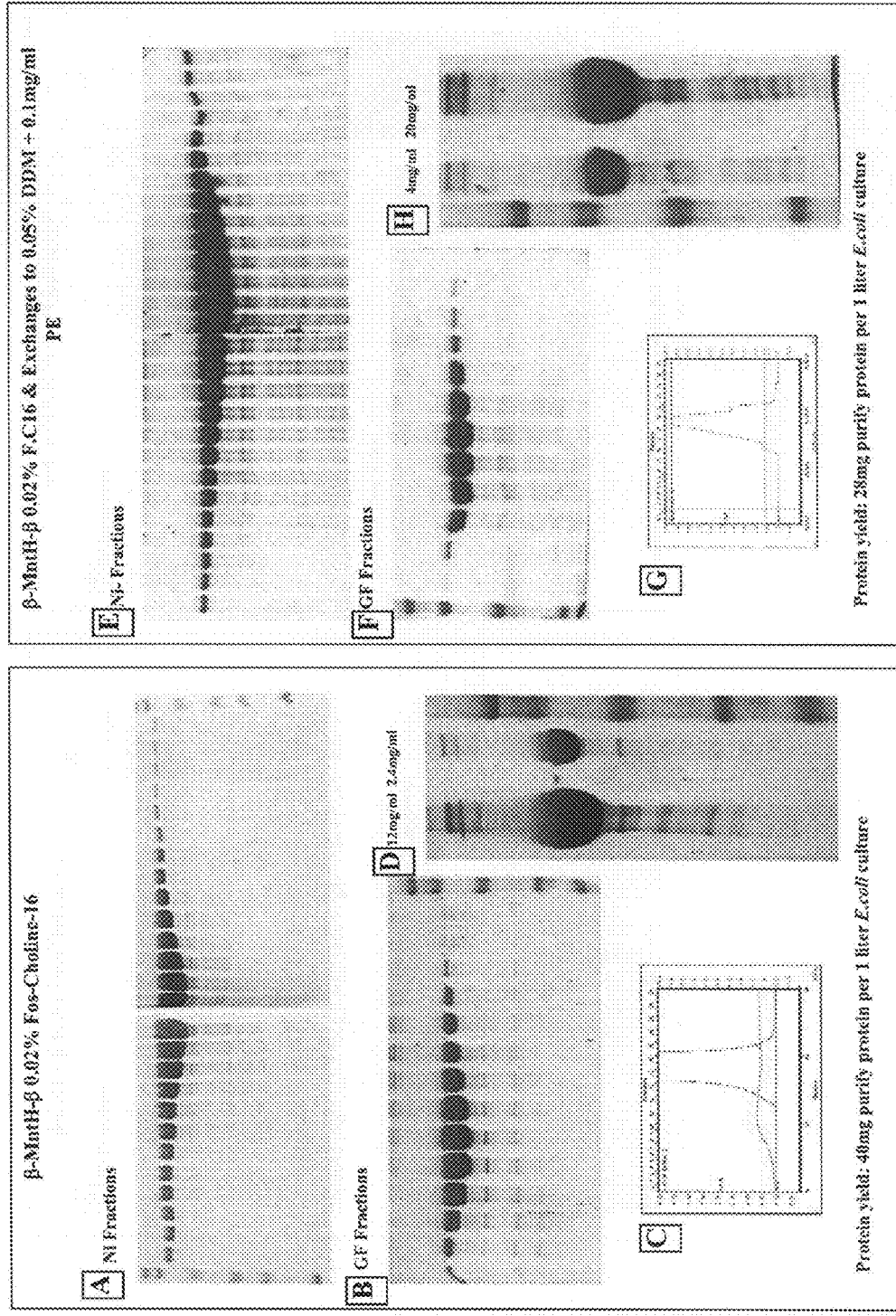
FIGs. 19A-H

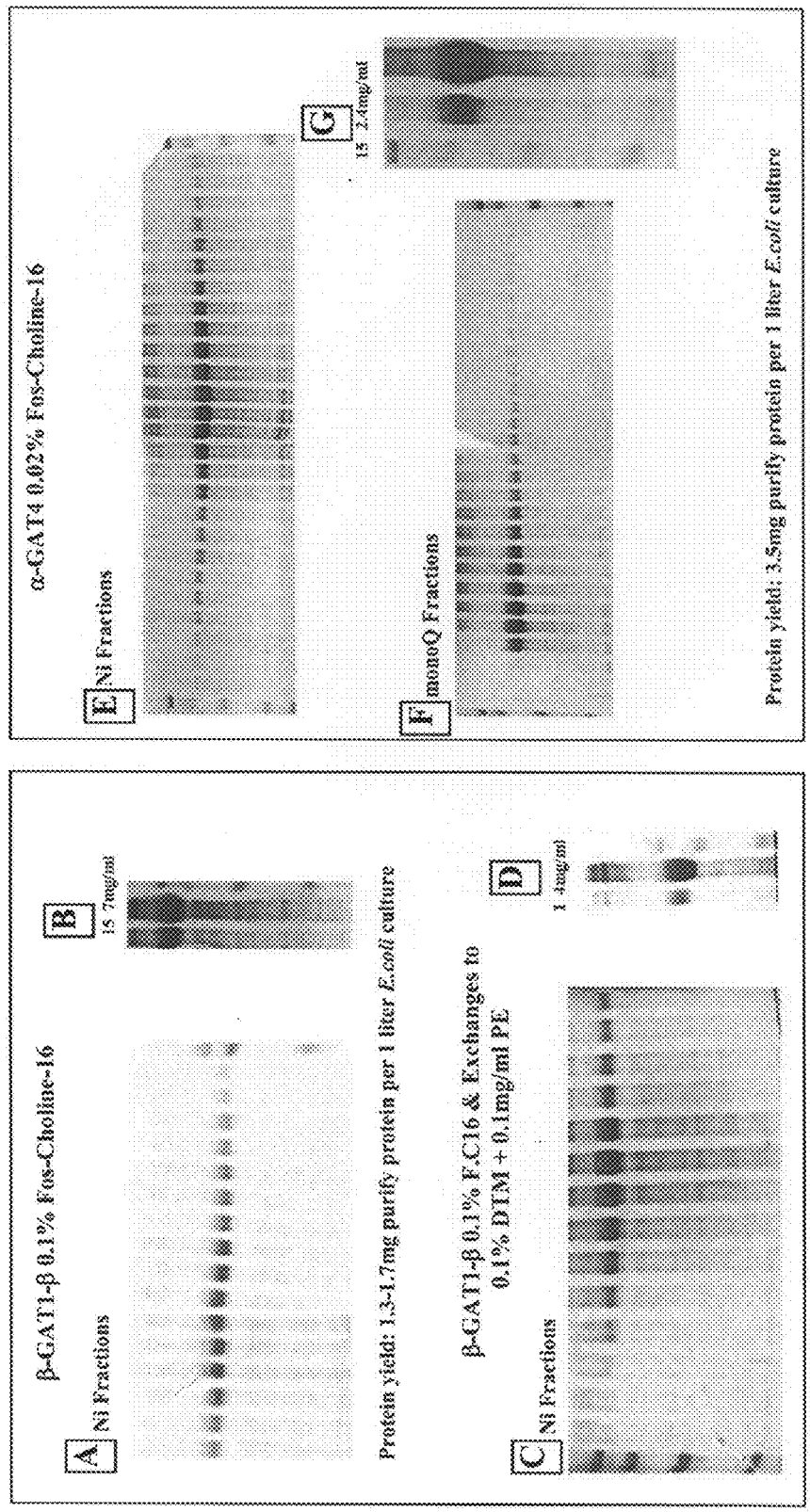
FIGs. 20A-G

FIGs. 21A-H
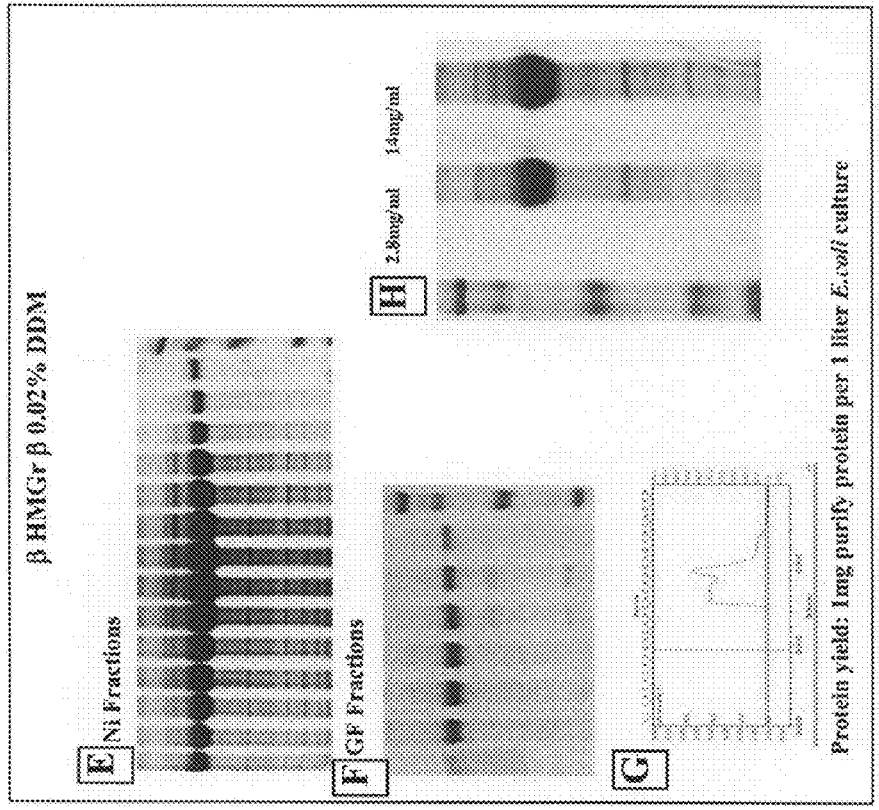
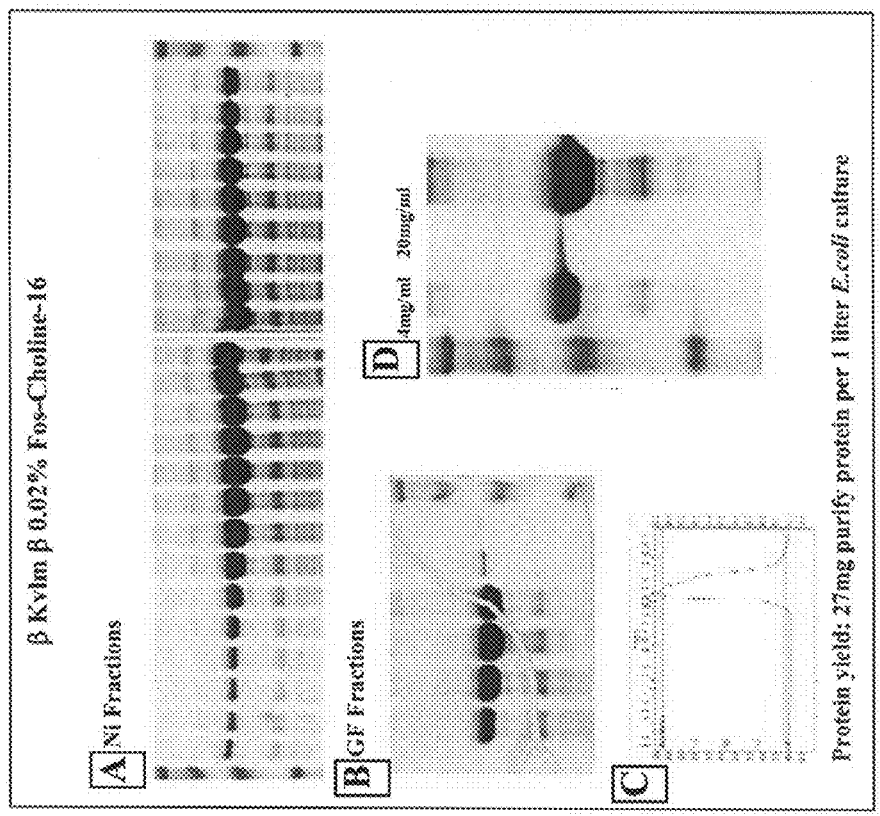

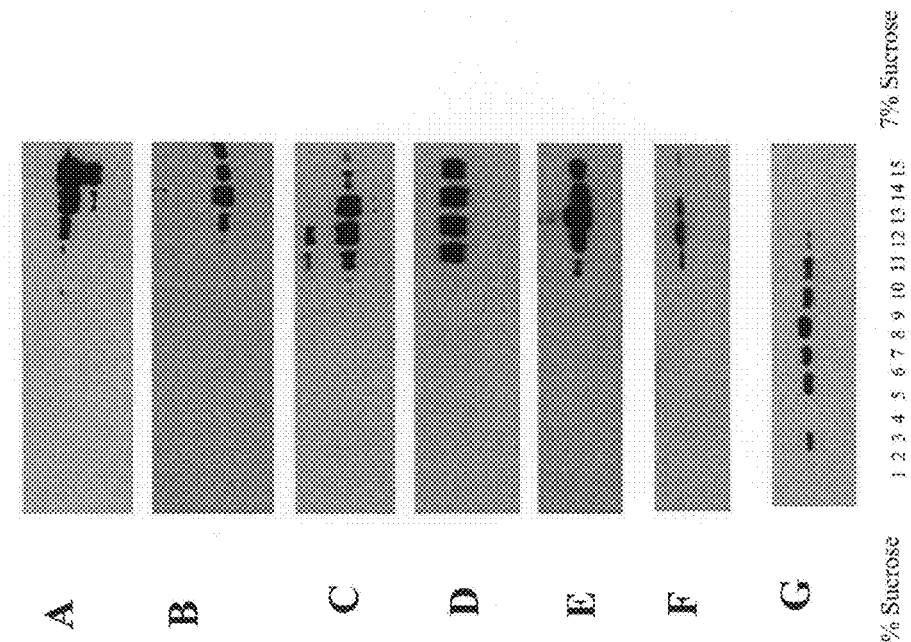
FIGs. 22A-G

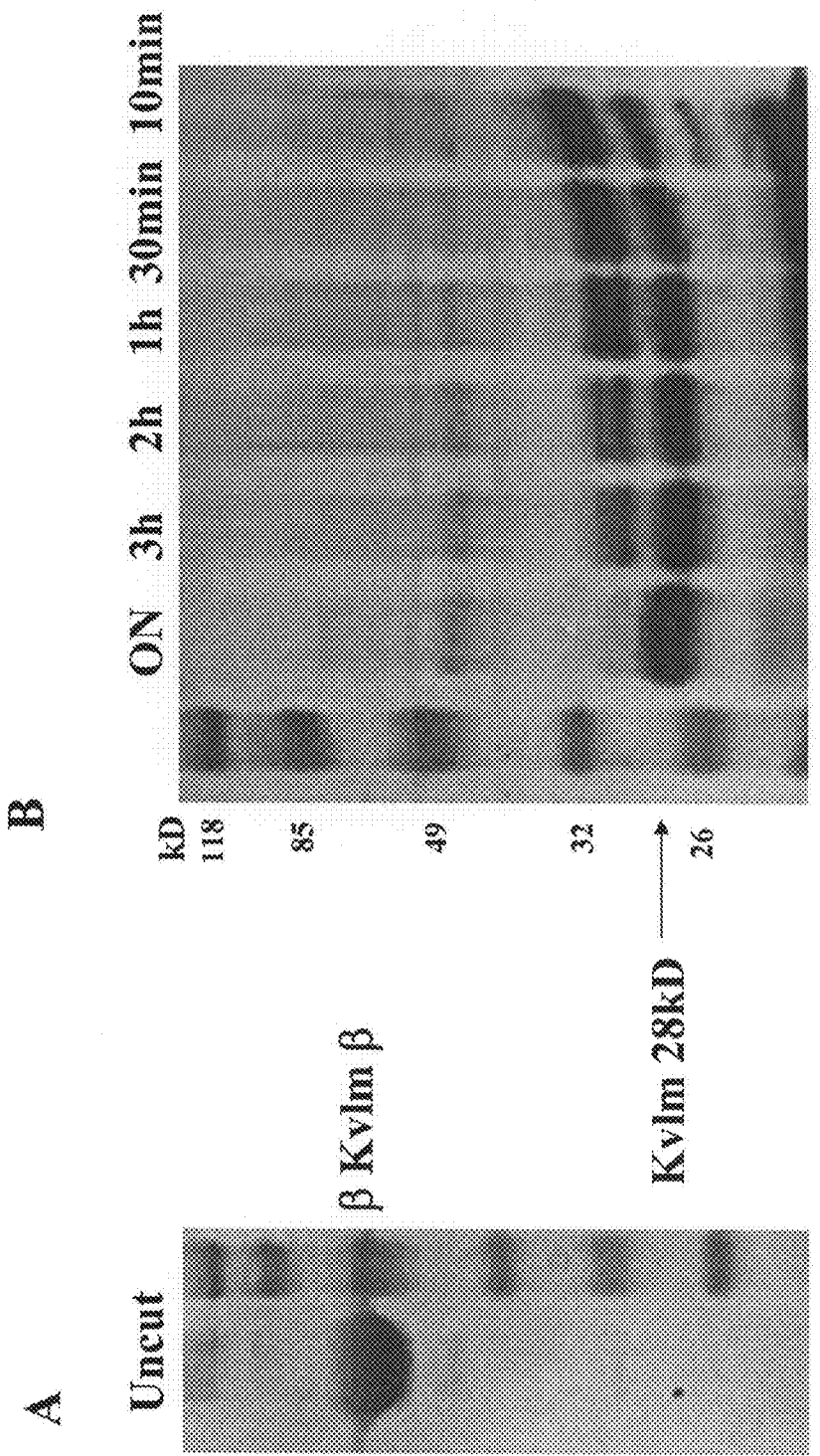
FIGs. 27A-B

SOLUBLE FUSION PROTEINS COMPRISING HETEROLOGOUS POLYPEPTIDES

RELATED APPLICATIONS

This Application is a Continuation-in-part of PCT Patent Application No. PCT/IL2005/000874, Filed on Aug. 11, 2005, which claims the benefit of U.S. Provisional Patent Application No. 60/600,363, Filed on Aug. 11, 2004. The above Applications are incorporated herein by reference

FIELD AND BACKGROUND OF THE INVENTION

The present invention relates to methods of producing in optimal quantities soluble fusion proteins which comprise a heterologous polypeptide which is normally insoluble and/or suboptimally expressed when expressed in a cell. More particularly, the present invention relates to soluble fusion proteins which comprise an optimally large heterologous polypeptide, such as a membrane protein, fused to an optimally small soluble carrier polypeptide, which can be expressed by recombinant host cells in amounts and with a solubility, purifiability and stability under crystallization conditions enabling their high-grade crystallization. The present invention further relates to polynucleotides encoding such fusion proteins, to expression vectors for expression of such fusion proteins, to cloning vectors for generating such expression vectors, to kits which comprise such cloning vectors, to host cells transformed with such polynucleotides/vectors, and to methods of generating such fusion proteins.

The capacity to produce polypeptides in a soluble form and quantity enabling their high-grade (highly ordered and homogeneous) crystallization enables solution of their 3D atomic structure via X-ray crystallography. Such crystallography is proving to be crucial for understanding and regulating the biological functions of polypeptides, and, as such, is playing an increasingly vital role in the advancement of biomedical science and biotechnology, in particular in the realm of drug design. For example, computationally assisted drug design/identification based on the solved X-ray crystallographic structures of key proteins involved in disease pathogenesis has been successfully used to design critical breakthrough drugs such as HIV-1 protease inhibitors for treating AIDS (Wlodawer A. and Vondrasek J., 1998. Annu Rev Biophys Biomol Struct. 27:249), tyrosine kinase inhibitors for treating leukemia (Wong S. and Witte ON., 2004. Annu Rev Immunol. 22:247306), and influenza virus neuraminidase inhibitors for treating influenza (Wilson J C. and von Itzstein M., 2003. Curr Drug Targets. 4:389-408). Further industrial applications of high-grade polypeptide crystals include their use as catalysts on a commercial scale, in bioremediation and green chemistry applications, purification-related applications, such as enantioselective chromatography of pharmaceuticals and high-grade chemicals, and development of adjuvant-less vaccines (Margolin A L. and Navia M A., 2001. Angewandte Chemie International Edition 40:2204).

Although polypeptide crystals are clearly tremendously and uniquely useful, their crystallization generally remains highly challenging, in particular in the case of heterologous polypeptides, such as membrane proteins, which are normally insoluble and/or suboptimally expressed when expressed in a cell. The difficulty in crystallizing membrane proteins and determining their 3D structures via X-ray diffraction is amply demonstrated by the fact that out of 28,000 high resolution protein structures solved to date, a mere 88 are of known membrane proteins. So far, only 4 heterologous recombinant mammalian membrane proteins have been crystallized and their 3D structure solved. These include mouse cyclooxygenase-2 overexpressed in a baculovirus/insect cell system (Kurumbail, R. G. et al., 1996. Nature 384:644-648); monoamine oxidase B, a mitochondrial membrane protein which includes alpha-helices anchored to the membrane in its carboxyl terminus, overexpressed in yeast (*Pichia pastoris*; Binda, C. et al., 2002. Nature Struct. Biol. 9:22-6); and fatty acid amide hydrolase (FAAH) expressed in *E. coli* (Bracey et al. 2002). Cyclooxygenase-2 and monoamine oxidase B are monotopic membranal proteins which cross only one section of the membrane lipid bilayer (monotopic proteins). The fourth heterologous mammalian membrane protein crystallized is the potassium channel-Kv1.2 which is a transmembrane protein. The channel was overexpressed in yeast *Pichia pastoris* (Long et at.2005).

In general, techniques for growing polypeptide crystals currently rely substantially on empirical processes for which only general rules of thumb are available and which frequently require adaptations tailored to accommodate the peculiarities of individual polypeptides. Several factors contribute to the difficulty in obtaining high-grade polypeptide crystals. Although contacts between crystallized polypeptide molecules are of comparable energy to those between small molecules, the significantly fewer number of intermolecular contacts per molecular weight of crystallized polypeptide molecules renders these contacts very fragile (Carugo O. and Argos P., 1997. Protein Science 6:2261). Furthermore, due to their inherent complexity, polypeptide molecules can assume numerous conformations, a phenomenon which tends to prevent formation of highly ordered crystals. Moreover, aggregated polypeptides are able to form many different types of intermolecular contacts of which only a restricted number will generate highly ordered crystals. Hence, crystallization conditions must be carefully fine-tuned so as to induce the proper molecular conformation and packing orientation of each molecule accreted during the process of crystallization. Such conditions are difficult to obtain since small variations in physico-chemical parameters, such as pH, ionic strength, temperature or contaminants, will strongly influence the process of crystallization in a way that is unique for each polypeptide due to the diversity of the chemical groups and possible configurations thereof involved in the formation of intermolecular contacts (Giege R. et al., Acta Crystallographica Section D-Biological Crystallography 1994. 50:339; Durbin S D. and Feher G., 1996. Annu Rev Phys Chem. 47:171; Weber P C., *Overview of protein crystallization methods*, in *Macromolecular Crystallography, Pt a*. 1997. p. 13-22; Chernov A A., Physics Reports-Review Section of Physics Letters 1997. 288:61; Rosenberger F., *Theoretical and Technological Aspects of Crystal Growth* 1998. p. 241; Wiencek J M., 1999. Annu Rev Biomed Eng. 1:505). Thus, a widely employed method for empirically determining conditions required for polypeptide crystal growth involves performing automated high-throughput crystallization assays (Morris, D W. et al., 1989. Biotechniques 7:522; Zuk W M. and Ward K B., 1991. Journal of Crystal Growth 110:148; Heinemann U. et al., 2000. Progress in Biophysics & Molecular Biology 73:347). Such high throughput methods employ the sparse-matrix protein crystallization method, in which a series of crystallization conditions are tested in parallel, the most promising ones being iteratively refined until crystallization is achieved (Jancarik J. and Kim S H., 1991. Journal of Applied Crystallography 24:409; Cudney B., et al., 1994. Acta Crystallographica Section D-Biological Crystallography 50:414; Hennessy D. et al., 2000. Acta Crystallographica Section D-Biological Crystallography 56:817). Thus, due to its empirical nature, this approach is inherently inefficient, time-consuming, and requires large amounts of pure polypeptides, which are expensive, and may be difficult or impossible to obtain.

The capacity to routinely produce polypeptides, such as membrane proteins, in a soluble form and quantity enabling their crystallization is highly desirable since membrane proteins nearly 30 percent of the proteins encoded by the eukaryotic genome, function as signal-transducing biological receptors, ion/metabolite channels/transporters, adhesion molecules, and the like, and as a consequence play a pivotal role in the maintenance of health, and in the pathogenesis of a vast range of diseases. For example, major diseases whose pathogenesis is associated with membrane protein functionality include viral diseases, cancer, cardiovascular diseases, neurodegenerative diseases, diabetes, cystic fibrosis, and multi-drug resistance. Accordingly, membrane proteins represent about 70 percent of all drug targets. Thus, high-grade membrane protein crystals could be used to generate vital 3D crystallography data with which to perform computationally assisted design/identification of optimally effective and specific pharmacological agents for treating such diseases. However, membrane protein crystallization is particularly difficult due to the fact that, unlike soluble polypeptides which tend to have hydrophilic surfaces and polar cores, thereby facilitating their expression in bacteria in a soluble form and quantity enabling their crystallization, membrane proteins include large hydrophobic surfaces with which they interact with membrane lipids, as well as hydrophilic portions. As a result, membrane proteins are not readily soluble in either polar or non-polar solvents, and are difficult to express in soluble form by transformed host bacteria, a process generally necessary to produce sufficient protein for crystallization, due to the tendency of such hydrophobic polypeptides to accumulate and overload at the cell membrane, which is also hydrophobic. Membrane proteins are inherently furthermore present at low abundance in the cell.

The capacity to produce proteins, such as membrane proteins, at high levels is highly desirable for numerous applications, including for production of drugs, diagnostic agents, immunogens and crystallization. An optimal means to obtain polypeptides is via recombinant expression in *E. coli*, due to high expression levels, the variety of plasmids and strains available for expression, the short time needed for cloning, and growth achievable in large quantities and at low cost. However, expression of membrane proteins in bacteria is difficult to achieve for the following reasons.

1. In order for the membrane protein to reach the membrane it must have specific signal sequences to be recognized by the bacterial translocon system. However, processing of overexpressed recombinant proteins overloads the translocon system at the expense of processing of vital endogenous proteins, resulting in host cell death. In most cases, alternate systems target the recombinantly expressed membrane protein to the bacterial membrane, leading to overloading of the bacterial membrane with recombinant membrane protein, and concomitantly resulting in host cell death as well.

2. Elements in the 3' or 5' region of the eukaryotic gene can destabilize mRNA leading to low expression levels.

3. Codon usage of prokaryotes is different from that of eukaryotes thus preventing adequate translation or even stopping it completely.

4. Various membrane proteins require interactions with chaperones or other proteins which are not available in the bacteria, leading to misfolded/degraded heterologous protein.

5. Bacteria are rich in proteases which cleave foreign proteins.

6. Bacteria cannot perform posttranslational modifications such as glycosylation and phosphorylation, having a vital role in the activity folding, stability and proper membranal anchoring of the protein (Grisshammer, R. and Tate, C. G., 1995. Quar. Rev. Biophys. 28: 315).

7. The lipid composition of prokaryotic membranes is significantly different from that of eukaryotic membranes and may be an inadequate environment for uptake of heterologous membrane proteins.

8. Bacteria tend to incorporate overexpressed proteins in insoluble inclusion bodies (Grisshammer, R. and Tate, C. G., 1995. Quar. Rev. Biophys. 28: 315).

Some of the problems related to the differences between eukaryotic and prokaryotic translation systems are partially answered by the new strain of *E. coli* (C43). This strain has several mutations in different proteases and a stable membrane. It can grow and be induced to express heterologous proteins at 18 degrees centigrade, thereby enhancing protein translation and stability upon exit from the ribosome (Miroux and Walker, 1996. J. Mol. Biol. 260: 289-298). Problems related to quality of expressed proteins and expression in inclusion bodies (or insoluble aggregates) have not yet been resolved. There are several examples of expression of eukaryotic proteins in active form in the *E. coli* system, namely mouse multi-drug resistance-1 protein; Bibi et al., 1993. Proc. Natl. Acad. Sci. 90: 9209-9213), erythrocyte glucose transporter (Sarkar, H. K. et al., 1988. Proc. Nat. Acad. Sci. 85: 5463-5467), glutamate mitochondrial transporter from human (Firemonte et al. 2002) and Arabidopsis ethylene response receptor (Voet-van-Vormizeele, J. and Groth, G., 2003. Protein. Expr. Purif. 32:89-94).

One potentially optimal strategy which has been proposed for obtaining heterologous polypeptides, such as membrane proteins, which are normally insoluble and/or suboptimally expressed when expressed in a cell, in a soluble and purifiable, and hence crystallizable, form involves complexing or fusing such polypeptides with carrier molecules so as to generate complexes/conjugates having such desired properties.

Various prior art approaches have been attempted for obtaining heterologous polypeptides which are normally insoluble and/or suboptimally expressed when expressed in a cell, in a soluble and purifiable, and hence crystallizable, form by combining these with carrier molecules so as to generate complexes/conjugates having the desired characteristics.

One approach involves the use of detergents which interact with the hydrophobic surfaces of the membrane protein in an attempt to generate soluble/crystallizable mixed detergent: protein micelles, and crystallizing such micelles as a two-dimensional (2D) lattice by reconstitution in an artificial lipid bilayer, allowing 2D structural determination via electron microscopy. While such 2D crystals have been obtained, the use of electron microscopy for determining molecular structure has the significant drawback of generating structural information with poor resolution in directions orthogonal to the 2D lattice, thus preventing structural determination at high resolution (Stowell M H. et al., 1998. Curr Opin Struct Biol. 8:595). An additional factor contributing to the difficulty of determining the structure of detergent-associated membrane proteins at high resolution is due to the fact that crystal contacts made between detergent micelles tend to be disordered, resulting in poorly diffracting crystals. Although the use of helical crystals and advanced image processing can obviate some of these drawbacks, it is only with X-ray crystallography of 3D crystals that high resolution determination of 3D protein structure can be achieved. This is essential, for example, to generate detailed pictures of molecular target sites when designing drugs specifically interacting with such sites.

Various prior art approaches involve joining an insoluble heterologous polypeptide to a lipid carrier molecule in an attempt to generate a crystallizable composition.

One carrier lipid-based approach involves binding of an insoluble heterologous polypeptides to divalent metal ion-chelated lipids or electrostatically charged lipids via specific surface histidine residues or via complementarily charged residues, respectively. While planar layers of such lipids have been employed to generate 2D protein crystals (Frey W. et al., 1996. Proc. Natl. Acad. Sci. U. S. A. 93:4937), such crystals can only be analyzed by electron microscopy, as opposed to X-ray diffraction, and consequently can only be used to generate crystallographic structure data of limited resolution and dimensionality.

Another carrier lipid-based approach involves using lipid nanotubes to generate helical crystals of membrane proteins (Wilson-Kubalek, E. et al., Proc. Natl. Acad. Sci. U. S. A. 1998, 95:8040). These crystals, however, can only be used to determine 3D protein structure at low resolution using electron microscopy and thus cannot be employed to solve molecular structure at atomic resolution, as is the case with X-ray crystallography.

A further approach involves complexing membrane proteins with antibody fragments in an attempt to generate complexes having enhanced solubility, and hence crystallizability, and improved capacity to form crystal contacts relative to the non-complexed membrane proteins (Hunte, C. and Michel, H., 2002. Curr Opin Struct Biol. 12: 503-508; Hunte C., 2001. FEBS Lett. 504:126-32; Lange C. and Hunte C., 2002. Proc Natl Acad Sci U S A. 99:2800-5; Ostermeier C. and Michel H., 1997. Curr Opin Struct Biol. 7:697; Ostermeier C. et al., 1997. Proc Natl Acad Sci U S A. 94:10547-53). This approach, however, is expensive and impractically complex, time-consuming and inefficient since it must be specifically tailored for each individual membrane protein, in particular due to the need to employ antibodies having different specificities for each individual membrane protein.

Yet a further approach involves expressing a fusion protein which comprises the E. coli-derived carrier protein NusA (495 amino acid residue length), GrpE, or bacterioferritin fused to an in soluble heterologous polypeptide which is normally produced in the form of inclusion bodies (Davis, G. D. et al., 1999. Biotechnol. Bioeng. 65: 382-388). Such an approach, however, employs excessively large carrier proteins, and fails to demonstrate optimally broad applicability with respect to diverse heterologous polypeptides.

An additional approach involves expressing a fusion protein which comprises the E. coli-derived carrier protein maltose binding protein (MBP, 370 amino acid residue length), glutathione S-transferase (GST), or thioredoxin fused to a heterologous polypeptide which is normally insoluble and/or suboptimally expressed when expressed in a cell (Kapust, R. B., Waugh, D. S., 1999. Protein Sci. 8:1668-1674). Such an approach, however, has the critical disadvantage of employing carrier proteins which are excessively large and/or suboptimally effective for generating fusion proteins which are soluble.

Still a further approach involves expressing a fusion protein which comprises a heterologous polypeptide translationally fused to an E. coli carrier protein conferring upon the fusion protein enhanced expressibility in soluble/crystallizable form by bacterial host cells relative to the native heterologous polypeptide (U.S. Pat. Nos. 6,207,420 and 5,989,868). Such an approach is associated with various critical disadvantages, however. Namely, such an approach is furthermore only applicable to facilitating solubilization/production of very small polypeptides, since the largest polypeptide of interest demonstrably expressed fused to a carrier polypeptide by this approach has a molecular weight of only 21.6 kilodaltons. Additionally, such an approach has the critical drawback of employing a carrier polypeptide having a molecular weight which is at least as high as that of the heterologous polypeptide.

Yet still a further approach involves expressing a fusion protein which comprises the heterologous polypeptide bovine cytochrome b5 (134 amino acid length; 16.5 kilodaltons) fused to the carrier polypeptide E. coli thioredoxin (109 amino acid residue length, 12 kilodaltons; Begum, R. R. et al., 2000. J. Chromatogr. B Biomed. Sci. Appl. 737:119-30). Such an approach, however has the critical disadvantages of employing a carrier polypeptide which is at least approximately three-quarters the size of the heterologous polypeptide, and is only applicable to facilitating solubilization/production of very small polypeptides, since the largest polypeptide of interest demonstrably expressed fused to a carrier polypeptide by this approach has a molecular weight of only 16.5 kilodaltons. Furthermore, this approach has failed to demonstrate general applicability with respect to diverse heterologous polypeptides.

Prior art soluble fusion proteins which are formed using carrier polypeptides which have a molecular weight which is at least approximately three-quarters that of the heterologous polypeptide to which they are fused will tend to distort the native conformation of the heterologous polypeptide to an excessively large extent via correspondingly large steric and electrostatic effects. This is highly undesirable since this will prevent generation of fusion protein crystals capable of generating crystallographic data defining the native 3D atomic structure of membrane proteins with optimal accuracy. Furthermore, the excessively large size of the carrier polypeptide inherently results in inefficient production yields of the heterologous polypeptide. The excessive conformational distortion of the heterologous polypeptide is furthermore highly undesirable for its use, in the form of the fusion protein, as a therapeutic/diagnostic reagent, or as an immunogen for raising antibodies specific for native conformational epitopes thereof. Critically, such an approach additionally fails to demonstrate general applicability with respect to a significantly diverse range of heterologous polypeptides.

Thus, the prior art fails to provide a generally applicable method of producing, in a satisfactorily/optimally soluble, purifiable, and crystallizable form, heterologous polypeptides, such as membrane proteins, which are normally insoluble and/or suboptimally expressed when expressed in a cell.

There is thus a widely recognized need for, and it would be highly advantageous to have, a method devoid of the above limitation.

SUMMARY OF THE INVENTION

The present invention discloses the use of novel soluble carrier proteins for generation of soluble fusion proteins which comprise a heterologous polypeptide which is normally insoluble and/or suboptimally expressed when expressed in a cell. This use can be effected in a variety of ways as further described and exemplified hereinbelow.

According to one aspect of the present invention there is provided a method of producing a soluble fusion protein which comprises a heterologous polypeptide, the heterologous polypeptide being normally insoluble and/or suboptimally expressed when expressed in a cell, the method comprising:

culturing a host cell being transfected or transformed with a recombinant polynucleotide encoding a fusion protein which comprises at least one soluble polypeptide and the heterologous polypeptide being fused thereto, the culturing being under conditions causing expression of the polynucleotide in the host cell, wherein the at least one soluble polypeptide has an amino acid sequence at least 65 percent similar to SEQ ID NO: 1 and/or 2, as determined using the Standard protein-protein BLAST [blastp] software of the NCBI; and optionally, isolating the fusion protein which comprises the at least one soluble polypeptide and the heterologous polypeptide being fused thereto from the host cell following the culturing, thereby producing the soluble fusion protein.

According to one aspect of the present invention there is provided a method of producing a soluble fusion protein which comprises a heterologous polypeptide, the heterologous polypeptide being normally insoluble and/or suboptimally expressed when expressed in a cell, the method comprising:

culturing a host cell being transfected or transformed with a recombinant polynucleotide encoding a fusion protein which comprises at least one soluble polypeptide and the heterologous polypeptide being fused thereto, the culturing being under conditions causing expression of the polynucleotide in the host cell, wherein the at least one soluble polypeptide comprises at least 2 alpha-helical structures being separated therebetween by at least one polypeptide loop, and is composed of a number of amino acid residues selected from a range of about 121 to about 91 or less amino acid residues; and optionally, isolating the fusion protein which comprises the at least one soluble polypeptide and the heterologous polypeptide being fused thereto from the host cell following the culturing, thereby producing the soluble fusion protein.

According to one aspect of the present invention there is provided a method of producing a soluble fusion protein which comprises a heterologous polypeptide, the heterologous polypeptide being normally insoluble and/or suboptimally expressed when expressed in a cell, the method comprising:

culturing a host cell being transfected or transformed with a recombinant polynucleotide encoding a fusion protein which comprises at least one soluble polypeptide and the heterologous polypeptide being fused thereto, the culturing being under conditions causing expression of the polynucleotide in the host cell, wherein the at least one soluble polypeptide has a molecular weight which is at least 1.5 times lower than a molecular weight of the heterologous polypeptide; and optionally, isolating the fusion protein which comprises the at least one soluble polypeptide and the heterologous polypeptide being fused thereto from the host cell following the culturing, thereby producing the soluble fusion protein.

According to still another aspect of the present invention there is provided a recombinant polynucleotide encoding a soluble fusion protein which comprises at least one soluble polypeptide and a heterologous polypeptide being fused thereto, wherein the heterologous polypeptide is normally insoluble and/or suboptimally expressed when expressed in a cell, the recombinant polynucleotide comprising:

at least one first polynucleotide encoding the at least one soluble polypeptide; and a second polynucleotide encoding the heterologous polypeptide, the at least one first polynucleotide and the second polynucleotide being positioned in frame with respect to each other so as to encode the soluble fusion protein, wherein the at least one soluble polypeptide has an amino acid sequence at least 65 percent similar to SEQ ID NO: 1 and/or 2, as determined using the Standard protein-protein BLAST [blastp] software of the NCBI.

According to a further aspect of the present invention there is provided a recombinant polynucleotide encoding a soluble fusion protein which comprises at least one soluble polypeptide and a heterologous polypeptide being fused thereto, wherein the heterologous polypeptide is normally insoluble and/or suboptimally expressed when expressed in a cell, the recombinant polynucleotide comprising:

at least one first polynucleotide encoding the at least one soluble polypeptide; and a second polynucleotide encoding the heterologous polypeptide, the at least one first polynucleotide and the second polynucleotide being positioned in frame with respect to each other so as to encode the soluble fusion protein, wherein the at least one soluble polypeptide comprises at least 2 alpha-helical structures being separated therebetween by at least one polypeptide loop, and is composed of a number of amino acid residues selected from a range of about 121 to about 91 or less amino acid residues.

According to yet a further aspect of the present invention there is provided a recombinant polynucleotide encoding a soluble fusion protein which comprises at least one soluble polypeptide and a heterologous polypeptide being fused thereto, wherein the heterologous polypeptide is normally insoluble and/or suboptimally expressed when expressed in a cell, the recombinant polynucleotide comprising:

at least one first polynucleotide encoding the at least one soluble polypeptide; and a second polynucleotide encoding the heterologous polypeptide, the at least one first polynucleotide and the second polynucleotide being positioned in frame with respect to each other so as to encode the soluble fusion protein, wherein the at least one soluble polypeptide has a molecular weight which is at least 1.5 times lower than a molecular weight of the heterologous polypeptide.

According to still a further aspect of the present invention there is provided an expression vector comprising the recombinant polynucleotide encoding a soluble fusion protein which comprises at least one soluble polypeptide and a heterologous polypeptide being fused thereto, wherein the heterologous polypeptide is normally insoluble and/or suboptimally expressed when expressed in a cell, the recombinant polynucleotide comprising:

at least one first polynucleotide encoding the at least one soluble polypeptide; and a second polynucleotide encoding the heterologous polypeptide, the at least one first polynucleotide and the second polynucleotide being positioned in frame with respect to each other so as to encode the soluble fusion protein, wherein the at least one soluble polypeptide has an amino acid sequence at least 65 percent similar to SEQ ID NO: 1 and/or 2, as determined using the Standard protein-protein BLAST [blastp] software of the NCBI, and wherein the recombinant polynucleotide further comprises at least one expression control sequence being operatively linked thereto and capable of controlling expression thereof in a host cell.

According to an additional aspect of the present invention there is provided an expression vector comprising the recombinant polynucleotide encoding a soluble fusion protein which comprises at least one soluble polypeptide and a heterologous polypeptide being fused thereto, wherein the heterologous polypeptide is normally insoluble and/or suboptimally expressed when expressed in a cell, the recombinant polynucleotide comprising:

at least one first polynucleotide encoding the at least one soluble polypeptide; and a second polynucleotide encoding the heterologous polypeptide, the at least one first polynucleotide and the second polynucleotide being positioned in frame with respect to each other so as to encode the soluble fusion protein, wherein the at least one soluble polypeptide has an amino acid sequence at least 65 percent similar to SEQ ID NO: 1 and/or 2, as determined using the Standard protein-protein BLAST [blastp] software of the NCBI, and wherein the recombinant polynucleotide further comprises at least one expression control sequence being operatively linked thereto and capable of controlling expression thereof in a host cell.

According to yet an additional aspect of the present invention there is provided an expression vector comprising the recombinant polynucleotide encoding a soluble fusion protein which comprises at least one soluble polypeptide and a heterologous polypeptide being fused thereto, wherein the heterologous polypeptide is normally insoluble and/or suboptimally expressed when expressed in a cell, the recombinant polynucleotide comprising:

at least one first polynucleotide encoding the at least one soluble polypeptide; and a second polynucleotide encoding the heterologous polypeptide, the at least one first polynucleotide and the second polynucleotide being positioned in frame with respect to each other so as to encode the soluble fusion protein, wherein the at least one soluble polypeptide has a molecular weight which is at least 1.5 times lower than a molecular weight of the heterologous polypeptide, and wherein the recombinant polynucleotide further comprises at least one expression control sequence being operatively linked thereto and capable of controlling expression thereof in a host cell.

According to still an additional aspect of the present invention there is provided a host cell transfected or transformed with the recombinant polynucleotide of encoding a soluble fusion protein which comprises at least one soluble polypeptide and a heterologous polypeptide being fused thereto, wherein the heterologous polypeptide is normally insoluble and/or suboptimally expressed when expressed in a cell, the recombinant polynucleotide comprising:

at least one first polynucleotide encoding the at least one soluble polypeptide; and a second polynucleotide encoding the heterologous polypeptide, the at least one first polynucleotide and the second polynucleotide being positioned in frame with respect to each other so as to encode the soluble fusion protein, wherein the at least one soluble polypeptide has an amino acid sequence at least 65 percent similar to SEQ ID NO: 1 and/or 2, as determined using the Standard protein-protein BLAST [blastp] software of the NCBI.

According to yet still an additional aspect of the present invention there is provided a host cell transfected or transformed with the recombinant polynucleotide encoding a soluble fusion protein which comprises at least one soluble polypeptide and a heterologous polypeptide being fused thereto, wherein the heterologous polypeptide is normally insoluble and/or suboptimally expressed when expressed in a cell, the recombinant polynucleotide comprising:

at least one first polynucleotide encoding the at least one soluble polypeptide; and a second polynucleotide encoding the heterologous polypeptide, the at least one first polynucleotide and the second polynucleotide being positioned in frame with respect to each other so as to encode the soluble fusion protein, wherein the at least one soluble polypeptide has an amino acid sequence at least 65 percent similar to SEQ ID NO: 1 and/or 2, as determined using the Standard protein-protein BLAST [blastp] software of the NCBI.

According to another aspect of the present invention there is provided a host cell transfected or transformed with the recombinant polynucleotide encoding a soluble fusion protein which comprises at least one soluble polypeptide and a heterologous polypeptide being fused thereto, wherein the heterologous polypeptide is normally insoluble and/or suboptimally expressed when expressed in a cell, the recombinant polynucleotide comprising:

at least one first polynucleotide encoding the at least one soluble polypeptide; and a second polynucleotide encoding the heterologous polypeptide, the at least one first polynucleotide and the second polynucleotide being positioned in frame with respect to each other so as to encode the soluble fusion protein, wherein the at least one soluble polypeptide has a molecular weight which is at least 1.5 times lower than a molecular weight of the heterologous polypeptide.

According to yet another aspect of the present invention there is provided a cloning vector comprising a cloning site and at least one first polynucleotide, the at least one first polynucleotide encoding at least one soluble polypeptide, the cloning site being designed to enable cloning of a second polynucleotide encoding a heterologous polypeptide in frame with respect to the at least one first polynucleotide so as to form a recombinant polynucleotide encoding a fusion protein which comprises the at least one soluble polypeptide and the heterologous polypeptide being fused thereto, wherein the at least one soluble polypeptide has an amino acid sequence at least 65 percent similar to SEQ ID NO: 1 and/or 2, as determined using the Standard protein-protein BLAST [blastp] software of the NCBI.

According to still another aspect of the present invention there is provided a cloning vector comprising a cloning site and at least one first polynucleotide, the at least one first polynucleotide encoding at least one soluble polypeptide, the cloning site being designed to enable cloning of a second polynucleotide encoding a heterologous polypeptide in frame with respect to the at least one first polynucleotide so as to form a recombinant polynucleotide encoding a fusion protein which comprises the at least one soluble polypeptide and the heterologous polypeptide being fused thereto, wherein the at least one soluble polypeptide comprises at least 2 alpha-helical structures being separated therebetween by at least one polypeptide loop, and is composed of a number of amino acid residues selected from a range of about 121 to about 91 or less amino acid residues.

According to a further aspect of the present invention there is provided a host cell transfected or transformed with the cloning vector comprising a cloning site and at least one first polynucleotide, the at least one first polynucleotide encoding at least one soluble polypeptide, the cloning site being designed to enable cloning of a second polynucleotide encoding a heterologous polypeptide in frame with respect to the at least one first polynucleotide so as to form a recombinant polynucleotide encoding a fusion protein which comprises the at least one soluble polypeptide and the heterologous polypeptide being fused thereto, wherein the at least one soluble polypeptide has an amino acid sequence at least 65 percent similar to SEQ ID NO: 1 and/or 2, as determined using the Standard protein-protein BLAST [blastp] software of the NCBI.

According to yet a further aspect of the present invention there is provided a host cell transfected or transformed with the cloning vector comprising a cloning site and at least one first polynucleotide, the at least one first polynucleotide encoding at least one soluble polypeptide, the cloning site being designed to enable cloning of a second polynucleotide encoding a heterologous polypeptide in frame with respect to the at least one first polynucleotide so as to form a recombinant polynucleotide encoding a fusion protein which comprises the at least one soluble polypeptide and the heterologous polypeptide being fused thereto, According to further features in preferred embodiments of the invention described below, the at least one soluble polypeptide comprises at least 2 alpha-helical structures being separated therebetween by at least one polypeptide loop, and is composed of a number of amino acid residues selected from a range of about 121 to about 91 or less amino acid residues.

According to still a further aspect of the present invention there is provided a soluble fusion protein comprising at least one soluble polypeptide and a heterologous polypeptide being fused thereto, the heterologous polypeptide being normally insoluble and/or suboptimally expressed when expressed in a cell, wherein the at least one soluble polypeptide has an amino acid sequence at least 65 percent similar to SEQ ID NO: 1 and/or 2, as determined using the Standard protein-protein BLAST [blastp] software of the NCBI.

According to an additional aspect of the present invention there is provided a soluble fusion protein comprising at least one soluble polypeptide and a heterologous polypeptide being fused thereto, the heterologous polypeptide being normally insoluble and/or suboptimally expressed when expressed in a cell, wherein the at least one soluble polypeptide comprises at least 2 alpha-helical structures being separated therebetween by at least one polypeptide loop, and is composed of a number of amino acid residues selected from a range of about 121 to about 91 or less amino acid residues.

According to yet an additional aspect of the present invention there is provided a soluble fusion protein comprising at least one soluble polypeptide and a heterologous polypeptide being fused thereto, the heterologous polypeptide being normally insoluble and/or suboptimally expressed when expressed in a cell, wherein the at least one soluble polypeptide has a molecular weight which is at least 1.5 times lower than a molecular weight of the heterologous polypeptide.

According to still further features in the described preferred embodiments, the at least one soluble polypeptide has an amino acid sequence at least 65 percent similar to SEQ ID NO: 1 and/or 2, as determined using the Standard protein-protein BLAST [blastp] software of the NCBI.

According to still further features in the described preferred embodiments, the at least one soluble polypeptide comprises at least 2 alpha-helical structures being separated therebetween by at least one polypeptide loop, and is composed of a number of amino acid residues selected from a range of about 121 to about 91 or less amino acid residues.

According to still further features in the described preferred embodiments, the at least one soluble polypeptide has a molecular weight which is at least 1.5 times lower than a molecular weight of the heterologous polypeptide.

According to still further features in the described preferred embodiments, the heterologous polypeptide is a membrane polypeptide.

According to still further features in the described preferred embodiments, the membrane polypeptide is selected from the group consisting of an ion transporter, a neurotransmitter transporter, a sugar transporter and an enzyme.

According to still further features in the described preferred embodiments, the membrane polypeptide is selected from the group consisting of MntH, Kvlm, GAT1, GAT2, GAT3, GAT4, VMAT and HMG-CoA reductase.

According to still further features in the described preferred embodiments, the heterologous polypeptide has a molecular weight of at least 60 kilodaltons According to still further features in the described preferred embodiments, the at least one soluble polypeptide has a molecular weight of 11.5 kilodaltons or less.

According to still further features in the described preferred embodiments, the at least one soluble polypeptide is directly or indirectly fused to an amino terminus of the heterologous polypeptide.

According to still further features in the described preferred embodiments, the at least one soluble polypeptide is directly or indirectly fused to a carboxy terminus of the heterologous polypeptide.

According to still further features in the described preferred embodiments, the at least one soluble polypeptide comprises a first soluble polypeptide which is directly or indirectly fused to an amino terminus of the heterologous polypeptide, and further comprises a second soluble polypeptide which is directly or indirectly fused to a carboxy terminus of the heterologous polypeptide, wherein the second soluble polypeptide is identical or non-identical to the first soluble polypeptide.

The present invention successfully addresses the shortcomings of the presently known configurations by providing optimally small soluble carrier polypeptides which can be fused to an optimally broad range of optimally large heterologous polypeptides, such as membrane proteins, so as to generate fusion proteins which can be produced by host bacteria in high yields, which are optimally soluble, purifiable and crystallizable, and hence optimal for numerous medical and industrial applications.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A depicts the work scheme employed in the disclosed experiments.

FIG. 1B is a schematic diagram of the pET-28a(+) vector.

FIG. 1C is a series of schematic diagrams depicting expression cassettes of cloning vectors for the 8 possible fusion protein configurations.

FIG. 1D is a schematic diagram of representative cloning vector alpha-pET28a(+)-beta for generation of expression vectors for expression of fusion proteins having the alpha-[heterologous polypeptide]-beta configuration.

Figure 1A:
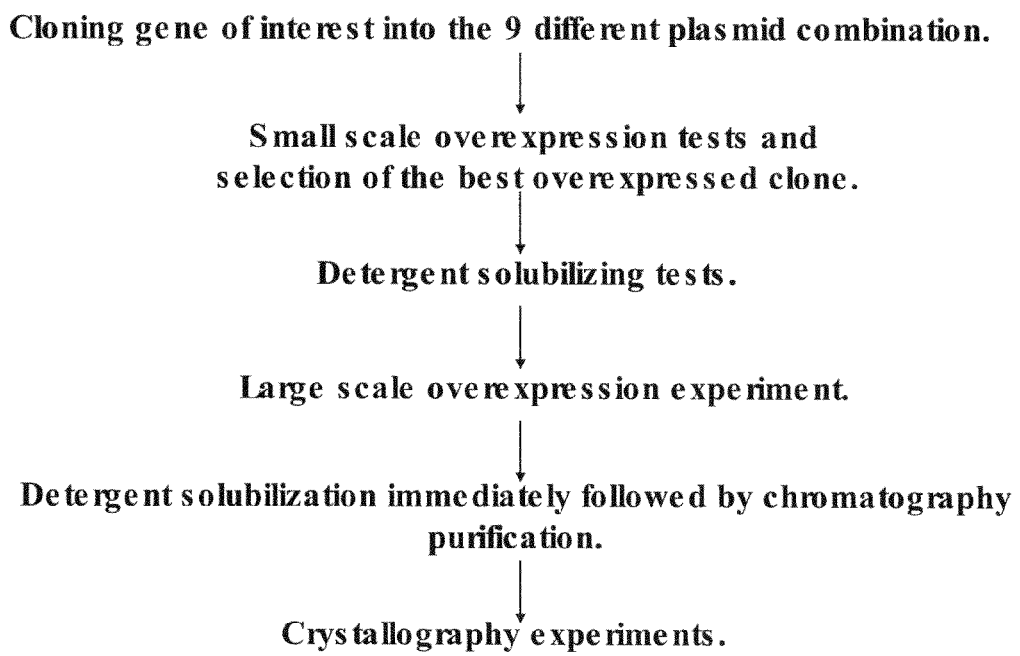
Figure 1B:
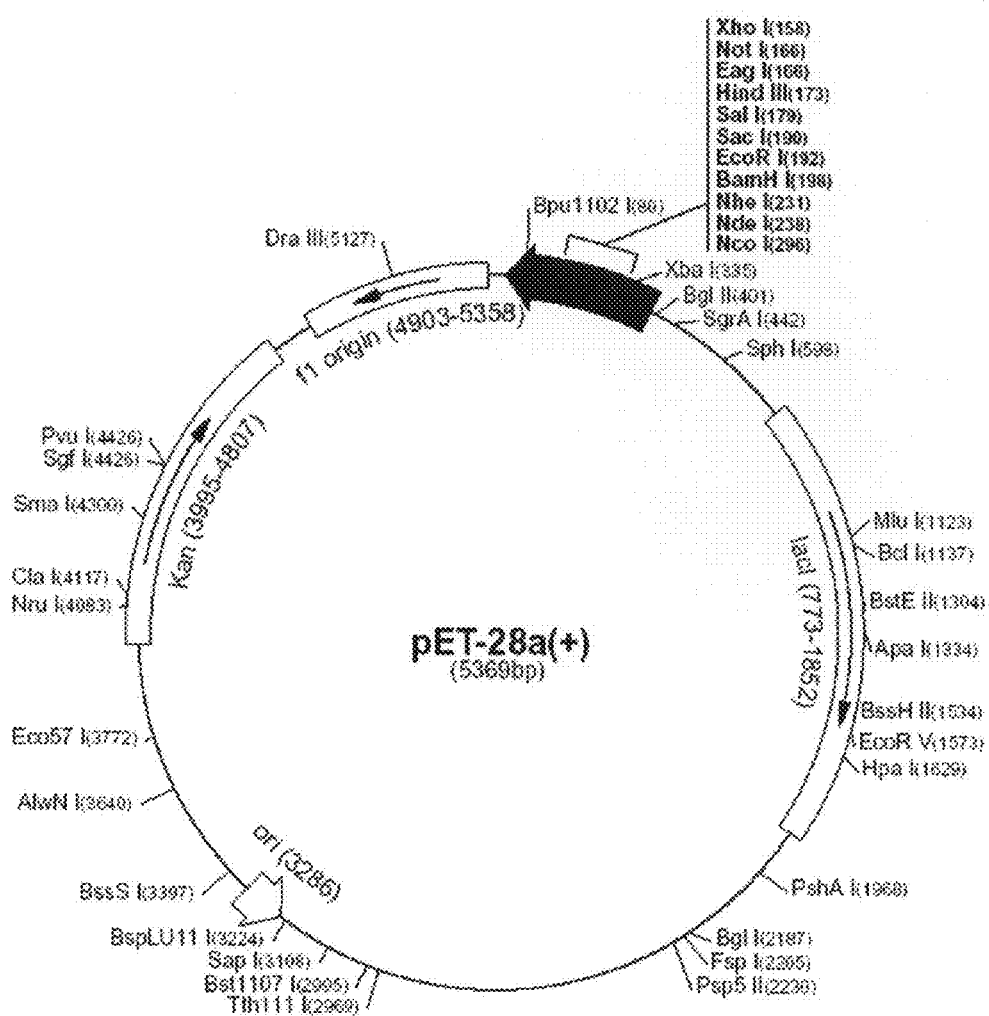
Figure 1C:
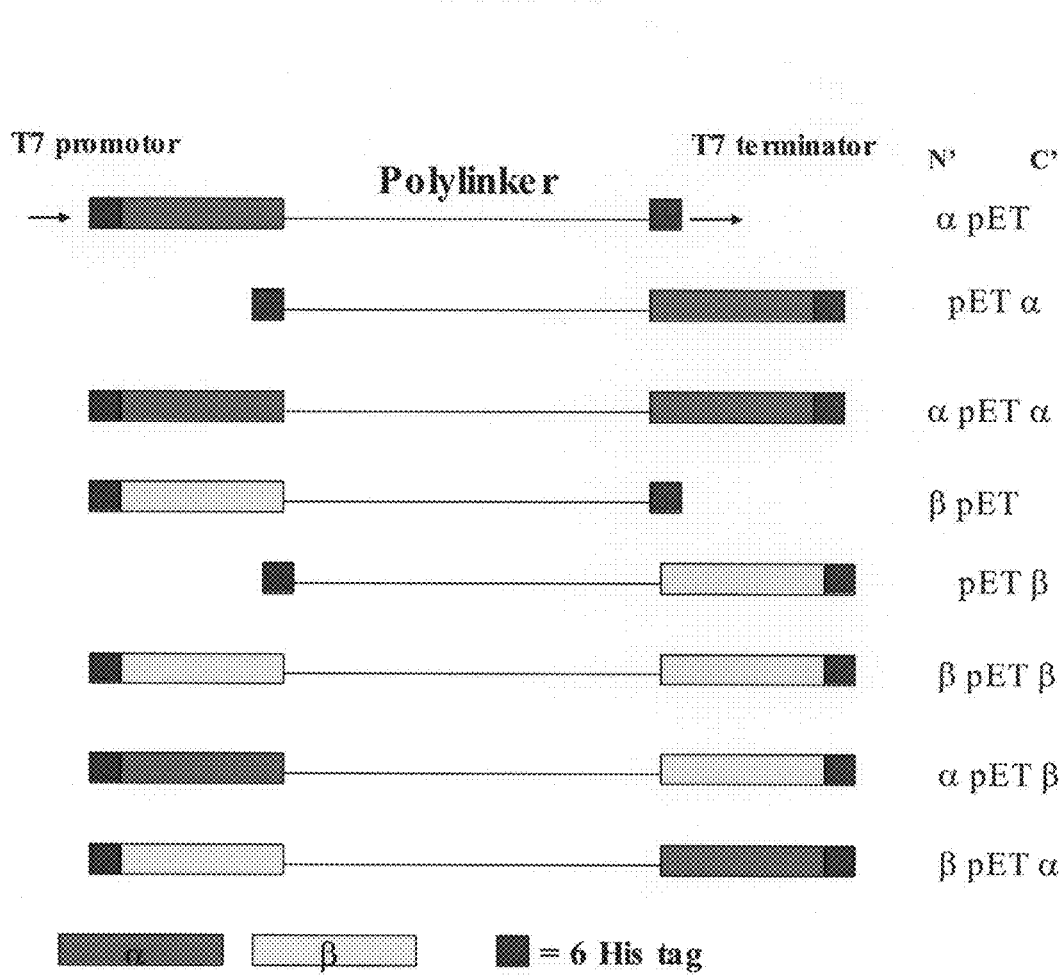
Figure 1D:
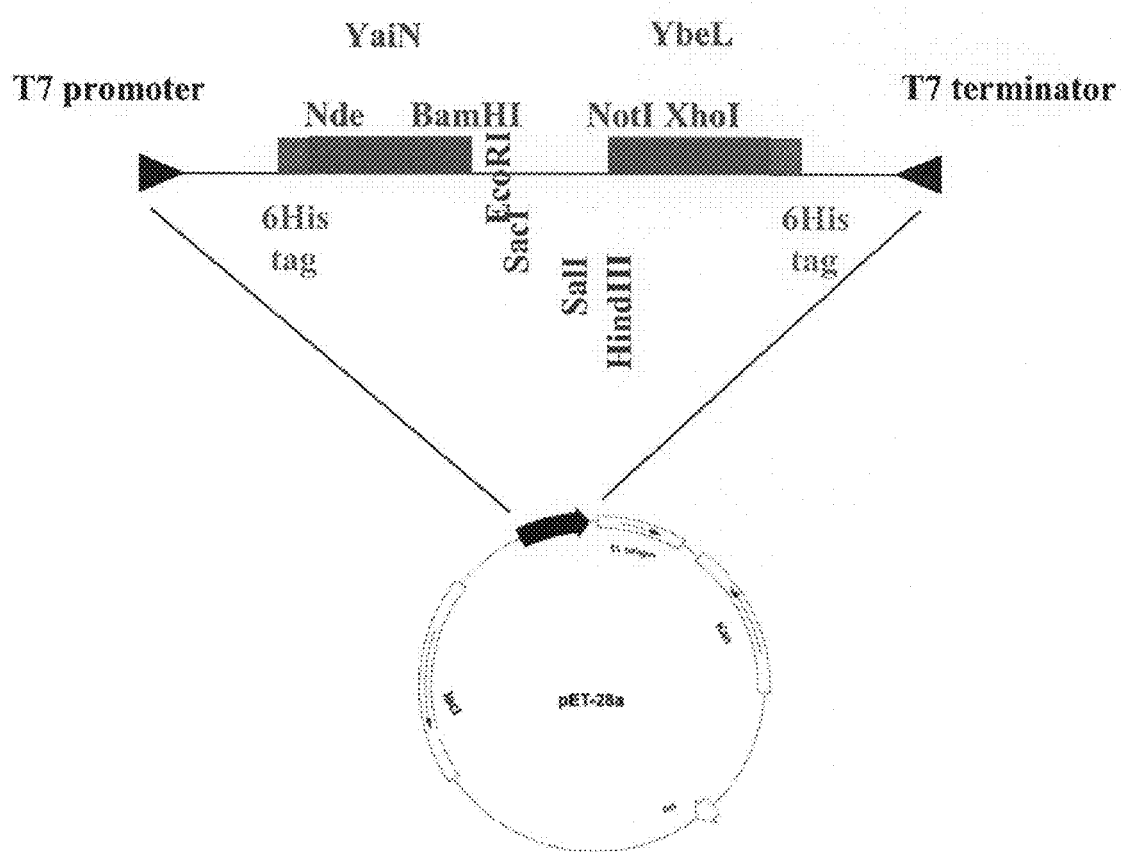
Figure 1E:
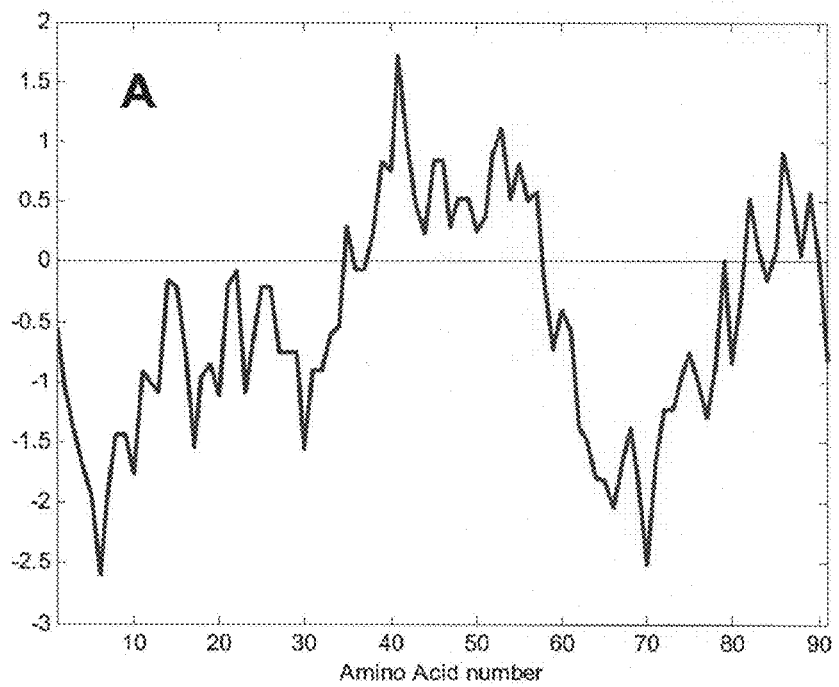
Figure 1F:
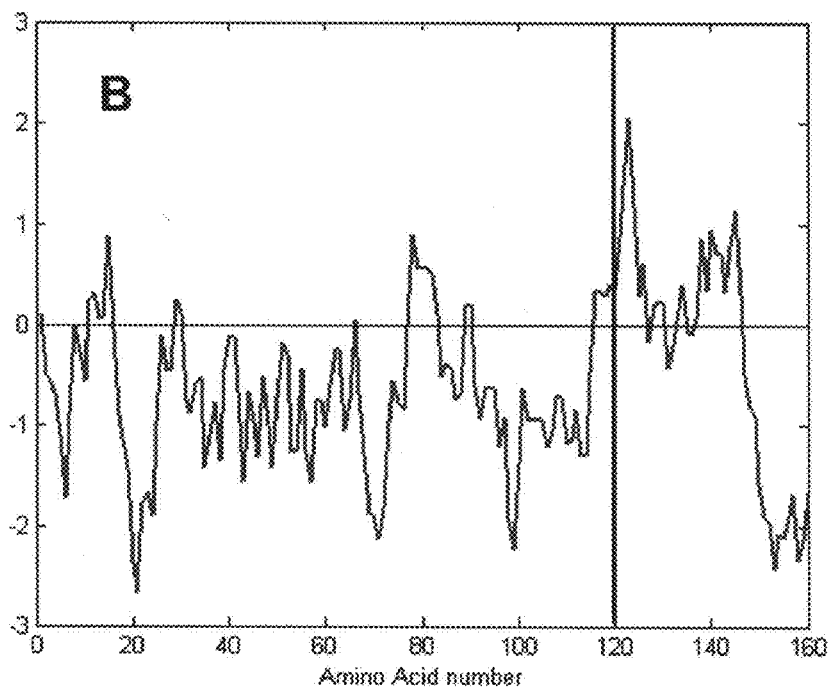

FIGS. 1E-F are Kyle-Doolittle hydrophobicity plots of YaiN(8-98) (SEQ ID NO: 1)and YbeL(1-121) (SEQ ID NO: 2), respectively. The portion to the left of the vertical line in FIG. 1F denotes amino acid residue 121 of YbeL.

Figures 1G, 1H:
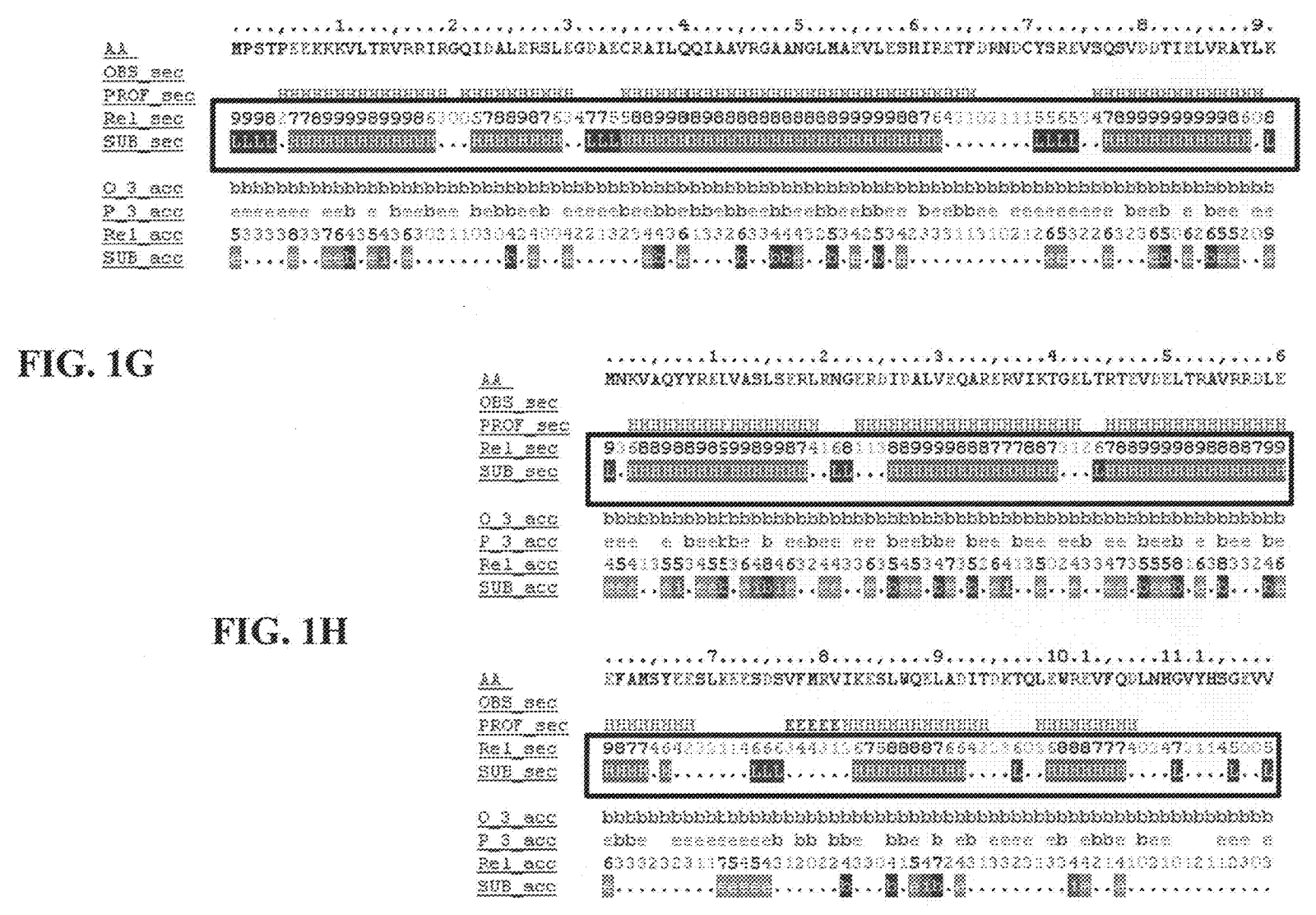

FIGS. 1G-H are schematic diagrams depicting the locations of alpha-helices (H) and polypeptide loops (L) in YaiN (8-98) (SEQ ID NO: 1) and YbeL(1-121) (SEQ ID NO: 2), respectively, predicted using PREDICTPROTEIN software, and shown in the form of the "SUB_sec" values. The legend to the abbreviations is as follows:

AA: amino acid sequence;

OBS_sec, observed secondary structure: H=helix, E=extended (sheet), blank=other (loop)

PROF_sec: PROF predicted secondary structure: H=helix, E=extended (sheet), blank=other (loop)

Rel_sec: reliability index for PROFsec prediction (0=low to 9=high). Note: for the brief presentation strong predictions marked by '*'

SUB_sec: subset of the PROFsec prediction, for all residues with an expected average accuracy>82% (tables in header). NOTE: for this subset the following symbols are used: L: is loop (for which above ' 'is used), and "." means that no prediction is made for this residue, as the reliability is: Rel<5

O_3_acc: observed relative solvent accessibility (acc) in 3 states: b=0-9%, i=9-36%, e=36-100%.

P_3_acc: PROF predicted relative solvent accessibility (acc) in 3 states: b=0-9%, i=9-36%, e=36-100%.

Rel_acc: reliability index for PROFacc prediction (0=low to 9=high). Note: for the brief presentation strong predictions marked by '*'

SUB_acc: subset of the PROFacc prediction, for all residues with an expected average correlation>0.69 (tables in header). NOTE: for this subset the following symbols are used: I: is intermediate (for which above' ' is used), and "." means that no prediction is made for this residue, as the reliability is: Rel<4

Figure 2:
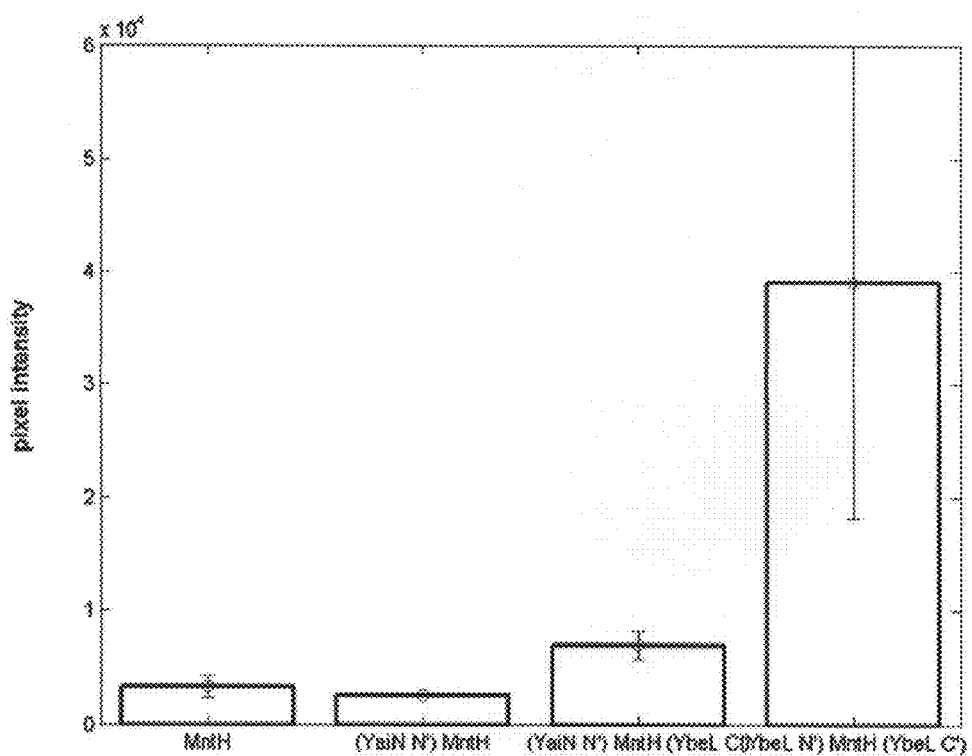

FIG. 2 is a bar graph depicting relative MntH protein expression per milligram total protein.

Figure 3:
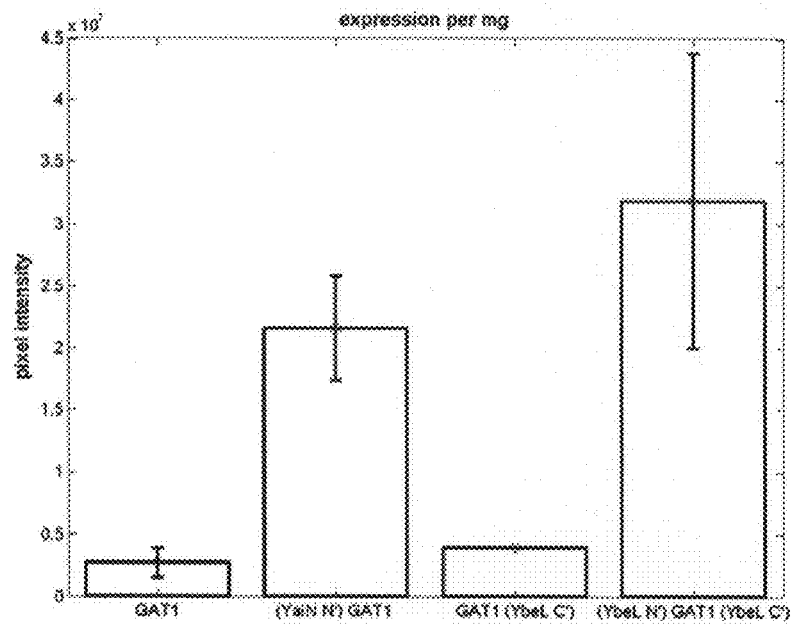

FIG. 3 is a bar graph depicting relative GAT1 protein expression per milligram total protein.

Figure 4:
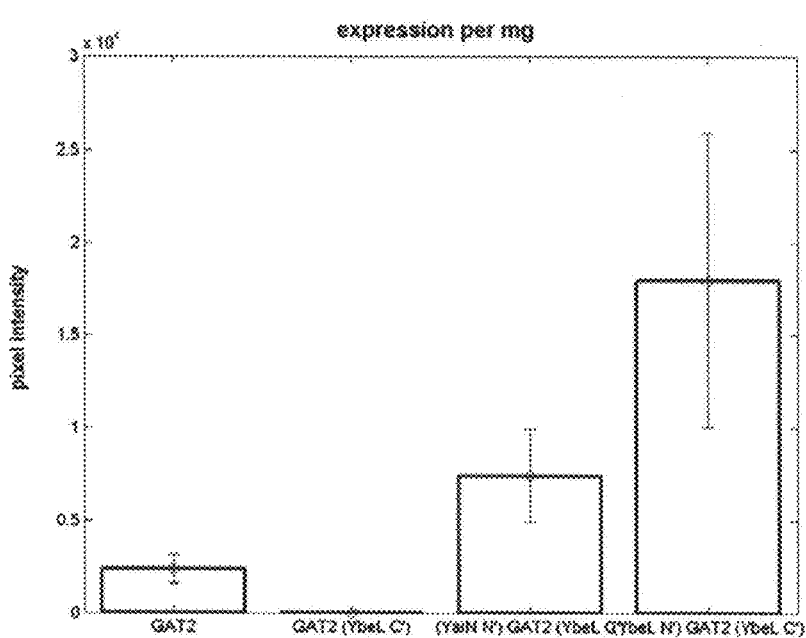

FIG. 4 is a bar graph depicting relative GAT2 protein expression per milligram total protein.

Figure 5:
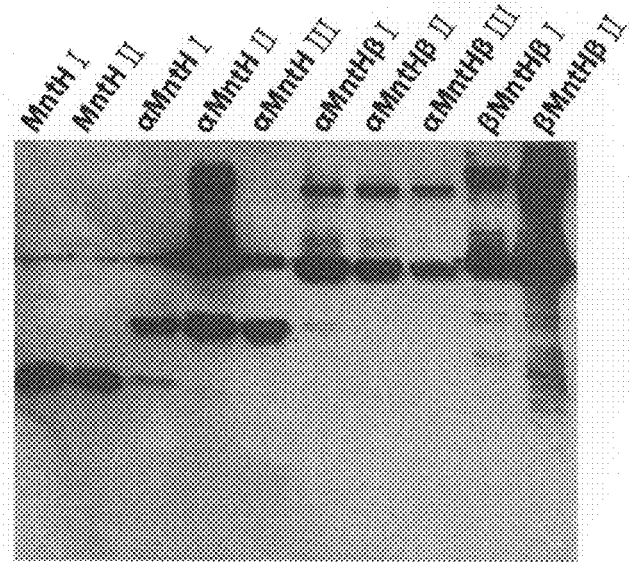

FIG. 5 is a comparative Western blot assay of four different configurations MntH-containing fusion proteins expressed. alpha-MntH and beta-MntH-beta expression level is highest. Sample containing 10 micrograms per milliliter total protein were analyzed, and MntH protein was detected using anti-His-tag monoclonal antibody.

Figure 6:
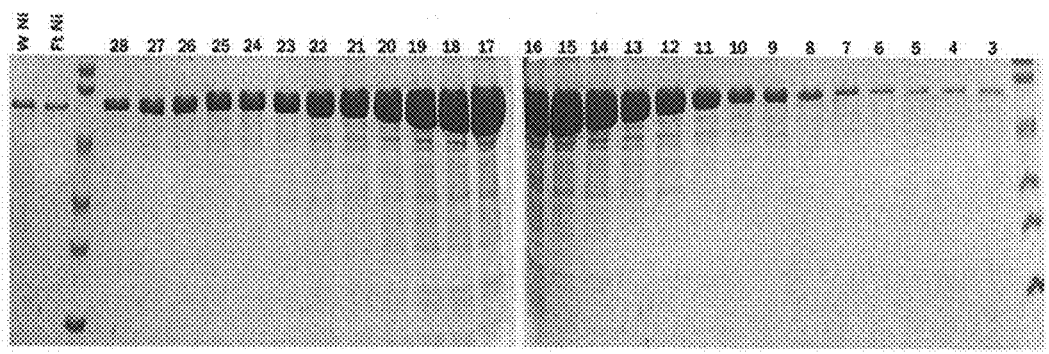

FIG. 6 is an SDS-PAGE analysis depicting that the yield of purified beta-MntH-beta protein was 40-48 milligrams protein per liter culture. Fractions eluted from a Ni-NTA affinity column were subjected to SDS-PAGE and the resultant gels were stained with Coomassie Blue.

Figure 7:
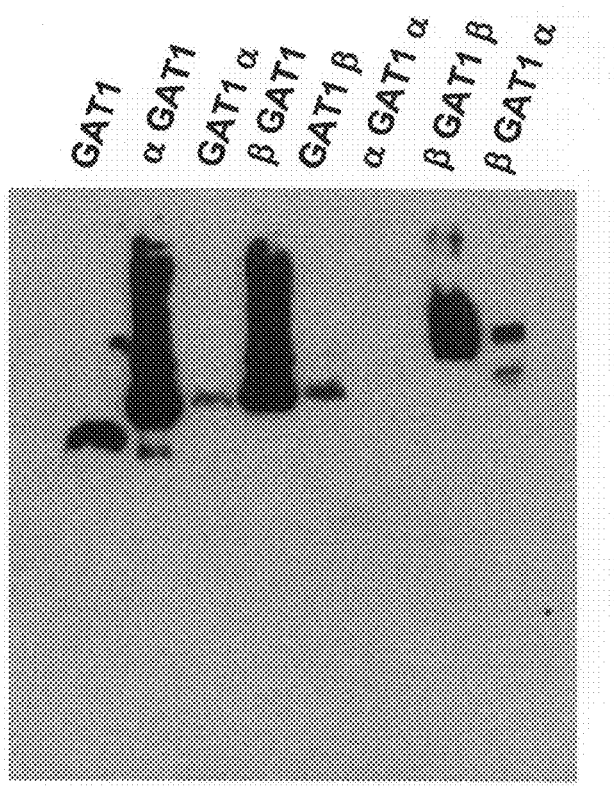

FIG. 7 is a Western blot assay depicting that fusion protein configurations alpha-GAT1, beta-GAT1 and beta-GAT1-beta are optimal for GAT1 expression out of the eight different fusion protein configurations. Fusion proteins were detected using an anti-His-tag monoclonal antibody.

Figure 8:
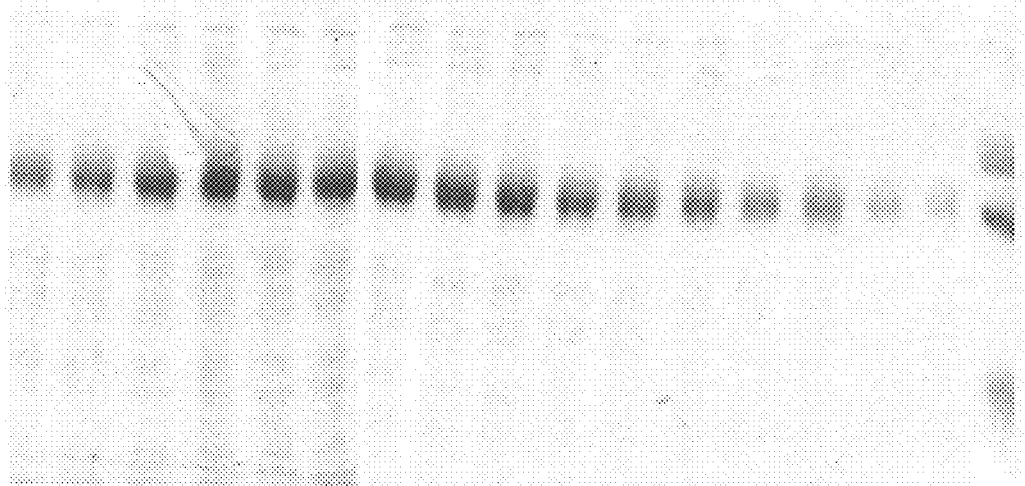

FIG. 8 is an SDS-PAGE analysis of beta-GAT1-beta fractions eluted from a Ni-NTA affinity column. The gel was stained with Coomassie Blue following SDS-PAGE. The yield of purified protein was 1.3-1.7 milligrams protein per liter culture.

Figure 9A:
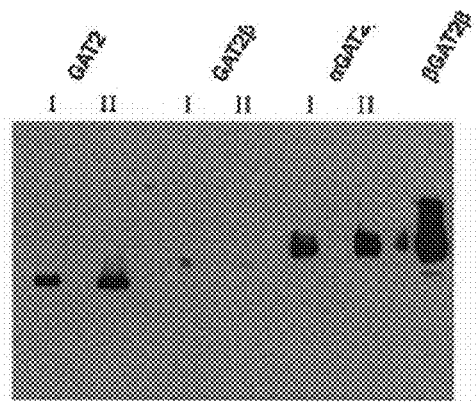
Figure 9B:
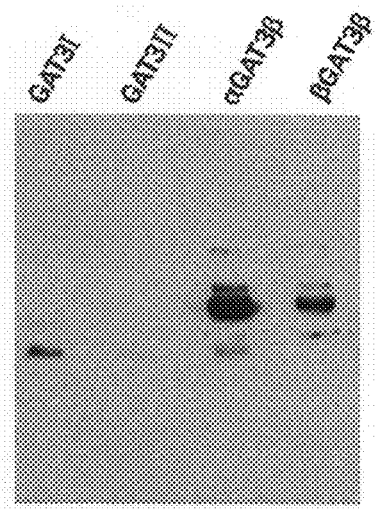

FIGS. 9A-B are electrophoretic analyses respectively depicting that GAT2- and GAT3-containing fusion proteins are expressed at highest levels in the configurations beta-GAT2-beta and alpha-GAT3 -beta, respectively, out of four different configurations of GAT2 fusion proteins, and three configurations of GAT3 fusion proteins tested, respectively.

Figure 10A:
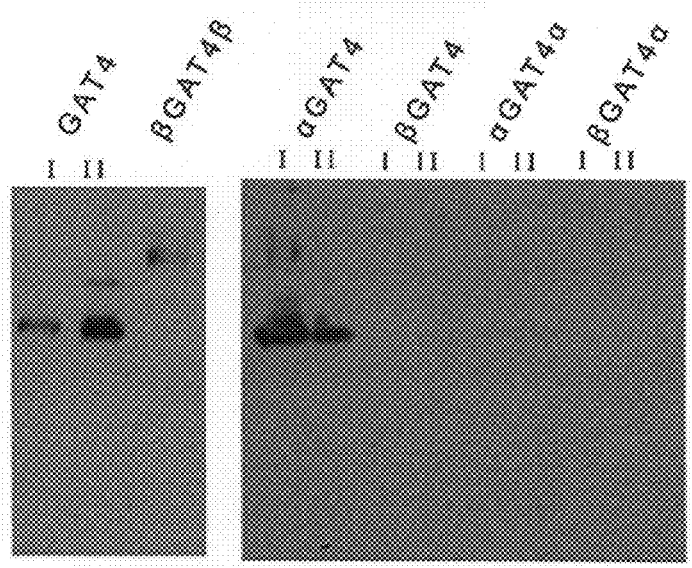

FIG. 10A is a Western blot analysis of expression of four different configurations of GAT4 fusion proteins.

Figure 10B:
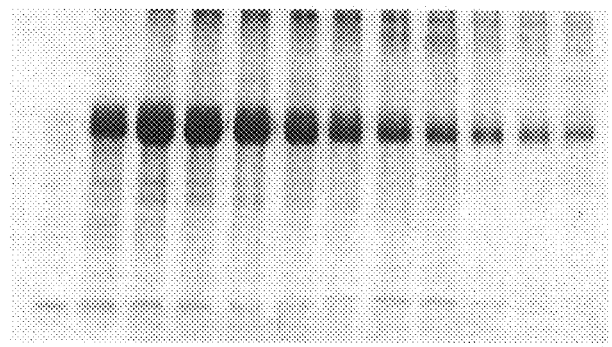

FIG. 10B is an SDS-PAGE analysis depicting that alpha-GAT4 is highly expressed, and readily purified using a Ni-NTA affinity column and FPLC on a monoQ anion exchange column. The fusion protein solubilized in 0.02 percent Fos-Choline-16 was eluted by salt gradient in the presence of the same detergent. The yield of purified alpha-GAT4 was 4.6 milligrams per liter culture. Sequentially eluted fractions are shown. The SDS-PAGE gel was stained with Coomassie Blue.

Figure 11A:
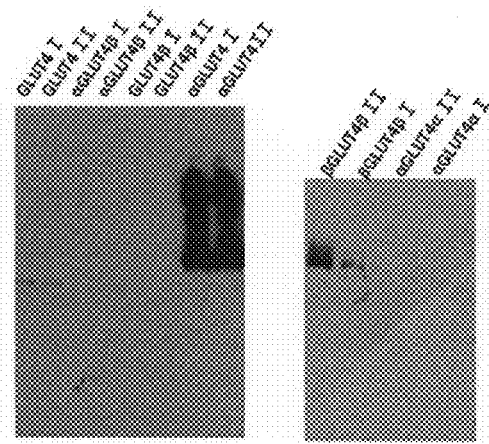

FIG. 11A is a Western blot analysis depicting high-level expression and purification of the alpha-GLUT4 configuration of GLUT4 fusion proteins among four different configurations tested.

Figure 11B:
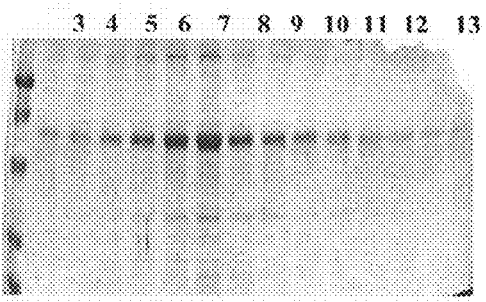

FIG. 11B is an SDS-PAGE analysis depicting high-level purification of alpha-GLUT4. Five-microliter Ni-NTA affinity column fractions were subjected to SDS-PAGE followed by gel-staining with Coomassie Blue. The yield of purified alpha-GLUT4 was 1.4 milligrams per liter culture.

Figure 12A:
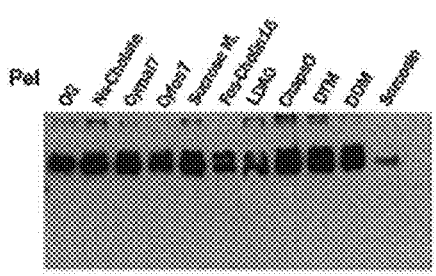
Figure 12B:
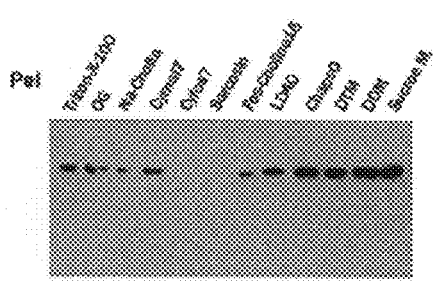

FIGS. 12A-B are SDS-PAGE analyses depicting that beta-GAT1-beta and beta-MntH-beta, respectively, are soluble in various mild detergents. The membrane sample was mixed with 2 percent detergent, incubated for 10 minutes at 0 degrees centigrade and centrifuged for membrane separation. The resultant pelleted membranes (Pel), and the supernatants (Supernatant) were analyzed. Sarcosin, a strong detergent, was used as a positive control for solubilization.

Figure 13:
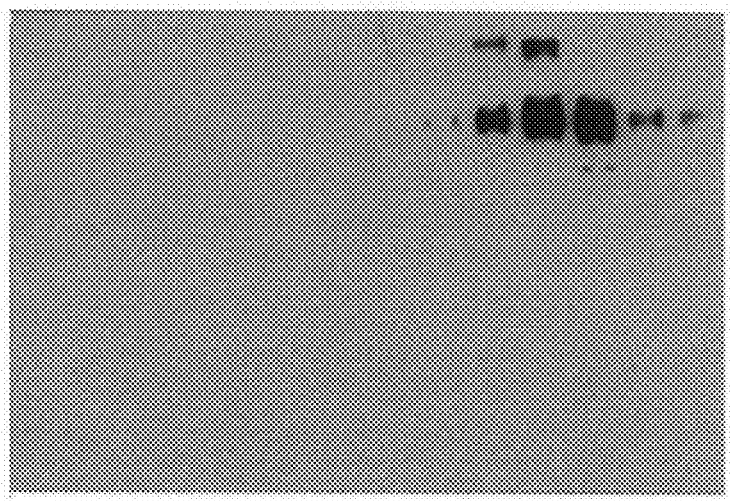

FIG. 13 is a Western Blot depicting monodispersal of expressed beta-GAT1-beta. An SDS-PAGE assay was performed of fractions of purified beta-GAT1-beta solubilized in 0.1 percent Cyclofos-7 obtained by sucrose density gradient centrifugation, as described under Materials and Methods, below. The 15 fractions analyzed were subjected to SDS-PAGE, transferred to a nitrocellulose filter, and the filter was probed with anti-His-tag antibody.

Figure 14:
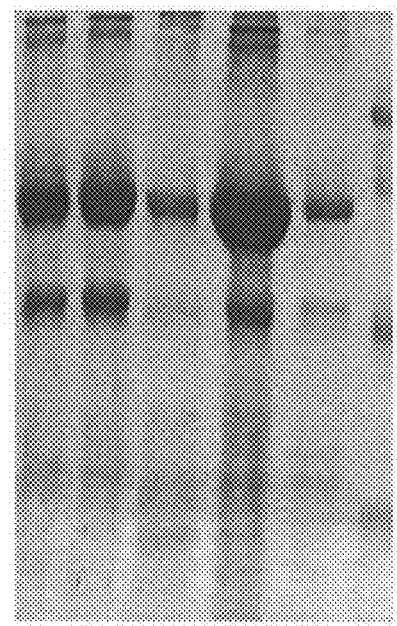

FIG. 14 is a schematic diagram of the secondary structure of mammalian GAT proteins, depicting their 12 transmembrane helices.

Figure 15:
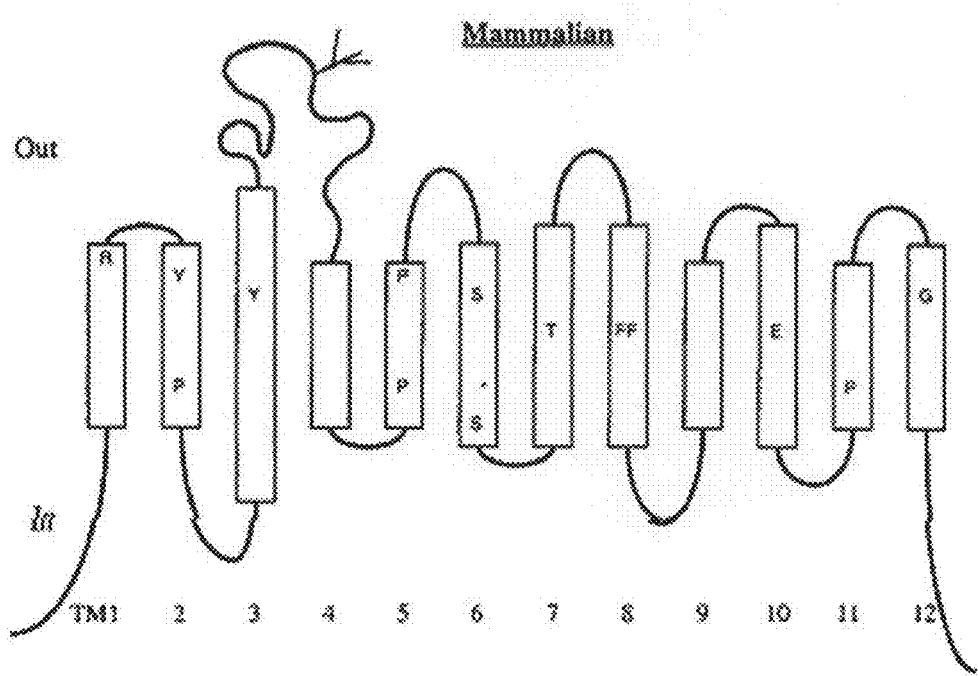

FIG. 15 is an SDS-PAGE analysis depicting that purified beta-MntH-beta exhibits long-term stability under a broad range of crystallization conditions. A solution of the fusion protein at 40 milligrams per milliliter was mixed with an equal volume of various crystallization solution mixes and incubated for 3 months, including at 17 degrees centigrade, prior to analysis. Samples were stained with Coomassie Blue following SDS-PAGE.

Figure 16:
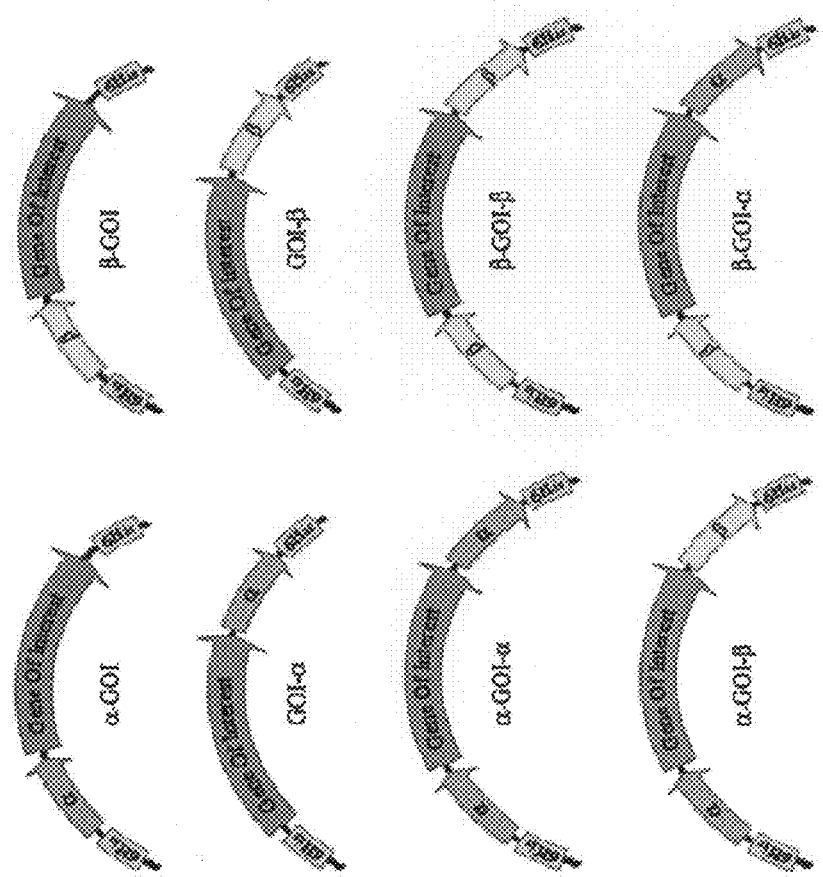

FIG. 16 is a schematic representation of the 8 inducible pET28(a)+expression vectors. Each combination encodes the carrier peptides at different locations. In every combination, the carrier peptide is fused either at the N terminus, the C terminus or at both termini of the Gene Of Interest (GOI) together with 2 HIS tags. The terminology is: left to the GOI is the N' fusion-carrier peptide, right to the GOI is the C' fusion-carrier peptide.

FIGS. 17A-H are western blot analyses of the small-scale overexpression tests. Freshly transformed E.coli colonies were cultured in TB, induced with 1 mM IPTG and growth was continued overnight at 18° C. Cells were harvested, membrane fractions were isolated and their overall protein concentration determined using Bradford reagent. The western blot analysis compares the expression levels of the 9 vector combinations for each membrane protein. In each test, equal protein concentrations were loaded on SDS-PAGE and the separated products were detected with anti-6HIS, directed against the two HIS6-tag of the recombinant overexpressed protein. Small overexpression tests of (FIG. 17A) MntH; (FIG. 17B) GAT1; (FIG. 17C) GAT2; (FIG. 17D) GAT3; (FIG. 17E) GAT4; (FIG. 17F) Kvlm; (FIG. 17G) HMGr; and (FIG. 17H) Vmat.

FIGS. 18A-H are SDS-PAGE analyses depicting that beta-MntH-beta (FIG. 18A); beta-GAT1-beta (FIG. 18B); beta-GAT2-beta (FIG. 18C); alpha-GAT3-beta (FIG. 18D); alpha-GAT4 (FIG. 18E); beta-Kvlm-beta; (FIG. 18F) beta-HMGr-beta (FIG. 18G); and alpha-Vmat (FIG. 18H) are soluble in various mild detergents. The membrane sample was mixed with 2 percent detergent, incubated for 10 minutes at 0 degrees centigrade and centrifuged for membrane separation. The resultant pelleted membranes (Pel), and the supernatants (Supernatant) were analyzed. Sarcosin, a strong detergent, was used as a positive control for solubilization.

FIGS. 19A-H are SDS-PAGE analyses depicting the purification of the HIS6-tagged β-MntH-β. The resultant fractions from each purification were subjected to SDS-PAGE and separated products were visualized by CBB staining. FIG. 19A and FIG. 19E illustrate the Ni-NTA fractions. FIGS. 19B and 19F illustrate the monoQ/Gel-filtration fractions. FIGS. 19C and 19G illustrate the monoQ/Gel-filtration chromatography chart and FIGS. 19D and 19H illustrate the concentrated fraction before crystallization. Concentration was made by PEG precipitation and the protein was resuspended in crystallization buffer. The standard marker size from the top, in kD: 118,85,48,36,26,20

FIGS. 20A-G are SDS-PAGE analyses depicting the purification of the HIS6-tagged β-GAT1-β (FIGS. 20A-D) and α-GAT4 (FIGS. 20E-G). The resultant fractions from each purification were subjected to SDS-PAGE and separated products were visualized by CBB staining. FIGS. 20A, 20C and 20E illustrate Ni-NTA fractions. FIG. 6F illustrates the monoQ/Gel-filtration fractions and FIGS. 20B, 20D and 20G illustrate the concentrated fractions before crystallization. Concentration was made by PEG precipitation and the protein was resuspended in crystallization buffer. The standard marker size from the top, in kD: 118,85,48,36,26,20

FIGS. 21A-H are SDS-PAGE analyses depicting the purification of the HIS6-tagged β-KVLM-β (FIGS. 21A-D) and β-HMGr-β (FIGS. 21E-H). The resultant fractions from each purification were subjected to SDS-PAGE and separated products were visualized by CBB staining. FIG. 21A and FIG. 21E illustrate the Ni-NTA fractions. FIGS. 21B and 21F illustrate the monoQ/Gel-filtration fractions. FIGS. 21C and 21G illustrate the monoQ/Gel-filtration chromatography chart and FIGS. 21D and 21H illustrate the concentrated fraction before crystallization. Concentration was made by PEG precipitation and the protein was resuspended in crystallization buffer. The standard marker size from the top, in kD: 118,85,48,36,26,20

FIGS. 22A-G are Western Blots depicting the oligomerization state of expressed fusion proteins of the present invention. FIG. 22A depicts β-MntH-β. FIG. 22B depicts α-GAT1. FIG. 22C depicts β-Gat1-β. FIG. 22D depicts β-GAT2-β. FIG. 22E depicts α Gat4-β. FIG. 22F depicts β-Kvlm-β. FIG. 22G depicts β-HMGr-β. An SDS-PAGE assay was performed of fractions of the purified fusion proteins solubilized in 0.02-0.1% Cyclofos-7 detergent obtained by sucrose density gradient centrifugation, as described under Materials and Methods, below. The 15 fractions analyzed were subjected to SDS-PAGE, transferred to a nitrocellulose filter, and the filter was probed with anti-His-tag antibody.

Figure 23:
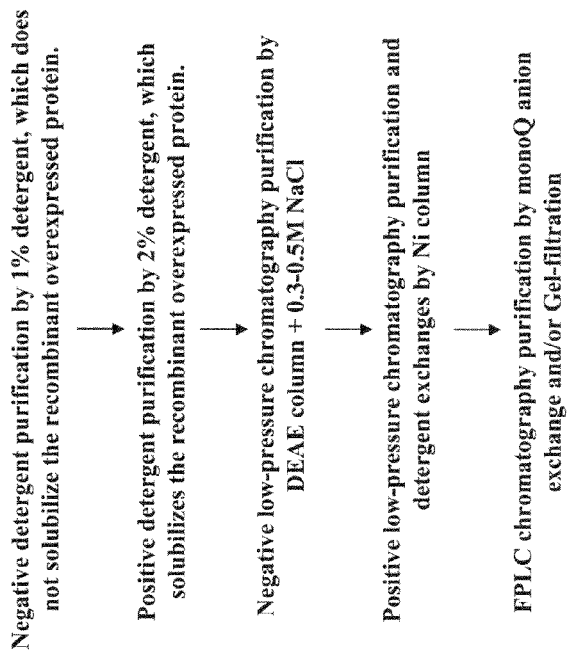

FIG. 23 is a flowchart describing a preferred embodiment of the purification of the fusion proteins of the present invention. The first step is a negative detergent purification in order to remove endogenous membrane proteins from the membrane without solubilizing the overexpressed fusion protein of the present invention. In the next positive detergent purification step, detergent is added to the pellet so as to solubilize the overexpressed protein allowing it to be incorporated into a detergent-protein complex in the supernatant. 0.3-0.5 M NaCl is added to the supernatant which is subsequently placed on a DEAE anion-exchange chromatography in order to remove cell debris, DNA and lipids. The flow-throw from this step is further purified on a Ni-NTA affinity chromatography due to the two HIS 6-tags at both termini of the overexpressed protein. If needed, detergent exchanges may be performed at this step. The final purification step is FPLC chromatography purification by monoQ anion-exchange column and/or Gel-filtration.

Figure 24:
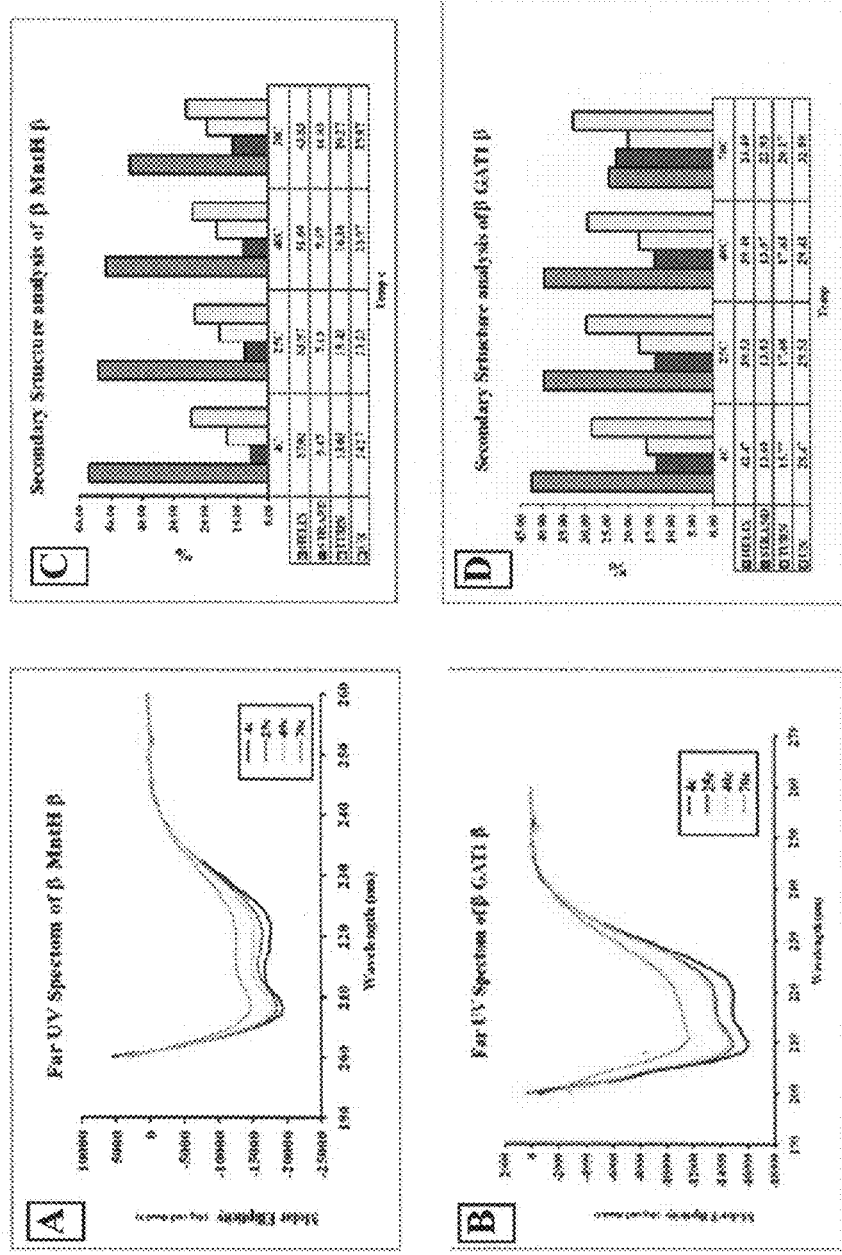

FIGS. 24A-D are graphs illustrating the far UV spectra of purified β-MntH-β, β-GAT1-β (FIG. 24B) and secondary structure calculation of β-MntH-β (FIG. 24C) and β-GAT1-β (FIG. 24D). Spectra were measured over a range of 260-200 nm. The raw data was corrected by subtracting the contribution of the buffer from the CD signal, smoothed and converted to molar ellipticity units. The measurements were taken at 4 increasing temperatures of 4, 25, 40, 70° C., with an approximate protein concentration of 3 μM for β-MntH-β and 6 μM for β-GAT1-β. Deconvolution calculations were computed with CDPRO using CONTIN, CDSSTR and SELCON3 programs with the SMP56 database set. Data is shown as the mean values of the 3 programs for each secondary structure type.

Figure 25:
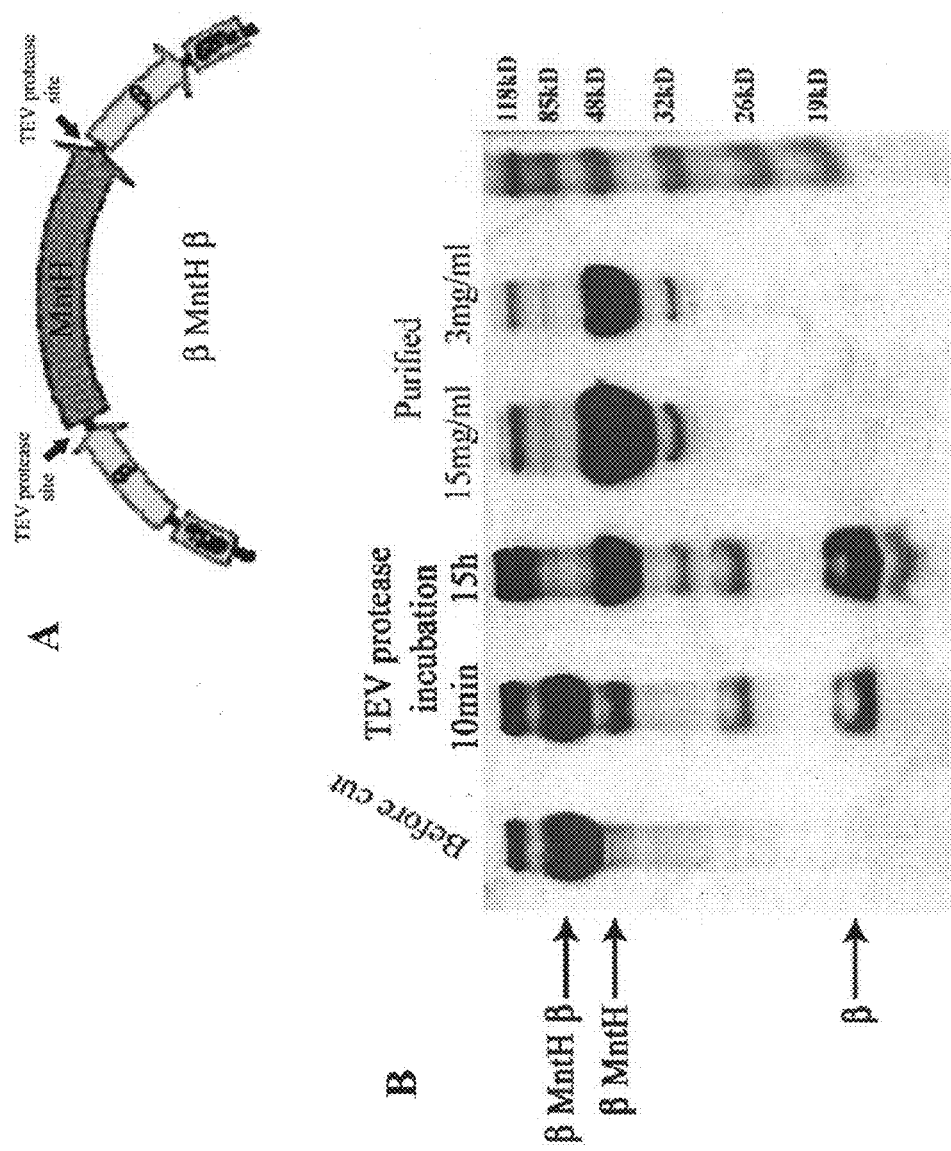

FIG. 25A is a schematic representation of the β-MntH-β containing the two TEV protease cleavage sites.

FIG. 25B is an SDS-PAGE analysis depicting TEV Proteolysis of β-MntH-β. The TEV protease site was cloned into the 8 vectors combinations, so that one or both fusion-proteins could be removed. 15 hours digestion was performed in 4° C. followed by size exclusion chromatography. Proteolysis yielded only one β carrier removal probably due to a tight folding of the other β carrier.

Figure 26:
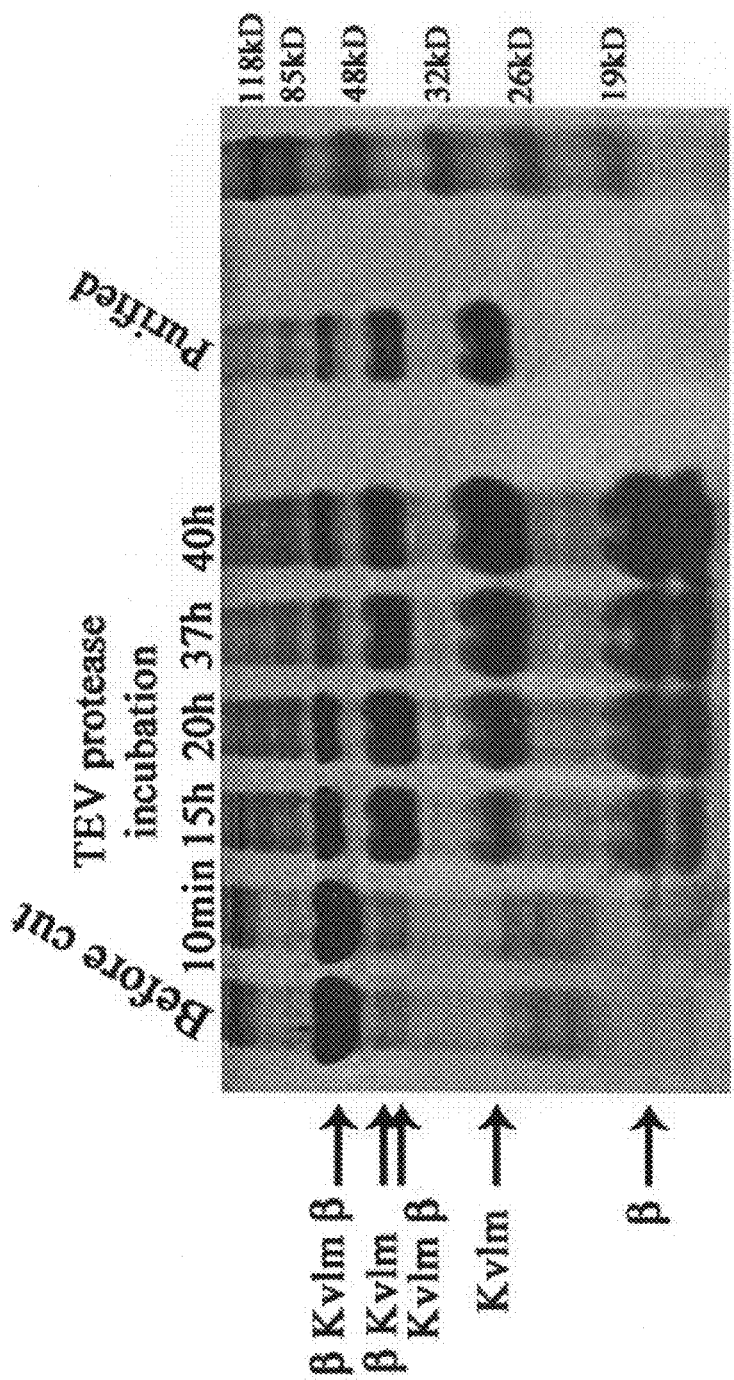

FIG. 26 is an SDS-PAGE analysis depicting TEV Proteolysis of β-Kvlm-β Incubation with TEV protease was performed at 4° C. for 15, 20, 37, and 40 hours, followed by size exclusion chromatography. Proteolysis yielded approximately 80% removal of the two β carrier, 15% removal of one β carrier at the N' termini or C' termini and about 5% of uncut protein.

FIGS. 27A-B are SDS-PAGE analyses depicting trypsine proteolysis of β-Kvlm-β. FIG. 27A illustrates β-Kvlm-β prior to incubation with trypsin. FIG. 27B illustrates β-Kvlm-β following incubation with trypsin. Incubation with trypsin (1/1000 w/w) was performed at 4° C. for 10 min, 30 min, 1 h, 2 h, 3 h and 14 h (ON). Proteolysis yielded approximately 95% removal of the two β carriers.

DESCRIPTION OF THE PREFERRED EMBODIMENTS

The present invention is of soluble fusion proteins which comprise at least one soluble carrier polypeptide fused to a heterologous polypeptide which is normally insoluble and/or suboptimally expressed when expressed in a cell, of recombinant polynucleotides encoding such soluble fusion proteins, of expression vectors which comprise such recombinant polynucleotides and expression control sequences operatively linked thereto and capable of controlling expression thereof in host cells, of host cells transformed or transfected with such expression vectors, of cloning vectors for producing such expression vectors, of kits which comprise such cloning vectors, and of methods of producing such soluble fusion proteins.

Specifically, the present invention can be used for achieving high-level host cell production of soluble fusion proteins where the heterologous polypeptide is a membrane protein, and/or has an optimally high molecular weight, both in absolute terms and relative to that of the carrier polypeptide. As such, the present invention enables the routine generation of optimally large-scale and pure preparations of soluble fusion proteins which comprise heterologous polypeptides, such as membrane proteins, which are normally insoluble and/or suboptimally expressed when expressed in a cell. It will be appreciated that such preparations are optimally or uniquely useful in any of various medical and industrial applications, as further described hereinbelow.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Membrane proteins, which are usually insoluble when expressed in a cell, are involved in the pathogenesis of a vast number of diseases for which no satisfactory or optimal treatment exists. Hence, the capacity to routinely produce such heterologous polypeptides in significant quantities and in a soluble form is highly desirable since this would enable their purification and high-grade crystallization, which would further enable generation of high resolution 3D structure models of their structure via X-ray crystallographic analysis, which in turn would enable computationally assisted design/identification of optimally effective drugs targeted against such polypeptides. Such soluble/purifiable forms of heterologous polypeptides would have other important uses, including direct use as therapeutic and diagnostic agents, use as immunogens for generation of therapeutic/diagnostic antibodies directed thereagainst, and use as research reagents. However, routine production of heterologous polypeptides, such as membrane proteins, in substantial quantities, and in soluble, purifiable and crystallizable form remains highly challenging. Only 88 out of 28,000 high resolution 3D structures solved to date are of membrane proteins, only four of the 88 are of mammalian membrane proteins, and none is of a mammalian integral/transmembrane protein, even though fully 70 percent of all drug targets are targeted to membrane proteins, and even though membrane proteins make up fully 30 percent of all eukaryotic proteins.

One potentially optimal strategy which has been proposed for achieving production of proteins, such as membrane proteins, which are insoluble and/or suboptimally expressed when expressed by a cell involves combining such heterologous polypeptides with carrier molecules so as to generate soluble, purifiable and crystallizable compositions.

Various approaches for producing heterologous polypeptides in soluble, purifiable and crystallizable form by combining such polypeptides with carrier molecules have been described by the prior art. One approach involves combining a heterologous polypeptide with detergents to generate mixed micelles which can be crystallized as a 2D lattice in an artificial lipid bilayer (Stowell M H. et al., 1998. Curr Opin Struct Biol. 8:595). Another approach involves binding of heterologous polypeptides to divalent metal ion-chelated lipids or electrostatically charged lipids so as to generate 2D protein crystals (Frey W. et al., 1996. Proc. Natl. Acad. Sci. U.S.A. 93:4937). Another approach involves combining membrane proteins with lipid nanotubes to generate helical crystals of membrane proteins (Wilson-Kubalek, E. et al., Proc. Natl. Acad. Sci. U.S.A. 1998, 95:8040). A further approach involves complexing membrane proteins with antibody fragments (Hunte, C. and Michel, H., 2002. Curr Opin Struct Biol. 12: 503-508; Hunte C., 2001. FEBS Lett. 504:126-32; Lange C. and Hunte C., 2002. Proc Natl Acad Sci USA. 99:2800-5; Ostermeier C. and Michel H., 1997. Curr Opin Struct Biol. 7:697; Ostermeier C. et al., 1997. Proc Natl Acad Sci USA. 94:10547-53). Yet a further approach involves expressing a fusion protein which comprises the E. coli-derived carrier protein NusA, GrpE, bacterioferritin (Davis, G. D. et al., 1999. Biotechnol. Bioeng. 65: 382-388); or maltose binding protein, glutathione S-transferase (GST), or thioredoxin (Kapust, R. B., Waugh, D. S., 1999. Protein Sci. 8:1668-1674) fused to a heterologous polypeptide. An additional approach involves expressing heterologous polypeptides limited to a molecular weight of 20 kilodaltons as part of a fusion protein in which it is fused to an E. coli carrier protein having a molecular weight which is essentially at least as high as that of the heterologous polypeptide (U.S. Pat. Nos. 6,207,420; 5,989,868). A further approach involves expressing heterologous polypeptides limited to a molecular weight of 16.5 kilodaltons as part of a fusion protein in which it is fused to an E. coli carrier protein (thioredoxin) having a molecular weight which is at least approximately three-quarters that of the heterologous polypeptide (Begum, R. R. et al., 2000. J. Chromatogr. B Biomed. Sci. Appl. 737:119-30).

However, all such prior art approaches suffer from various critical drawbacks. Detergent- and lipid-based approaches are limited to enabling generation of essentially 2D or helical crystals which can only yield structural data of low dimensionality and/or resolution. Antibody-based approaches are expensive time-consuming, cumbersome and inefficient due to the necessity to laboriously adapt the approach with different antibodies for each individual polypeptide of interest. Prior art fusion protein-based approaches are critically limited to a carrier polypeptide which is no smaller than 12 kilodaltons, and to soluble fusion proteins in which the soluble carrier polypeptide must be at least approximately three-quarters as large as the heterologous polypeptide itself. It will be readily appreciated that due to its excessively large relative size the carrier polypeptide will tend to distort the native conformation of the heterologous polypeptide to an excessively large extent via excessively large steric and electrostatic effects. As such, prior art soluble fusion protein-based approaches cannot be used to generate crystallographic data optimally defining the native high resolution structure of a heterologous polypeptide, which is critical for computationally assisted design/identification of optimal drugs specifically targeting the heterologous polypeptide. Furthermore, due to the excessively large relative size of the heterologous polypeptide, prior art fusion protein-based approaches are inherently inefficient for heterologous polypeptide production. Additionally, the excessive conformational distortion of the heterologous polypeptide is highly undesirable for its use, in the form of the fusion protein, as a therapeutic/diagnostic reagent, or as an immunogen for raising antibodies specific for epitopes thereof. Critically, prior art fusion protein-based approaches fail to demonstrate general applicability with respect to a significantly diverse range of heterologous polypeptides.

Thus, the prior art fails to provide a generally applicable and satisfactory/optimal method of combining heterologous polypeptides with a carrier molecule so as to generate a soluble/crystallizable composition, where such heterologous polypeptides are normally insoluble and/or suboptimally expresses when expressed in a cell.

While reducing the present invention to practice, as described in Example 1 of the Examples section below, novel carrier polypeptides having an optimally low molecular weight (as low as 9.9 kilodaltons) were uncovered enabling efficient host cell expression of novel soluble fusion proteins which comprise insoluble membrane proteins of optimally high molecular weight (e.g. 66 kilodaltons), which may comprise an optimally diverse range of insoluble membrane proteins, which are optimally soluble in various mild detergents, and which are highly purifiable, thereby overcoming the limitations of the prior art.

Thus, the present invention enables the routine generation of high-grade crystals of fusion proteins which comprise polypeptides which are normally insoluble and/or suboptimally expressed when expressed in a cell. This in turn enables the generation of high resolution models of such heterologous polypeptides, and thereby enables performance of computationally assisted design/identification of optimal drugs for treating diseases whose pathogenesis is associated with such heterologous polypeptides. Thus, the present invention further enables production heterologous polypeptides in a form which is optimal for use in therapeutic agents, diagnostic agents, and as immunogens for raising antibodies thereagainst with optimal specificity and/or affinity.

Thus, the present invention provides a method of producing in soluble form a heterologous polypeptide which is normally insoluble and/or suboptimally expressed when expressed in a cell. According to the teachings of the present invention, the method is effected by culturing a host cell which is transfected or transformed with a recombinant polynucleotide encoding a soluble fusion protein (hereinafter "the soluble fusion protein") which comprises at least one soluble polypeptide (hereinafter "carrier polypeptide") of the present invention and the heterologous polypeptide fused thereto, where the culturing is effected under culturing conditions causing expression of the polynucleotide in the host cell. Optionally, the method further comprises the step of isolating the soluble fusion protein from the host cell following the culturing thereof.

By virtue of enabling production of a optimally soluble fusion protein which comprises any selected heterologous polypeptide of the present invention, such as a membrane protein, the method of the present invention enables purification of a fusion protein of the present invention which comprises any selected heterologous polypeptide, such as a membrane protein. It will be appreciated that a purified polypeptide, such as a soluble purified fusion protein of the present invention, can be homogeneously crystallized, that homogenous protein crystals can be subjected to X-ray crystallography so as to generate high resolution 3D structure models of crystallized proteins, that such models enable computationally assisted design/identification of specific inhibitory ligands of active sites of such proteins, and that such ligands can be used as drugs for treating diseases whose pathogenesis is associated with the activity of such proteins. As such, it will be appreciated that the method of the present invention enables for the first time the routine obtainment of optimal membrane protein-targeting drugs for treating any of the vast number of diseases whose pathogenesis is associated with membrane protein activity. The method of the present invention is extremely useful since, as described hereinabove, a large majority of all existant drug targets are membrane proteins and approximately 30 percent of all eukaryotic polynucleotides are membrane proteins, whereas the number of currently solved membrane protein structures accounts for an essentially insignificant 0.3 percent of the number all solved protein structures. It will be further appreciated that a purified polypeptide, such as soluble fusion protein of the present invention, can be used in various other ways, including as a vehicle for use of the heterologous polypeptide comprised therein as a therapeutic or diagnostic pharmacological agent, as an immunogen for raising antibodies specific for the heterologous polypeptide, as a research reagent, etc.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "soluble form" when relating to a polypeptide, such as a fusion protein of the present invention, which is expressed by a host cell, such as a recombinant bacterial host cell, refers to the capacity of such a polypeptide to be obtained as a solution of monomers, dimers, and/or natural multimers thereof, where the solution is a soluble fraction of the host cell, or is obtained by detergent treatment of an insoluble fraction of the host cell.

As used herein, the qualifier "heterologous" when relating to the heterologous polypeptide of a soluble fusion protein of the present invention indicates that the heterologous polypeptide is derived from a protein which does not normally comprise any of the carrier polypeptides to which it is fused so as to form the soluble fusion protein.

As used herein, the phrase "heterologous polypeptide which is normally insoluble when expressed in a cell" refers to a polypeptide which is at least partially expressed in insoluble form, such as in the form of inclusion bodies or membrane-sequestered aggregates, when it is expressed under specific cellular expression conditions according to any combination of the following parameters: expressing cell genotype/phenotype, expressing cell density, gene regulator sequences/gene copy number, expressing cell number per volume culturing medium, culturing medium composition/volume, incubator atmosphere composition/temperature, level/type of culture recipient motion, culture recipient type, accessory cell phenotype/density, and the like. For example, membrane proteins such as mammalian membrane proteins are usually not produced in soluble form by recombinant host bacteria such as *E. coli*.

As used herein, the phrase "heterologous polypeptide which is normally suboptimally expressed when expressed in a cell" refers to a polypeptide which is expressible at significantly higher levels when comprised in a soluble fusion protein of the present invention.

As used herein, the term "polypeptide" refers to any polymer of natural or synthetic amino acids.

Soluble fusion proteins of the present invention may be formed using carrier polypeptides of the present invention which are independently or collectively characterized by any of various combinations of secondary structures, amino acid sequences, absolute sizes, and sizes relative to the heterologous polypeptide. Furthermore, any of various combinations of carrier polypeptides of the present invention can be fused to the heterologous polypeptide so as to form the soluble fusion protein.

Preferably, the secondary structure of a carrier polypeptide of the present invention comprises at least 2, and more preferably at least 3, 4 or 5 alpha-helical structures, where the segments are separated from each other, and still more preferably are further flanked on both sides, by a polypeptide loop. Yet more preferably, the secondary structure of a carrier polypeptide of the present invention comprises 5, more preferably 4, and most preferably 3 alpha-helical structures.

An alpha-helical structure of the present invention is preferably a polypeptide segment which comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56 contiguous or non-contiguous amino acid residues scoring as an "H" according to the "SUB_sec" output generated when analyzing an amino acid sequence with PREDICTPROTEIN software (accessible at wwwdotcubidotbiocdotcolumbiadotedu/predictprotein/; described in Rost B. et al., 1996. Protein Sci. 5:1704-18). More preferably, an alpha-helical structure of the present invention is a polypeptide segment which comprises 7, 8, 9, 10, 11, 12, 13, 14, 15, 16, 17, 18, 19, 20, 21, 22, 23, 24, 25, 26, 27, or 28 contiguous or discontiguous amino acid residues thusly scoring as an "H". Preferably, an alpha-helical structure does not comprise any polypeptide loops of the present invention. Preferably, an alpha-helical structure of the present invention has a length of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 amino acid residues. Most preferably, an alpha-helical structure of the present invention has a length of 12, 13, 14, 15, 16, 17, 18, 19, 20, 21, 22, 23, 24, 25, 26, 27, 28, 29, 30, 31, 32, 33, 34, 35, or 36 amino acid residues.

Preferably, a segment which comprises a polypeptide loop of a carrier polypeptide of the present invention has a length selected from a range of 1 to about 30 amino acid residues, more preferably from a range of 2 to about 30 amino acid residues, more preferably from a range of 2 to about 29 amino acid residues, more preferably from a range of 2 to about 28 amino acid residues, more preferably from a range of 2 to about 27 amino acid residues, more preferably from a range of 2 to about 26 amino acid residues, more preferably from a range of 2 to about 25 amino acid residues, more preferably from a range of 2 to about 24 amino acid residues, more preferably from a range of 2 to about 23 amino acid residues, more preferably from a range of 2 to about 22 amino acid residues, more preferably from a range of 2 to about 21 amino acid residues, more preferably from a range of 2 to about 20 amino acid residues, more preferably from a range of 2 to about 19 amino acid residues, more preferably from a range of 2 to about 18 amino acid residues, more preferably from a range of 2 to about 17 amino acid residues, and most preferably from a range of 2 to about 16 amino acid residues.

As used herein the term "about" refers to plus or minus 10 percent.

A polypeptide loop of the present invention is preferably a polypeptide segment which comprises 1, 2, 3, 4, 5, 6, 7, 8, 9, 10, 11, 12, 13, 14, 15, 16, 17, 18, 19, or 20 contiguous or non-contiguous amino acid residues scoring as an "L" according to the "SUB_sec" output generated when analyzing an amino acid sequence with PREDICTPROTEIN software (accessible at wwwdotcubicdotbiocdotcolumbiadotedu/predictprotein/; described in Rost B. et al., 1996. Protein Sci. 5:1704-18). More preferably, polypeptide loop of the present invention is a polypeptide segment which comprises 1, 2, 3, or 4 contiguous or discontinuous amino acid residues thusly scoring as an "L". Preferably, a polypeptide loop of the present invention does not comprise any alpha-helical structures of the present invention. Preferably, a polypeptide loop of the present invention has a length of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 amino acid residues. Most preferably, a polypeptide loop of the present invention has a length of 2, 3, 4, 5, 6, 7, 8, 9, 10, 11, 12, 13, 14, 15, or 16 amino acid residues.

One of ordinary skill in the art will possess the necessary expertise to identify/design suitable alpha-helical structures and polypeptide loops, or to identify/design a polypeptide characterized by such structures, so as to obtain a carrier polypeptide of the present invention, according to the teachings of the present invention.

Without being bound to a paradigm, the present inventors are of the opinion that carrier polypeptides of the present invention are highly effective at solubilizing a substantially hydrophobic heterologous polypeptide by virtue of the capacity of the hydrophilic and rigid alpha-helical structures of the carrier polypeptides to effectively mask hydrophobic/insoluble surfaces of the heterologous polypeptide, and by virtue of the capacity of the polypeptide loops of the carrier polypeptides to enable the carrier polypeptides to adopt conformations allowing their alpha-helical structures to mask optimally large insoluble surfaces of the heterologous polypeptide.

A carrier polypeptide of the present invention may have any of various amino acid sequences so as to enable formation of the soluble fusion protein.

Preferably, a carrier polypeptide of the present invention has an amino acid sequence which is at least 65 percent similar to SEQ ID NO: 1 or 2. More preferably the similarity to SEQ ID NO: 1 or 2 of the amino acid sequence of a carrier polypeptide of the present invention is about 66 percent, more preferably 67 percent, more preferably 68 percent, more preferably 69 percent, more preferably 70 percent, more preferably 71 percent, more preferably 72 percent, more preferably 73 percent, more preferably 74 percent, more preferably 75 percent, more preferably 76 percent, more preferably 77 percent, more preferably 78 percent, more preferably 79 percent, more preferably 80 percent, more preferably 81 percent, more preferably 82 percent, more preferably 83 percent, more preferably 84 percent, more preferably 85 percent, more preferably 86 percent, more preferably 87 percent, more preferably 88 percent, more preferably 89 percent, more preferably 90 percent, more preferably 91 percent, more preferably 92 percent, more preferably 93 percent, more preferably 94 percent, more preferably 95 percent, more preferably 96 percent, more preferably 97 percent, more preferably 98 percent, more preferably 99 percent, and most preferably 100 percent.

Most preferably, a carrier polypeptide of the present invention has an amino acid sequence which is identical to SEQ ID NO: 1 or 2.

A percent similarity of a sample polypeptide to a reference polypeptide, such as that of a carrier polypeptide of the present invention to a polypeptide having an amino acid sequence set forth by SEQ ID NO: 1 or 2, may be determined in any of various ways. Preferably, the percent similarity between polypeptides is determined using the Standard protein-protein BLAST [blastp] software of the NCBI.

As is described in the Examples section which follows, a polypeptide having an amino acid sequence set forth by SEQ ID NO: 1 corresponds to amino acid residues 8-98 of E. coli YaiN [YaiN(8-98); GenBank Accession No. NP_286100], having an optimally low molecular weight of 9.9 kilodaltons and an optimally short length of 91 amino acid residues, and a polypeptide having an amino acid sequence set forth by SEQ ID NO: 2 corresponds to amino acid residues 1-121 of E. coli YbeL [YbeL(1-121); GenBank Accession No. NP_286369], having a molecular weight of 13.2 kilodaltons. The very high hydrophilicity, and hence solubility, of these carrier polypeptides of the present invention is depicted in the Kyle-Doolittle plot of FIGS. 1E-F and their secondary structures, characterized by strong alpha-helices separated by potentially flexible polypeptide loops, are shown in FIGS. 1G-H of the Examples section below, respectively. The Examples section below demonstrates numerous examples of the use of carrier polypeptides corresponding to SEQ ID NO: 1 and/or 2 to successfully enable large-scale production of fusion proteins of the present invention which comprise highly diverse membrane proteins, and which are highly soluble, purifiable, and crystallizable.

Preferably, the soluble fusion protein is formed using one or more carrier polypeptides of the present invention where the carrier polypeptides have a combined molecular weight which is lower than the molecular weight of the heterologous polypeptide by a factor of at least about 1.5, more preferably at least about 1.6, more preferably at least about 1.7, more preferably at least about 1.8, more preferably at least about 1.9, more preferably at least about 2.0, more preferably at least about 2.1, more preferably at least about 2.2, more preferably at least about 2.3, more preferably at least about 2.4, more preferably at least about 2.5, more preferably at least about 2.6, more preferably at least about 2.7, more preferably at least about 2.8, more preferably at least about 2.9, more preferably at least about 3, more preferably at least about 3.1, more preferably at least about 3.2, more preferably at least about 3.3, more preferably at least about 3.4, more preferably at least about 3.5, more preferably at least about 3.6, more preferably at least about 3.7, more preferably at least about 3.8, more preferably at least about 3.9, more preferably at least about 4.0, more preferably at least about 4.1, more preferably at least about 4.2, more preferably at least about 4.3, more preferably at least about 4.4, more preferably at least about 4.5, more preferably at least about 4.6, more preferably at least about 4.7, more preferably at least about 4.8, more preferably at least about 4.9, more preferably at least about 5.0, more preferably at least about 5.1, more preferably at least about 5.2, more preferably at least about 5.3, more preferably at least about 5.4, more preferably at least about 5.5, more preferably at least about 5.6, more preferably at least about 5.7, more preferably at least about 5.8, more preferably at least about 5.9, more preferably at least about 6.0, more preferably at least about 6.1, more preferably at least about 6.2, more preferably at least about 6.3, more preferably at least about 6.4, more preferably at least about 6.5, more preferably at least about 6.6, and most preferably at least about 6.7.

Alternately, the soluble fusion protein may be formed using one or more carrier polypeptides of the present invention where the carrier polypeptides have a combined molecular weight which is lower than that of the heterologous polypeptide by a factor of at least about 7, at least about 8, at least about 9, at least about 10, at least about 20, at least about 25, at least about 30, at least about 35, at least about 40 or at least about 45.

The soluble fusion protein may be formed by one or more carrier polypeptides of the present invention where the combined one or more carrier polypeptides are characterized by any of various molecular weights and/or are composed of any of various numbers of amino acid residues.

A fusion protein of the present invention preferably comprises one or more carrier polypeptides of the present invention which when combined have a minimally low combined molecular weight and/or are composed of a minimal number of amino acid residues, preferably both of which. According to the teachings of the present invention, this enables generation of soluble fusion proteins in which one or more carrier polypeptides of the present invention have minimal combined dimensions relative to the heterologous polypeptide. This will minimize conformational distortion of the heterologous polypeptide by steric and electrostatic effects proportional to the size of the carrier polypeptides, which will be highly desirable in numerous applications of a fusion protein of the present invention, as described further hereinbelow.

Preferably, the soluble fusion protein is formed using one or more carrier polypeptides of the present invention where the carrier polypeptides have a combined molecular weight which is equal to or less than about 13.2 kilodaltons, more preferably equal to or less than about 13.1 kilodaltons, more preferably equal to or less than about 13.0 kilodaltons, more preferably equal to or less than about 12.9 kilodaltons, more preferably equal to or less than about 12.8 kilodaltons, more preferably equal to or less than about 12.7 kilodaltons, more preferably equal to or less than about 12.6 kilodaltons, more preferably equal to or less than about 12.5 kilodaltons, more preferably equal to or less than about 12.4 kilodaltons, more preferably equal to or less than about 12.3 kilodaltons, more preferably equal to or less than about 12.2 kilodaltons, more preferably equal to or less than about 12.1 kilodaltons, more preferably equal to or less than about 12.0 kilodaltons, more preferably equal to or less than about 11.9 kilodaltons, more preferably equal to or less than about 11.8 kilodaltons, more preferably equal to or less than about 11.7 kilodaltons, more preferably equal to or less than about 11.6 kilodaltons, more preferably equal to or less than about 11.5 kilodaltons, more preferably equal to or less than about 11.4 kilodaltons, more preferably equal to or less than about 11.3 kilodaltons, more preferably equal to or less than about 11.2 kilodaltons, more preferably equal to or less than about 11.1 kilodaltons, more preferably equal to or less than about 11.0 kilodaltons, more preferably equal to or less than about 10.9 kilodaltons, more preferably equal to or less than about 10.8 kilodaltons, more preferably equal to or less than about 10.7 kilodaltons, more preferably equal to or less than about 10.6 kilodaltons, more preferably equal to or less than about 10.5 kilodaltons, more preferably equal to or less than about 10.4 kilodaltons, more preferably equal to or less than about 10.3 kilodaltons, more preferably equal to or less than about 10.2 kilodaltons, more preferably equal to or less than about 10.1 kilodaltons, more preferably equal to or less than about 10.0 kilodaltons, and most preferably equal to or less than about 9.9 kilodaltons.

Alternately, the soluble fusion protein be formed using one or more carrier polypeptides of the present invention where the carrier polypeptides have a combined molecular weight which is equal to or less than about 8 kilodaltons, equal to or less than about 7 kilodaltons, equal to or less than about 6 kilodaltons, or equal to or less than 5 kilodaltons.

Preferably, the soluble fusion protein is formed using one or more carrier polypeptides of the present invention where the combined carrier polypeptides are composed of a number of amino acid residues which is equal to or less than about 121, more preferably equal to or less than about 119, more preferably equal to or less than about 118, more preferably equal to or less than about 117, more preferably equal to or less than about 116, more preferably equal to or less than about 115, more preferably equal to or less than about 114, more preferably equal to or less than about 113, more preferably equal to or less than about 112, more preferably equal to or less than about 111, more preferably equal to or less than about 110, more preferably equal to or less than about 109, more preferably equal to or less than about 108, more preferably equal to or less than about 107, more preferably equal to or less than about 106, more preferably equal to or less than about 105, more preferably equal to or less than about 104, more preferably equal to or less than about 103, more preferably equal to or less than about 102, more preferably equal to or less than about 101, more preferably equal to or less than about 100, more preferably equal to or less than about 99, more preferably equal to or less than about 98, more preferably equal to or less than about 97, more preferably equal to or less than about 96, more preferably equal to or less than about 95, more preferably equal to or less than about 94, more preferably equal to or less than about 93, more preferably equal to or less than about 92, and most preferably equal to or less than about 91.

Alternately, the soluble fusion protein may be formed using one or more carrier polypeptides of the present invention where the combined carrier polypeptides are composed of a number of amino acid residues which is equal to or less than about 85, equal to or less than about 80, equal to or less than about 75, equal to or less than about 70, equal to or less than about 65, equal to or less than about 60, equal to or less than about 55, equal to or less than about 50, or equal to or less than about 45 amino acid residues.

A carrier polypeptide of the present invention may optionally comprise a polypeptide linker via which it is fused to the heterologous polypeptide, for example so as to provide flexibility and/or a cleavable sequence which is specifically cleavable with a suitable treatment, such as via a protease specific therefor. Flexible and/or cleavable polypeptide linkers are well known to those of ordinary skill in the art. An example of a flexible linker is the polypeptide Ile-Glu-Gly-Arg which is specifically cleaved by Factor Xa protease. Another example of a cleavable linker is the TEV protease site. The heterologous polypeptides were cleaved (either fully or partially) from their carrier polypeptides by incubation in TEV protease (FIGS. 25B and 26) or trypsin (FIGS. 27A-B). Other polypeptide linkers are known which may be specifically cleaved by trypsin, enterokinase, collagenase or thrombin for example. Alternatively, the polypeptide linker may be specifically cleavable upon exposure to a selected chemical, such as, for example, cyanogen bromide, hydroxylamine, or low pH conditions. It will be appreciated that such a cleavable polypeptide linker will enable isolation of the heterologous polypeptide from a soluble fusion protein of the present invention which comprises the polypeptide linker. It will also be appreciated that a polypeptide linker providing flexibility may enable carrier polypeptides to adopt optimal positioning/conformation for conferring optimal solubility to the soluble fusion protein.

As is shown in FIG. 7 and FIG. 17B of the Examples section which follows, a highly insoluble membrane protein having 12 transmembrane helices and an optimally high molecular weight of 66 kilodaltons (GAT1) could be produced in large quantities as a highly soluble and purifiable fusion protein of the present invention when fused to a carrier polypeptide corresponding to SEQ ID NO: 1, having the about 7-fold lower, optimally low molecular weight of 9.9 kilodaltons, and being composed of 91 amino acid residues. As such, the presently disclosed soluble fusion proteins are far superior for various applications, as described further below, than prior art soluble fusion proteins which are formed using prior art carrier polypeptides having a molecular weight which is at least approximately three-quarters as high as that of the prior art heterologous polypeptide fused thereto.

In order to facilitate identification and/or purification thereof, the fusion protein preferably further comprises at least one detectable moiety, more preferably two detectable moieties. The detectable moiety is preferably an affinity tag.

Alternately, the detectable moiety may be a fluorophore or an enzyme which catalyzes a reaction which generates a detectable product.

Preferably, a detectable moiety of the present invention is an optimally short polypeptide, more preferably a polypeptide which is composed of 6 or less amino acid residues. The optimally short polypeptide may be 2, 3, 4 or 5 amino acid residues long.

Preferably, a detectable moiety of the present invention is positioned so as to form a terminal portion of the fusion protein. More preferably, a first detectable moiety of the present invention is positioned so as to form one terminal portion of the fusion protein and a second detectable moiety of the present invention is positioned so as to form another terminal portion of the fusion protein. Yet more preferably, the first and second detectable moieties are identical. Alternately, depending on the application and purpose, the first and second detectable moieties may be different structurally and/or functionally.

Most preferably, the affinity tag is a His-tag.

The His-tag is a peptide consisting of 4 to 8, most preferably 6, contiguous histidine amino acid residues having the capacity to specifically bind nickel-containing substrates. Ample guidance regarding the use of His-tags for detection and purification of a His-tagged molecule, such as a fusion protein of the present invention, is available in the literature of the art (for example, refer to Sheibani N. 1999. Prep Biochem Biotechnol. 29, 77). Purification of molecules comprising His-tags is routinely effected using nickel-based automatic affinity column purification techniques. An alternate suitable capture ligand for His-tags is the anti-His-tag single-chain antibody 3D5 (Kaufmann, M. et al., 2002. J Mol Biol. 318, 135-47).

Examples of other affinity tags include a streptavidin tag (Strep-tag; GenBank Accession No. S11540), an epitope tag, a maltose-binding protein tag, a chitin-binding domain tag, and a myc-tag (GenBank Accession No. AF329457).

Examples of epitope tags include an 11-mer Herpes simplex virus glycoprotein D peptide, and an 11-mer N-terminal bacteriophage t7 peptide, being commercially known as HSVTag and t7Tag, respectively (Novagen, Madison, Wis., USA), and 10- or 9-amino acid c-myc or *Hemophilus influenza* hemagglutinin (HA) peptides, which are recognized by the variable regions of monoclonal antibodies 9E10 and 12Ca5, respectively.

A Strep-tag is a peptide having the capacity to specifically bind streptavidin. Ample guidance regarding the use of Strep-tags is provided in the literature of the art (see, for example: Schmidt, T G M. and Skerra, A. 1993. Protein Eng. 6, 109; Schmidt TGM. et al., 1996. Journal of Molecular Biology 255, 753-766; Skerra A. and Schmidt T G M., 1999. Biomolecular Engineering 16, 79-86; Sano T. and Cantor C R. 2000. Methods Enzymol. 326, 305-11; and Sano T. et al., 1998. Journal of Chromatography B 715, 85-91).

A suitable maltose-binding domain tag is malE-encoded maltose-binding protein which has the capacity to specifically bind a substrate including amylose such as, for example, an amylose-based affinity purification column. Ample guidance regarding the use of maltose-binding protein as an affinity tag is provided in the literature of the art (see, for example: Guan M. et al., 2002. Protein Expr Purif. 26, 229-34; Cattoli F and Sarti G C, 2002. Biotechnol Prog. 18, 94-100).

A suitable chitin-binding domain tag is B. circulans cbd-encoded chitin binding domain which has the capacity to specifically bind chitin. Ample guidance regarding the use of maltose-binding protein as an affinity tag is provided in the literature of the art (see, for example: Humphries H E et al., 2002. Protein Expr Purif. 26, 243-8; and Chong S. et al., 1997. Gene 192, 271-81).

As is described and demonstrated in Example 1 of the Examples section below, fusion proteins of the present invention which are terminally His-tagged at both termini, and which comprise any one of various heterologous polypeptides of the present invention fused in various configurations to carrier polypeptides of the present invention, can be produced at high levels by a host cell of the present invention (described hereinbelow). As is further described and demonstrated in Example 1 of the Examples section below, such host cell-produced fusion proteins can be routinely highly purified via affinity column chromatography using a capture ligand specific for the His-tag (i.e. using a nickel-NTA column, as described further hereinbelow), and can routinely be detected in a Western blot using an anti-His-tag primary antibody.

Any of various heterologous polypeptides of the present invention can be fused to a carrier polypeptide of the present invention so as to form the soluble fusion protein. More particularly the heterologous polypeptide can belong to any of various classes of proteins, can be characterized by any of various hydrophobicity levels, can have any of various molecular weights, can be endogenous or exogenous to a host cell of the present invention, and can be derived from any of various types of organisms.

One or more carrier polypeptides of the present invention can form a soluble fusion protein of the present invention when fused to a heterologous polypeptide which has a molecular weight of at least about 60 kilodaltons, more preferably at least about 61 kilodaltons, more preferably at least about 62 kilodaltons, more preferably at least about 63 kilodaltons, more preferably at least about 64 kilodaltons, more preferably at least about 65 kilodaltons, and most preferably at least about 66 kilodaltons.

Alternately, one or more carrier polypeptides of the present invention can form a soluble fusion protein of the present invention when fused to a heterologous polypeptide which has a molecular weight of at least about 70 kilodaltons, at least about 80 kilodaltons, at least about 90 kilodaltons, at least about 100 kilodaltons, at least about 150 kilodaltons, at least about 200 kilodaltons, at least about 250 kilodaltons, at least about 300 kilodaltons, at least about 350 kilodaltons, or at least about 400 kilodaltons.

The heterologous polypeptide is preferably a membrane protein or at least a membranal portion (domain) of a membrane protein. The membrane protein is preferably a transmembrane protein, and the membranal portion of the transmembrane protein is preferably a transmembranal portion thereof. The membrane protein may have any of various numbers of membrane and/or transmembrane domains. For example, the heterologous polypeptide may be a transmembrane protein having 12 transmembrane domains.

Preferably the membrane protein is a transmembrane transporter and/or channel protein. Preferably, the transporter/channel protein is an ion transporter, a neurotransmitter transporter, and/or a sugar transporter.

The ion transporter may be divalent ion transporter, a cation transporter, a pH-dependent secondary ion transporter, a metal ion transporter. The ion transporter may be a divalent metal ion transporter, e.g. a member of the NRAMP family of divalent metal ion transporters such as MntH. The MntH may be derived from a bacterium such as from E. coli. As described in Example 1 of the Examples section below, E. coli MntH belongs to the NRAMP family of eukaryotic divalent metal ion transporters, characterized as pH-dependent secondary transporters (Courville, P. et al., 2004. J. Biol. Chem. 279: 3318-3326; Makui, H. et al., 2000. Mol. Microbiol. 35:1065-1078).

The ion transporter may also be a monovalent metal ion transporter. As illustrated in FIG. 17F, the carrier polypeptides of the present invention were able to increase expression of a bacterial depolarization-activated K(+) (Kv) channel (Kvlm).

The neurotransmitter transporter may be a GABA neurotransmitter transporter such as GAT1, GAT2, GAT3 or GAT4. Preferably the neurotransmitter transporter is derived from a mammal, most preferably a human. GAT protein family proteins share 50-70 percent amino acid sequence homology. These proteins have a typical predicted structure of the Na+/Cl− neurotransmitter transporters, with 12 transmembrane helices, have both termini facing the cytoplasm and have an external loop with predicted glycosylation sites.

The neurotransmitter transporter may also be a monoamine transporter which transports monoamines such as serotonin, dopamine, norepinephrine, epinephrine and histamine into storage organelles. The present inventors have shown that the carrier polyp eptides of the present invention were able to increase expression of VMAT (FIG. 17H).

The sugar transporter may be a hexose transporter such as a glucose transporter. For example, the glucose transporter may be a GLUT-family transporter such as GLUT 4 (see FIGS. 11A-B). Preferably, the sugar transporter is derived from a mammal, most preferably a human.

The membrane protein may also be an enzyme. Thus, for example the present inventors have shown (FIG. 17G) that the carrier polypeptides of the present invention were able to increase the expression of HMG-CoA reductase (HMGR) which is responsible for the conversion of HMG-CoA to Mevalonate (MVA). This is the major regulatory step in the MVA pathway. MVA is the first committed precursor for biosynthesis of cholesterol and a variety of essential nonsterol isoprenoids.

The heterologous polypeptide may be naturally produced by (derived from) the host cell. Alternately, the heterologous polypeptide may be exogenous to the host cell.

As described hereinabove and in Example 1 of the Examples section which follows, the heterologous polypeptide may be derived from a eukaryote, such as mammal, such as a human; or from a prokaryote, such as a bacterium, such as E. coli. Due to the great phylogenetic divergence between a human and E. coli it will be appreciated that one or more carrier polypeptides of the present invention can be used to form the soluble fusion protein when fused to a heterologous polypeptide which is derived from essentially any biological source, including a prion, a virus, a mycoplasma, a protozoan, an algae, a fungus, a plant and a metazoan animal.

The carrier polypeptides can be fused to the heterologous polypeptide in any of various configurations so as to form the soluble fusion protein.

According to teachings of the present invention, the soluble fusion protein is preferably formed by fusing a carrier polypeptide of the present invention directly or indirectly to the amino terminus of the heterologous polypeptide.

Alternately, the soluble fusion protein can be formed by fusing a carrier polypeptide of the present invention directly or indirectly to the carboxy terminus of the heterologous polypeptide.

Further alternately, the soluble fusion protein can be formed by fusing a first carrier polypeptide of the present invention directly or indirectly to one terminus of the heterologous polypeptide and by fusing a second carrier polypeptide of the present invention directly or indirectly to the other terminus of the heterologous polypeptide, where the first and second carrier polypeptides are identical or non-identical.

Suitable configurations of the soluble fusion protein with respect to carrier polypeptides of the present invention and their positioning are described in the Examples section which follows.

Preferably, where the heterologous polypeptide is a neurotransmitter transporter of the present invention, the fusion protein is formed by fusing the carrier polypeptide corresponding to SEQ ID NO: 2 to both termini of the heterologous polypeptide, by fusing the carrier polypeptide corresponding to SEQ ID NO: 2 to the amino terminus of the heterologous polypeptide, by fusing the carrier polypeptide corresponding to SEQ ID NO: 1 to the amino terminus of the heterologous polypeptide, or by fusing the carrier polypeptides corresponding to SEQ ID NO: 1 and SEQ ID NO: 2 to the amino and carboxy termini of the heterologous polypeptide, respectively.

Where the heterologous polypeptide is a GAT1 protein of the present invention, all the combinations of the fusion proteins are preferable, except the combination of fusing the carrier polypeptide corresponding to SEQ ID NO: 2 to the carboxy terminus of the heterologous polypeptide.

Preferably, where the heterologous polypeptide is a GAT2 protein of the present invention, the fusion protein is formed by fusing the carrier polypeptide corresponding to SEQ ID NO: 2 to both termini of the heterologous polypeptide.

Preferably, where the heterologous polypeptide is a GAT3 protein of the present invention, the fusion protein is formed by fusing the carrier polypeptides corresponding to SEQ ID NO: 1 and SEQ ID NO: 2 to the amino and carboxy termini of the heterologous polypeptide, respectively or alternatively by fusing the carrier polypeptides corresponding to SEQ ID NO: 2 and SEQ ID NO: 1 to the amino and carboxy termini of the heterologous polypeptide, respectively.

Preferably, where the heterologous polypeptide is a GAT4 protein of the present invention, the fusion protein is formed by fusing the carrier polypeptide corresponding to SEQ ID NO: 1 to the amino terminus of the heterologous polypeptide, or alternatively by fusing the carrier polypeptides corresponding to SEQ ID NO: 1 and SEQ ID NO: 2 to the amino and carboxy termini of the heterologous polypeptide, respectively.

Preferably, where the heterologous polypeptide is Vmat, the fusion protein of the present invention is formed by fusing the carrier polypeptide corresponding to SEQ ID NO:2 to the amino terminus of the heterologous polypeptide.

Preferably, where the heterologous polypeptide is Glut4, the fusion protein is formed by fusing the carrier polypeptide corresponding to SEQ ID NO: 1 to the amino terminus of the heterologous polypeptide.

Preferably, where the heterologous polypeptide is HMGR, the fusion protein is formed by fusing the carrier polypeptide corresponding to SEQ ID NO: 2 to the amino terminus of the heterologous polypeptide. Alternatively, the fusion protein my be formed by fusing the carrier polypeptide corresponding to SEQ ID NO: 2 to the amino terminus of the heterologous polypeptide and fusing either the carrier polypeptide corresponding to SEQ ID NO: 1 or 2 to the carboxy terminus of the heterologous polypeptide.

Preferably, where the heterologous polypeptide is an ion transporter such as MntH, the fusion protein is formed by fusing the carrier polypeptide corresponding to SEQ ID NO: 2 to either the amino terminus or both termini of the heterologous polypeptide. Alternatively, the fusion protein may be formed by fusing the carrier polypeptide corresponding to SEQ ID NO: 2 to the amino terminus and fusing the carrier polypeptide corresponding to SEQ ID NO: 1 to the carboxy terminus. Conversely, the fusion protein may also be formed by fusing the carrier polypeptide corresponding to SEQ ID NO: 1 to the amino terminus and fusing the carrier polypeptide corresponding to SEQ ID NO: 2 to the carboxy terminus. Still alternatively, the fusion protein may be formed by fusing the carrier polypeptide corresponding to SEQ ID NO: 1 to the carboxy terminus.

Preferably, where the heterologous polypeptide is an ion transporter such as KVLM, all the combinations of the fusion proteins are preferable, except the combination of fusing the carrier polypeptide corresponding to SEQ ID NO: 1 to both the amino and carboxy termini of the heterologous polypeptide.

As is described and demonstrated in Example 1 of the Examples section below soluble fusion proteins such as those which comprise the aforementioned heterologous polypeptides of the present invention fused to carrier polypeptides in the aforementioned configurations can be produced, according to the method of the present invention, in significant amounts, are highly purifiable and/or are highly stable under long-term crystallization conditions.

Thus, the present invention provides a soluble fusion protein which comprises at least one carrier polypeptide of the present invention and a heterologous polypeptide of the present invention fused thereto.

Depending on the application and purpose, the soluble fusion protein can be expressed by a host cell of the present invention which is of any of various types, and which is transformed or transfected in any of various ways so as to be capable of expressing the fusion protein.

Preferably, the host cell is a prokaryote, more preferably a bacterium, more preferably an *E. coli* bacterium. General relevant guidance relating to obtaining and utilizing host cells for producing a recombinant polypeptide, such as a soluble fusion protein of the present invention, is provided hereinbelow.

Preferably, the host cell has a genetic background enabling it under appropriate conditions to express the soluble fusion protein at a temperature of less than 20 degrees centigrade.

Most preferably, the *E. coli* bacterium belongs to *E. coli* strain C43 (DE3), such strain having the capacity to be grown at a temperature of less than 20 degrees centigrade.

As is described and illustrated in Example 1 of the Examples section below, *E. coli* strain C43 (DE3) cells transformed with such a recombinant nucleotide can be used to satisfactorily express a soluble fusion protein of the present invention. General relevant guidance relating to obtaining and utilizing host cells for expressing a recombinant polypeptide, such as a recombinant polypeptide encoding a soluble fusion protein of the present invention, is provided hereinbelow.

The soluble fusion protein is preferably expressed by a host cell which has been transfected or transformed with a recombinant polynucleotide which encodes the soluble fusion protein, where the recombinant polynucleotide comprises one or more polynucleotides encoding one or more carrier polypeptides (hereinafter "carrier-encoding polynucleotides") of the present invention, and comprises a polynucleotide encoding the heterologous polypeptide (hereinafter "heterologous polypeptide-encoding polynucleotide"), where the carrier-encoding polynucleotides and the heterologous polypeptide-encoding polynucleotide are positioned in frame with respect to each other so as to encode the soluble fusion protein.

As appropriate, the encoding polynucleotides are preferably complementary DNAs (cDNAs). Complementary DNAs can be derived from reverse transcription of messenger RNA using a reverse transcriptase or any other RNA dependent DNA polymerase. Such sequences can be subsequently amplified via polymerase chain reaction (PCR) using a DNA dependent DNA polymerase. Preferably, the encoding polynucleotides comprise suitable sequences, such as suitable restriction sites, enabling these to be ligated with a complementary sequence, according to standard methodology, so as to generate the recombinant polynucleotide.

To facilitate recovery follow expression thereof, the recombinant polypeptide may comprise a cleavable moiety designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

It will be appreciated by the ordinarily skilled artisan that the codon usage of a recombinant polynucleotide and vector of the present invention should be suitable to enable expression of the fusion protein in the host cell. It will be further appreciated that the codon usage may be selected so as to optimize expression of the fusion protein in the host cell. One of ordinary skill in the art will possess the necessary expertise to suitably select an appropriate codon usage, depending on the application and purpose. Relevant general guidance relating to obtaining and utilizing recombinant polynucleotides which can be used to transform or transfect host cells so as to enable these to express a recombinant polypeptide is provided hereinbelow. Most preferably, the recombinant polynucleotide is obtained and utilized according to the guidelines provided in Example 1 of the Examples section which follows. As is described and illustrated in Example 1 of the Examples section which follows, a soluble fusion protein of the present invention can be expressed by a host cell of the present invention which is transformed with a recombinant polynucleotide of the present invention.

Thus, the present invention provides a recombinant polynucleotide which encodes a soluble fusion protein of the present invention, where the recombinant polynucleotide comprises one or more polynucleotides encoding one or more carrier polypeptides of the present invention, and further comprises a polynucleotide encoding a heterologous polypeptide of the present invention, where the carrier-encoding polynucleotides and the heterologous polypeptide-encoding polynucleotide are positioned in frame with respect to each other so as to encode the soluble fusion protein.

The host cell is preferably transformed or transfected with an expression vector which comprises the recombinant polynucleotide, and which further comprises and at least one expression control sequence which is operatively linked to the recombinant polynucleotide, and which is capable of controlling expression of the recombinant polynucleotide in the host cell so as to enable production of the soluble fusion protein thereby.

Preferably, the expression control sequences employed comprise a promoter enabling inducible expression of the fusion protein when the cells are cultured in the presence of an inducer. Preferably, the inducer is isopropyl beta-D-thiogalactoside (IPTG), and the IPTG-inducible promoter is a T7 promoter. IPTG-induced expression of polynucleotides, such as recombinant polynucleotides of the present invention, which are under the regulatory control of a T7 promoter is widely practiced in the art by the ordinarily skilled practitioner and ample guidance regarding the use of such promoters is available in the literature of the art.

The expression vector preferably comprises appropriate selectable marker sequences enabling cultures of the transformed or transfected host cells to be propagated without loss of capacity to express the soluble fusion protein. The expression vector preferably further comprises an origin of replication enabling propagation of the expression vector in the host cells. As necessary, the expression vector may comprise sequences enabling it to function as a shuttle vector which can propagate both in $E.$ $coli$ as well as in eukaryotic cells. It will be appreciated that other than containing the necessary elements for the expression of the soluble fusion protein, the expression vector can further comprise sequences engineered to optimize stability, production, purification, yield or activity of the expressed soluble fusion protein. Preferably, the codon usage of a recombinant polynucleotide/vector of the present invention should be appropriate to the host cell, for example to enable expression of the fusion protein in the host cell. It will be further appreciated that the codon usage may be selected so as to optimize expression of the fusion protein in the host cell.

One of ordinary skill in the art will possess the necessary expertise to obtain and utilize a suitable expression vector for producing a soluble fusion protein of the present invention, depending on the application and purpose. Relevant general guidance relating to obtaining and utilizing expression vectors which can be used to transform or transfect host cells so as to enable these to express a recombinant polypeptide is provided hereinbelow. Most preferably, obtaining and utilizing an expression vector of the present invention is performed according to the guidelines provided in Example 1 of the Examples section, below. As is described and illustrated in Example 1 of the Examples section which follows, a soluble fusion protein of the present invention can be suitably expressed by a host cell of the present invention which is transformed with an expression vector of the present invention.

Thus, the present invention provides an expression vector which comprises a recombinant polynucleotide of the present invention, and which further comprises at least one expression control sequence which is operatively linked to the recombinant polynucleotide, and is capable of controlling expression of the recombinant polynucleotide in a host cell of the present invention to thereby produce a soluble fusion protein of the present invention.

Thus, the present invention further provides a host cell transfected or transformed with the recombinant polynucleotide and/or expression vector.

The expression vector may be obtained in any of various ways routinely practiced by the ordinarily skilled artisan, depending on the application and purpose.

The expression vector is preferably assembled by cloning the heterologous polypeptide-encoding polynucleotide into a cloning vector which comprises a cloning site and the carrier polypeptide-encoding polynucleotides. The cloning site is designed and the carrier polypeptide-encoding polynucleotides are positioned so as to enable cloning of the heterologous polypeptide-encoding polynucleotide in frame with respect to the carrier polypeptide-encoding polynucleotides in such a way as to form the recombinant polynucleotide encoding the soluble fusion protein.

The cloning site is preferably a multiple cloning site (MCS), also termed a "polylinker" in the art. The cloning site should provide restriction sites which are complementary to terminal restriction sites of the heterologous polypeptide-encoding polynucleotide so as to enable its ligation into the cloning vector in the correct orientation.

Any of various commercially available vectors may provide a vector backbone from which to assemble the cloning vector. The vector backbone invention preferably provides necessary accessory sequences, such as a suitable origin of replication, promoter, selection marker and detectable moiety. Preferably, the vector backbone used to assemble the cloning vector is pET28-a(+).

General relevant guidance relating to obtaining and utilizing cloning vectors for producing expression vectors which can be used to transform/transfect host cells so as to enable these to express recombinant polypeptides, such as soluble fusion proteins of the present invention, is provided hereinbelow. Most preferably, the cloning vector is obtained and utilized according to the guidelines provided in Example 1 of the Examples section which follows. As is described and illustrated in Example 1 of the Examples section which follows, a cloning vector of the present invention can be used to assemble an expression vector of the present invention.

Thus, the present invention provides a cloning vector which comprises a cloning site and one or more carrier polypeptide-encoding polynucleotides of the present invention, where the cloning site is designed and the carrier polypeptide-encoding polynucleotides are positioned, so as to enable cloning of a heterologous polypeptide-encoding polynucleotide of the present invention in frame with respect to the carrier polypeptide-encoding polynucleotides, so as to form a polynucleotide encoding a soluble fusion protein of the present invention.

It will be appreciated that a cloning vector of the present invention may be packaged in a kit. The kit can be used, for example, to facilitate storage, distribution and/or commercialization of the cloning vector, to facilitate production of an expression vector of the present invention, and optionally to further facilitate generation of transformed/transfected host cells of the present invention. The kit will preferably be identified in print in or on the packaging as being for producing an expression vector of the present invention, and may optionally comprise any of various accessory agents, such as any of those described herein, for facilitating production of the expression vector, and/or generation of the transformed/transfected host cells. Accessory agents for facilitating production of an expression vector of the present invention may include nucleic acid processing enzymes, such as restriction enzymes, DNA polymerases and DNA ligases and the like. Accessory agents for facilitating host cell transformation/transfection and expression of the expression vector may include host cells, transformation/transfection reagents, protein expression inducers, and the like. The cloning vector and accessory agents are preferably held in labeled containers individually and/or collectively, as appropriate. Suitable containers include microfuge tubes, bottles, vials, and the like, and may be formed from a variety of materials such as glass or plastic. The cloning vector and accessory agents are preferably held in dry form or as solutions or suspensions containing appropriate buffers, stabilizers and the like. The kit preferably comprises suitable instructions for the intended use thereof. One of ordinary skill in the art will possess the necessary expertise to produce and utilize a kit of the present invention.

Thus, the present invention provides a kit for producing an expression vector of the present invention.

It will be appreciated that a cloning vector of the present invention can be used to transform a host cell of the present invention.

Thus, the present invention provides a host cell transfected or transformed with the cloning vector.

Such a cell can be used to conveniently hold, propagate and distribute a cloning vector of the present invention.

Transformation of a host cell of the present invention with a vector of the present invention can be effected in any of various ways according to standard art methods, depending on the application and purpose. General relevant guidance relating to ways of transforming/transfecting host cells with recombinant polynucleotides/vectors, such as recombinant polynucleotides/vectors of the present invention is provided hereinbelow.

A host cell of the present invention which is transformed or transfected with a recombinant polynucleotide/expression vector of the present invention, may be cultured in any of various ways so as to produce a desired quantity of the soluble protein, depending on the application and purpose.

The host cells are preferably cultured for a duration of time, which is sufficient to produce a desired quantity of the soluble fusion protein. Preferably, the host cells are cultured at the lowest temperature possible at which they can be induced so as to express desired levels of the soluble fusion protein, so as to minimize degradation of the expressed fusion protein and/or sequestration thereof in inclusion bodies.

Most preferably, the host cells are cultured in-vitro according to the guidelines provided in Example 1 of the Examples section below so as to produce a desired quantity of the soluble fusion polypeptide.

One of ordinary skill in the art will possess the necessary expertise to culture the host cells under suitable conditions so as to produce a desired quantity of the soluble fusion protein. General relevant guidance relating to culturing transformed/transfected host cells so as to produce a recombinant polypeptide, such as a fusion protein of the present invention, is provided hereinbelow.

Following culturing thereof so as to express a desired amount of the soluble fusion protein, the produced soluble fusion protein may be isolated/purified from the cultured host cells in any of various ways, depending on the application and purpose.

Preferably, the soluble fusion protein is isolated/purified from the cultured host cells according to the guidelines provided in Example 1 of the Examples section which follows.

According to the teachings of the present invention, a soluble fusion protein of the present invention may be isolated/purified from cultured host cells by harvesting the membranal fraction thereof via centrifugation, and subjecting the membranal fraction to mild detergent treatment so as to achieve solubilization of the soluble fusion protein as a monomeric/monodispersed or dimeric solution thereof. It will be appreciated that a soluble fusion protein of the present invention which occurs naturally as a homomultimer of a given valency may thereby be solubilized as a multimer of such valency. Alternately, the soluble fusion protein may be directly recovered from a soluble fraction of the cultured host cells. Detergent solubilization of the membrane-associated soluble fusion protein may be achieved using any of various detergents. Preferred detergents and concentrations thereof for such purpose are 2 percent Fos-Choline-16, and 2 percent Cyclofos-7. Following detergent solubilization, the soluble fusion protein may be purified by passage through a DEAE anion exchange column, followed by affinity column purification. Where the soluble fusion protein comprises a His-tag, the affinity column is a nickel-based affinity column, such as a nickel-NTA (Ni-NTA) affinity column. Optionally, the affinity column-purified soluble fusion protein may be further purified via liquid chromatography, preferably via fast protein liquid chromatography (FPLC).

An exemplary method of purifying the fusion proteins of the present invention is summarized in the flowchart presented in FIG. 23.

As is described in Example 1 of the Examples section which follows, soluble fusion proteins of the present invention may be isolated/purified to a very high degree according to the aforementioned isolation/purification procedure. General relevant guidance for isolating/purifying recombinant polypeptides, such as soluble fusion proteins of the present invention, from host cells from which these are expressed is provided hereinbelow.

Ample general guidance regarding production of soluble fusion proteins in host cells is provided in the literature of the art and may easily be adapted by the ordinarily skilled artisan for practicing embodiments of the present invention (refer, for example, to: Begum, R. R. et al., 2000. J. Chromatogr. B Biomed. Sci. Appl. 737:119-30; Davis, G. D. et al., 1999. Biotechnol. Bioeng. 65: 382-388; Kapust, R. B., Waugh, D. S., 1999. Protein Sci. 8:1668-1674; and U.S. Pat. Nos. 6,207,420 and 5,989,868).

The following provides general guidance relating to production of recombinant polypeptides, such as soluble fusion proteins of the present invention, by host cells such as those of the present invention. The following details are provided by way of exemplary information on recombinant polypeptide production in general, the adaptation of which for practicing embodiments of the present invention will be evident to one of ordinary skill in the art.

Generally, a recombinant nucleic acid sequence may be replicated in a host cell transfected/transformed using a suitable vector which comprises the nucleic acid sequence. A recombinant nucleic acid sequence may be expressed by a host cells which is transformed/transfected with an expression vector. Different types of vectors which can be used to replicate/express a recombinant nucleic acid sequence include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1994, infra). Expression vectors can contain a variety of "expression control sequences," which refer to nucleic acid sequences necessary for the transcription and possibly translation of an operably linked coding nucleic acid sequence in a particular host cell. In addition to control sequences that govern transcription/translation, vectors may contain nucleic acid sequences that serve other functions, as described below.

A "promoter" is a control sequence that is a region of a nucleic acid sequence at which initiation and rate of transcription are controlled. It may contain genetic elements at which regulatory proteins and molecules may bind such as RNA polymerase and other transcription factors. In order to be operatively linked to a nucleic acid sequence so as to control its transcriptional initiation and/or expression, a promoter should be in a correct functional location and/or orientation in relation to the nucleic acid sequence. In eukaryotic host cells a promoter may in certain cases be used in conjunction with an "enhancer," which refers to a cis-acting regulatory sequence involved in the transcriptional activation of a nucleic acid sequence.

A promoter may be cognate/"endogenous" to a gene or sequence, as may be obtained by isolating the natural 5' non-coding sequences located upstream of the coding segment. Similarly, an enhancer may be one naturally associated with a nucleic acid sequence, located either downstream or upstream of that sequence. Alternatively, certain advantages will be gained by positioning the coding nucleic acid segment under the control of a heterologous promoter/enhancer, i.e. one that is not normally associated with a nucleic acid sequence in its natural environment. Heterologous promoters or enhancers may be derived from genetic sequences from any suitable prokaryotic, viral, or eukaryotic cell types, and may be produced using recombinant cloning and/or nucleic acid amplification technology, including via PCR (see U.S. Pat. Nos. 4,683,202, 5,928,906). Where applicable, control sequences that direct transcription and/or expression of sequences within non-nuclear organelles such as mitochondria, chloroplasts, and the like, can be employed as well.

It will be generally desirable to employ a promoter and/or enhancer that effectively directs the expression of a recombinant nucleic acid sequence in the host cell type chosen for expression. Those of skill in the art of molecular biology generally know the use of promoters, enhancers, and cell type combinations for recombinant polypeptide expression (for example, see Sambrook et al., 1989, infra). The control sequences employed may be constitutive, tissue-specific, inducible, and/or useful under the appropriate conditions to direct high level expression of a recombinant nucleic acid sequence, such as is advantageous in the large-scale production of recombinant polypeptides.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. The initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In eukaryotic host cells, internal ribosome entry sites (IRES) elements may be used to create multigene, or polycistronic, messages. IRES elements are able to bypass the ribosome scanning model of 5' methylated Cap dependent translation and begin translation at internal sites (Pelletier and Sonenberg, 1988. Nature, 334:320-325). IRES elements from two members of the picornavirus family (polio and encephalomyocarditis) have been described (Pelletier and Sonenberg, 1988. Nature, 334:320-325, 1988), as well an IRES from a mammalian message (Macejak and Sarnow, 1991. Nature, 353:90-94, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819).

Vectors can include a multiple cloning site (MCS), which is a nucleic acid region that contains multiple restriction enzyme sites, any of which can be used in conjunction with standard recombinant technology to cleave the vector. (see Carbonelli et al., 1999. FEMS Microbiol Lett. 177:75-82; Levenson et al., 1998. Human Gene Therapy, 9:1233-1236; and Cocea, 1997. Biotechniques, 23:814-816). Restriction enzyme digestion involves catalytic cleavage of a nucleic acid molecule with an enzyme that functions only at specific restriction sites defined according to their nucleic acid sequences. Restriction sites of cloning sites are generally 6 nucleotides in length and occur only once within a vector. Frequently, a vector is linearized or fragmented using a restriction enzyme that cuts within the MCS to enable exogenous nucleic acid sequences to be ligated to the vector. Ligation is a process of formation of phosphodiester bonds between any two nucleic acid fragments having complementary ends capable of forming a double-stranded nucleic acid sequence. Techniques involving restriction enzymes and ligation reactions are well known to those of skill in the art of recombinant technology.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Depending on the application and purpose, host cells which contain a nucleic acid construct may be identified in vitro or in vivo by including a marker in the expression vector. Such markers confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Numerous prokaryotic and eukaryotic cells are available for use as a host cell, and can generally be obtained through the American Type Culture Collection (ATCC), which is an organization that serves as an archive for living cultures and genetic materials (www.atcc.org).

Host cells may be derived from gram negative or gram positive prokaryotic cells. An appropriate host cell can be determined by one of skill in the art based on the vector backbone and the desired result. A plasmid or cosmid, for example, can be introduced into a prokaryotic host cell for replication of many vectors. Bacterial cells used as host cells for vector replication and/or expression include DH5alpha, JM109, and KC8, as well as a number of commercially available bacterial hosts such as Sure Competent Cells and Solopack Gold Cells (Stratagene, La Jolla). Alternatively, bacterial cells such as E. coli LE392 could be used as host cells for phage viruses.

Examples of eukaryotic host cells for replication and/or expression of a vector include C. elegans, HeLa, NIH3T3, Jurkat, 293, COS, CHO, yeast, nematodes, insect cells, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides.

Examples of prokaryotic host cells which can be used for expression of recombinant polypeptides are E. coli strain RR1, E. coli LE392, E. coli B, E. coli X 1776 (ATCC No. 31537) as well as E. coli W3 110 (F-, lambda-, prototrophic, ATCC No. 273325); bacilli such as Bacillus subtilis; and other enterobacteriaceae such as Salmonella typhimurium, Serratia marcescens, and various Pseudomonas species. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is often transformed using derivatives of pBR322, a plasmid derived from an E. coli species pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM-11 may be utilized in making a recombinant phage vector which can be used to transform host cells, such as E. coli LE392.

Further useful E. coli vectors include pIN vectors (Inouye et al., 1985. Nucl. Acids Res. 13:3101-3109); and pGEX vectors, for use in generating glutathione S-transferase (GST) soluble fusion proteins for later purification and separation or cleavage. Other suitable fusion proteins are those with beta-galactosidase, ubiquitin, and the like.

Promoters that are commonly used to control expression of recombinant nucleic acid sequences in microbial host cells include the beta-lactamase (penicillinase), lactose and tryptophan (trp) promoter systems, and various other promoters. Details concerning their nucleotide sequences have been published, enabling those of skill in the art to ligate them functionally with plasmid vectors.

Both cDNA and genomic sequences are suitable for eukaryotic expression, as the host cell will generally process the genomic transcripts to yield functional mRNA for translation into protein. The use of cDNA is generally preferred for recombinant polypeptide expression since cDNA may be up to an order of magnitude shorter than corresponding genomic sequences.

Bacterial host cells, such as E. coli, transformed with an expression vector can be grown in any of a number of suitable media, for example, LB. The expression system may be selected so as to enable induction of the recombinant polypeptide by addition of an inducer to culture medium or by increasing incubation temperature. After culturing the host cells for a further period, generally of between 2 and 24 hours, the cells are collected by centrifugation and washed to remove residual medium. Following culturing host cells are lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. If the recombinant polypeptide is expressed in the inclusion bodies, as is the case in many instances, these can be washed in any of several solutions to remove some of the contaminating host proteins, then solubilized in solutions containing mild detergents, or alternately high concentrations of urea (e.g. 8M) or chaotropic agents such as guanidine hydrochloride in the presence of reducing agents, such as beta-mercaptoethanol or DTT (dithiothreitol). Under some circumstances, it may be advantageous to incubate the recombinant polypeptide for several hours under conditions suitable for it to undergo a refolding process into a conformation which more closely resembles native state. Such conditions generally include low protein concentrations, less than 500 mg/ml, low levels of reducing agent, concentrations of urea less than 2 M and often the presence of reagents such as a mixture of reduced and oxidized glutathione which facilitate the interchange of disulfide bonds within the recombinant polypeptide molecule. Recombinant polypeptide recovery can be monitored, for example, by SDS-PAGE, or with antibodies specific for the native molecule (which can be obtained from animals vaccinated with the native molecule or smaller quantities of recombinant polypeptide). Following refolding, the polypeptide can then be purified further and separated from the refolding mixture by chromatography on any of several supports including ion exchange resins, gel permeation resins, affinity columns, etc.

Thus, the present invention provides novel carrier polypeptides which can be fused to any one of an optimally broad range of heterologous polypeptides which are normally insoluble and/or suboptimally expressed when expressed in a cell, such as E. coli, so as to form a fusion protein which can be expressed by a host cell in optimal quantities, and which is optimally soluble, purifiable and stable under crystallization conditions. The carrier polypeptides are of optimally low molecular weight relative to the prior art, the heterologous polypeptide is of optimally high molecular weight relative to the prior art, and the ratio of the molecular weight of the carrier polypeptides to that of the heterologous polypeptide is optimally low by a large factor relative to the prior art. As such the present invention can be used to produce soluble fusion proteins which comprise a heterologous polypeptide whose structural conformation is minimally affected by steric and electrostatic effects of the carrier polypeptides.

By virtue of routinely enabling large-scale production of highly purified polypeptides, such as membrane proteins, which are insoluble and/or suboptimally expressed when expressed by a cell, which have an optimal structural conformation, and which are optimally stable under crystallization conditions, the present invention routinely enables crystallization of membrane proteins having an optimally broad range of sizes and types. As such, the present invention routinely enables, via X-ray crystallography, computationally assisted design/identification of optimally effective and specific drugs, such as inhibitory ligands, which target membrane proteins which are involved in disease pathogenesis, such proteins accounting for fully 70 percent of all drug targets while accounting for a negligible fraction of proteins whose high resolution 3D structures have been solved. As described in the Examples section which follows the human GABA neurotransmitter transporters GAT1, GAT2, GAT3 and GAT4 may be fused to carrier polypeptides of the present invention so as to form soluble proteins of the present invention. Since pharmacological regulation of neurotransmitter transport is widely employed in the treatment of various neurological diseases characterized by abnormal neurotransmitter transport, soluble fusion proteins of the present invention which comprise such neurotransmitter transporters can be used to design/identify drugs for treating such diseases. Similarly, soluble fusion proteins of the present invention which comprise the human glucose transporter GLUT4 can be generated as described in Example 1 of the Examples section which follows. Since pharmacological regulation of glucose transport is widely employed in the treatment of various diseases involving abnormal glucose transport, soluble fusion proteins of the present invention which comprise such glucose transporters can be used to design/identify drugs for treating such diseases.

By virtue of routinely enabling large-scale production of highly purified polypeptides, such as membrane proteins, which are insoluble and/or suboptimally expressed when expressed by a cell, and which have an optimal structural conformation, the present invention further enables production of drugs, diagnostic agents and research reagents whose active agents may be selected from an optimally broad range of membrane protein types having an optimally broad range of molecular weights.

It will be further appreciated that that by virtue of comprising a heterologous polypeptide of the present invention in a minimally distorted structural conformation, a fusion protein of the present invention can be used as an immunogen capable of stimulating production of antibodies having optimally high affinity for an optimally broad range of epitopes of the heterologous protein. This capacity confers upon the soluble fusion proteins of the present invention tremendous medical utility since antibodies against insoluble proteins of the present invention, such as growth factor receptors, are standard therapeutic agents used in the treatment of major diseases, as exemplified by the use of the anti-HER2 monoclonal antibody Herceptin for treatment of mammary carcinoma.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Optimal carrier polypeptides for generation of soluble fusion proteins Introduction: No satisfactory/optimal and generally applicable methods are available for producing heterologous polypeptides, such as membrane proteins, which are normally insoluble and/or suboptimally expressed when expressed in a cell, such that these are produced is in a soluble/purifiable form and quantity enabling their high-grade crystallization. Methods for achieving such production are extremely desirable for numerous applications, in particular since high-grade crystals of such polypeptides, by virtue of being amenable to high resolution 3D X-ray crystallography, have the unique ability to enable the computationally assisted design/identification of optimal drugs for treating any of the vast range of diseases whose pathogenesis is associated with functionality of such polypeptides. A potentially optimal strategy for achieving production of such polypeptides in a soluble form and quantity enabling their high-grade crystallization involves expression in host cells of fusion proteins which comprises such polypeptides translationally fused to soluble/hydrophilic carrier polypeptides. While such approaches have been attempted in the prior art, these have significant disadvantages, including being limited to production of fusion proteins which comprise a carrier polypeptide having a molecular weight which is at least approximately three-quarters that of the heterologous polypeptide to which it is fused. Such heterologous polypeptides are thereby susceptible to strong conformational distortion induced by relatively large electrostatic and steric effects of the relatively large carrier polypeptide. While reducing the present invention to practice, novel fusion protein configurations employing novel carrier polypeptides which overcome the limitations of the prior art were unexpectedly uncovered, as described below.

Materials and Methods:

A summary of the work scheme employed in the presently disclosed experiments is shown in FIG. 1A.

Cloning of expression vectors: Inducible bacterial expression vectors were generated encoding fusion proteins which comprise a selected membrane protein translationally fused at its N-terminus and/or C-terminus to one or two alpha-helical hydrophilic carrier polypeptides, and which has His-tags at both termini. The carrier polypeptides employed were: (i) amino acid residues 8 to 98 of $E.$ $coli$ YaiN [YaiN(8-98); GenBank Accession No. NP_286100; SEQ ID NO: 1], having a molecular weight of 9.9 kilodaltons and a length of 91 amino acid residues; and (ii) amino acid residues 1-121 of $E.$ $coli$ YbeL [YbeL(1-121); GenBank Accession No. NP_286369; SEQ ID NO: 2], having a molecular weight of 13.2 kilodaltons. The six membrane proteins employed were: (a) MntH, an $E.$ $coli$ divalent metal ion transporter belonging to the NRAMP family of eukaryotic divalent metal ion transporters, characterized as pH-dependent secondary transporters (Courville, P. et al., 2004. $J.$ $Biol.$ $Chem.$ 279:3318-3326; Makui, H et al., 2000. $Mol.$ $Microbiol.$ 35:1065-1078); (b) GAT1, GAT2, GAT3, and GAT4, $Mus$ $musculus$ GABA neurotransmitter transporters (Liu, Q.R. et al., 1993. J Biol Chem. 268:2106-2112); and (c) GLUT 4, a human glucose transporter involved in diabetes (Randhawa, VK et al., 2004. $Mol$ $Biol$ $Cell.$ 15:5565-5573). DNAs encoding carrier polypeptides were cloned into the inducible expression vector pET28a+ (FIG. 1B) at the polylinker cloning site to generate cloning vectors allowing generation of constructs for expression of the 8 possible fusion protein configurations (shown in FIG. 1C and Table 1). A schematic diagram of a portion of a representative cloning vector for generation of expression vectors encoding a fusion protein having the configuration N'-YaiN(8-98)-[heterologous polypeptide]-YbeL (1-121)-C' is shown in FIG. 1D. Fusion protein expression vectors were then generated by ligating DNA sequences encoding the insoluble membrane proteins into the polylinkers of the cloning vectors.

A TEV protease site was also cloned into the 8 vectors combinations so that subsequent removal of the soluble carrier peptides of the present invention could be effected (see FIG. 25A).

PCR: PCR amplifications were performed using 30 cycles of: 94 degrees centigrade for 30 seconds, 54 degrees centigrade for 30 seconds and 72 degrees centigrade for 30 seconds. All ligations were performed at room temperature for 1 hour. The pGEM T-easy constructs were transformed into competent DH10B $E.$ $coli$ cells, and the pET28a(+) constructs were transformed into $E.$ $coli$ C43 (Miroux, B. and Walker, J. E., 1996. J Mol Biol. 260:289-298) competent cells. The primers employed are described in Table 2.

TABLE 1

Assembly of cloning vectors enabling generation of vectors for expression of different His-tag-tagged fusion protein configurations.

| Cloning vector | Recombinant polypeptide configuration* | Cloning scheme |
| --- | --- | --- |
| alpha-pET28a(+) | alpha-HPP | The cloning vector for generation of constructs for expression of fusion proteins with YaiN(8-98) at the N-terminus was generated as follows: YaiN(8-98) was amplified by PCR, using the primer N4804 containing restriction site NdeI, and the primer C4805 containing restriction site BamHI, and cloned into pGEM T-easy plasmid. The segment was cloned into pET28a(+) plasmid, which contained a 6-His tag at the N-terminus and the C-terminus. The resulting cloning vector contained YaiN(8-98) with the two restriction sites conserved. |
| pET28a(+)-alpha | HPP-alpha | YaiN(8-98) was amplified by PCR, using the primer N5200A containing restriction site NotI and XhoI, and the primer C5201A containing restriction site SalI, and cloned into pGEM T-easy plasmid. The segment was cloned into pET28a(+) plasmid, which contained a 6-His tag at the N-terminus and the C-terminus. The resulting cloning vector contained YaiN(8-98) with the two restriction sites conserved The NotI and XhoI (SalI is compatible with the XhoI site of pET28a(+), and is canceled). |
| beta-pET28a(+) | beta-HPP | The cloning vector for generation of constructs for expression of fusion proteins with YbeL(1-121) at the N-terminus was generated as follows: YbeL(1-121) was amplified by PCR, using the primer N4954 containing restriction site NdeI, and the primer C4955 containing restriction site BamHI, and cloned into pGEM T-easy plasmid. The segment was cloned into pET28a(+) plasmid, which contained a 6-His tag at the N-terminus and the C-terminus. The resulting cloning vector contained YbeL(1-121) with the two restriction sites conserved. |
| pET28a(+)-beta | HPP-beta | The cloning vector for generation of constructs for expression of fusion proteins with YbeL(1-121) at the C-terminus was generated as follows: YbeL(1-121) was amplified by PCR, using the primer N4806 containing restriction site NotI and XhoI, and the primer C4807A containing restriction site SalI, and cloned into pGEM T-easy plasmid. The segment was cloned into pET28a(+) plasmid, which contained a 6-His tag at the N-terminus and the C-terminus. The resulting cloning vector contains YbeL(1-121) with NotI and XhoI. |
| alpha-pET28a(+)-beta | alpha-HPP-beta | The cloning vector for generation of constructs for expression of fusion proteins with YaiN(8-98) at the N-terminus and YbeL(1-121) at the C-terminus was generated as follows: pET28a(+) plasmid containing YaiN(8-98), prepared as described in the cloning scheme of cloning vector alpha-pET28a(+), was digested with NdeI and BamHI. The resulting insert was ligated into the pET28a(+) plasmid containing YbeL(1-121), described in the cloning scheme of cloning vector pET28a(+)-beta, which was digested with the same restriction enzymes-NdeI and BamHI. The resulting cloning vector contained YbeL(1-121) and YaiN(8-98) with the restriction sites conserved as described in cloning scheme of alpha-pET28a(+) and pET28a(+)-beta. |
| alpha-pET28a(+)-alpha | alpha-HPP-alpha | The cloning vector for generation of constructs for expression of fusion proteins with YaiN(8-98) at the N-terminus and YaiN(8-98) at the C-terminus was generated as follows: pET28a(+) plasmid containing YaiN(8-98), prepared as described in the cloning scheme of cloning vector alpha-pET28a(+), was digested with NdeI and BamHI. The resulting insert was ligated into the pET28a(+) plasmid containing YaiN(8-98), as described in the cloning scheme of construct pET28a(+)-alpha, which was digested with the same restriction enzymes-NdeI and BamHI. The resulting cloning vector contained YaiN(8-98) with the restriction sites conserved as described in cloning scheme of cloning vectors alpha-pET28a(+) and pET28a(+)-alpha. |
| beta-pET28a(+)-alpha | beta-HPP-alpha | The cloning vector for generation of constructs for expression of fusion proteins with YbeL(1-121) at the N-terminus and YaiN(8-98) at the C-terminus was generated as follows: YaiN(8-98) was amplified by PCR as described in the cloning scheme of pET28a(+)-alpha and cloned into pGEM T-easy plasmid. The segment was cloned into the pET28a(+) plasmid containing YbeL(1-121) described in the cloning scheme of construct beta-pET28a(+), which was digested with NotI and XhoI. The resulting cloning vector contained YbeL(1-121) |

TABLE 1-continued

Assembly of cloning vectors enabling generation of vectors for expression of different His-tag-tagged fusion protein configurations.

| Cloning vector | Recombinant polypeptide configuration* | Cloning scheme |
|---|---|---|
| | | and YaiN(8-98) with the restriction sites conserved as described in the cloning scheme of cloning vectors pET28a(+)-alpha and beta-pET28a(+). |
| beta-pET28a(+)-beta | beta-HPP-beta | The cloning vector for generation of constructs for expression of fusion proteins with YbeL(1-121) at the N-terminus and YbeL(1-121) at the C-terminus was generated as follows: pET28a(+) plasmid containing YbeL(1-121), prepared as described in the cloning scheme of cloning vector beta-pET28a(+), was digested with NdeI and BamHI. The resulting insert was ligated into the pET28a(+) plasmid containing YbeL(1-121), described in the cloning scheme of pET28a(+)-beta, which was digested with the same restriction enzymes-NdeI and BamHI. The resulting cloning vector contained YbeL(1-121) with the restriction sites conserved as described in the cloning scheme of cloning vectors beta-pET28a(+) and pET28a(+)-beta. |

*alpha, YaiN(8-98); beta, YbeL(1-121); HPP, heterologous polypeptide.

TABLE 2

PCR primer sequences.

| Primer specificity | Primer No. | Restriction site(s) | Primer nucleotide sequence |
|---|---|---|---|
| alpha-N' | N4804 | NdeI | TATGGATCCTTTAAGATAGGC ACGAACCAGTTC (SEQ ID NO: 3) |
| | C4805 | BamHI | TATCATATGAGGTGCGAAATG CCCAGTACTC (SEQ ID NO: 4) |
| alpha-C' | N5200A | NotI, XhoI | TGCGGCCGCCTCGAGATGAGG TGCGAAATGCCCAGTAC (SEQ ID NO: 5) |
| | C5201A | SalI | TATGTCGACTTTAAGATAGGC ACGAACCAGTTC (SEQ ID NO: 6) |
| beta-N' | N4954 | NdeI | TATCATATGAACAAGGTTGCT CAATATTAC (SEQ ID NO: 7) |
| | C4955 | BamHI | TATGGATCCCCCGACCACTTC TCCGCTGTGAT (SEQ ID NO: 8) |
| beta-C' | N4806 | NotI, XhoI | TGCGGCCGCACTCGAGATGAA CAAGGTTGCTCAATATTACCG T (SEQ ID NO: 9) |
| | C4807A | SalI | TATGTCGACCCGACCACTTCT CCGCTGTGAT (SEQ ID NO: 10) |

Host cells: *E. coli* strain C43 (DE3) was used [F⁻ ompT hsdS$_B$(r$_B^-$ m$_B^-$)gal dcm]. This is a mutant host derivative from the *E. coli* strain BL21 having the following characterized by its lack of the Ion-protease, ompT membrane protease and dcm methylase; its being a mutant at the EcoB restriction enzyme site and at the beta-galactosidase gene; and can be grown at low temperature (less than 20 degrees centigrade).

Fusion protein production: *E. coli* bacteria were transformed with expression vectors, and were selected and grown in Terrific Broth medium containing kanamycin (20 micrograms per milliliter) at 37 degrees centigrade until cultures reached an OD$_{600}$ of 0.6-0.8. Fusion protein expression was induced by addition of 1 millimolar IPTG to the cultures and incubation at 18 degrees centigrade for 16 hours. The induced cell cultures were harvested and lysed in sucrose buffer (0.3 molar sucrose, 20 millimolar MOPS, pH-7), containing 2 millimolar PMSF to inhibit proteases. Cells were crushed using a French-press, centrifuged at 45,000 rpm at 4 degrees centigrade for 1 hour, and the membrane-containing pellet was isolated and resuspended in sucrose buffer. Protein concentration was determined using Bradford reagent, and all samples were diluted to the lowest concentration or at a concentration of 10 milligrams per milliliter according to the specific experiment. The harvested proteins were solubilized in 2 percent detergent (Fos-choline-16 or Cyclofos-7), and the fusion proteins were purified therefrom by passage through a DEAE anion exchange column, followed by nickel-NTA (Ni-NTA) affinity column purification.

Removal of the soluble carrier polypeptides was effected by digestion with TEV protease or trypsin for the indicated times at 4° C. followed by size exclusion chromatography.

Crystallization assays: For crystallization assays, Ni-NTA affinity column-purified fusion proteins were concentrated using 10 percent PEG-6000 and resuspended in crystallization buffer (2 millimolar Tris-pH 7.5, 0.02 percent detergent). The concentrated fusion proteins were purified by FPLC monoQ anion exchange chromatography, concentrated using 10 percent PEG-6000 and resuspended in crystallization buffer to reach concentration of 10 milligrams per milliliter. Crystallization experiments were performed at 4-18 degrees centigrade by hanging-drop vapor diffusion, sitting-drop vapor diffusion and microbatch-drops, by mixing equal volumes of protein and reservoir solution.

Solubility assays: The oligomerization state of purified fusion proteins was determined by analysis of fractions obtained from sucrose density gradient centrifugation. A sample of concentrated fusion protein was loaded on a 7 to 60 percent sucrose gradient containing 20 millimolar Tris-pH 7.5 and 0.02 percent detergent. The gradient was centrifuged in an SW40 rotor at 37,000 rpm for 16 hours, and fractions were collected from the bottom of the tube.

Western blot analysis: Western blot analysis of expressed fusion protein was performed using 12.5 percent SDS-PAGE, mouse anti-His-tag primary antibody and anti-mouse Ig secondary antibody. Results were quantified using IMAGE-MASTER ID software. Fusion proteins were isolated via capture of their His-tags by passage through a Ni-NTA affinity column.

Experimental Results:

E. coli host bacteria were transformed with inducible expression vectors encoding various configurations of His-tag-tagged fusion proteins which comprise the transmembrane protein MntH, GAT1, GAT2, GAT3, GAT4, GLUT 4, Kvlm, HMGR and VMAT fused at either or both termini respectively to one or two of the carrier polypeptides corresponding to amino acid residues 8-98 of E. coli YaiN [YaiN (8-98); GenBank Accession No. NP_286100; SEQ ID NO: 1], and to amino acids 1-121 of E. coli YbeL [YbeL(1-121); GenBank Accession No. NP_286369]; SEQ ID NO: 2).

These carrier polypeptides are highly hydrophilic as shown by Kyle-Doolittle hydrophobicity analysis (FIGS. 1E-F, respectively, determined using the plot-generating software at http://www.expasy.org/tools/pscale/Hphob.Doolittle.html) and are characterized by negatively charged hydrophilic alpha-helices separated by polypeptide loops (FIGS. 1G-H, respectively), as determined according to the "SUB_sec" values generated when analyzing the amino acid sequences using PREDICTPROTEIN software (http://cubic.bioc.columbia.edu/predictprotein/; Rost B. et al., 1996. *Protein Sci.* 5:1704-18). The transformed bacteria were tested for fusion protein expression capacity and purified (FIGS. 2-27), and for each of the membrane proteins tested, at least one of the presently disclosed novel fusion proteins was expressed at high level (FIGS. 17A-H) which could be produced and solubilized as a monomer or dimer from the E. coli membrane at high levels by relatively mild detergents (FIGS. 12A-B and 17A-H) at very low detergent concentrations (0.02 to 0.1 percent). For example, as shown in FIGS. 13 and 23C the expressed fusion protein beta-GAT1-beta was mono-dispersed and exhibited a migration pattern in the sucrose gradient corresponding to a monomer or dimer. Similar experiments were performed with fusion proteins containing the other expressed membrane proteins with essentially the same results (FIGS. 22A-G). All of the membrane proteins could be produced as a fusion protein purifiable via Ni-NTA affinity column chromatography. The yields of the purified proteins were between 1.3-1.7 milligrams (mammalian) to 48 milligrams (bacterial) per liter culture. Nickel column-purified fusion proteins were amenable to further purification by fast protein liquid chromatography (FPLC, FIGS. 10B and 19A-H, FIGS. 20A-G and FIGS. 21A-H). Remarkably, highly purified fusion proteins comprising GAT-family membrane proteins, which are highly insoluble due to their containing 12 transmembrane helices (FIG. 14), could be obtained in monomeric form at very high concentrations (over 10 milligrams protein per milliliter), including GAT1 which has a molecular weight of 66 kilodaltons. Remarkably fusion protein alpha-GAT1 was found to be highly soluble and purifiable, being formed by fusion of GAT1 with the carrier polypeptide YaiN (8-98) having a very low molecular weight of 9.9 kilodaltons, being about 7-fold less than the molecular weight of 66 kilodaltons of GAT1 (FIGS. 7 and 17B). All of the membrane proteins could be expressed as fusion proteins which were amenable to detergent exchange for crystallization, and exhibited high stability and did not aggregate even after three months under crystallization solution conditions at temperatures ranging from 4 to 17 degrees centigrade (FIG. 15 and data not shown).

Analysis of the CD spectra of the purified fusion polypeptides of the present invention (FIGS. 24A-D) indicates that these overexpressed membrane proteins are stable, not in inclusion bodies and folded The soluble carrier polypeptides of the present invention could be removed following incubation in TEV protease as illustrated in FIG. 25B and FIG. 26 and by trypsin (FIGS. 27A-B).

Conclusion: The above-described experimental results provide a generally applicable method of expressing membrane proteins in bacteria in a soluble form and quantity enabling their high-grade crystallization. Such expression is presently enabled for the first time by translational fusion of the membrane proteins with hydrophilic alpha-helical carrier polypeptides which solubilize the membrane proteins, and which enable their high-level expression in recombinant host bacteria. The presently disclosed membrane protein production method overcomes various critical disadvantages of prior art carrier polypeptide-based methods. Namely, the prior art teaches production of fusion proteins which comprise carrier polypeptides which have a molecular weight which is at least approximately three-quarters that of the prior art heterologous polypeptide to which it is fused. The relatively large size of the prior art carrier polypeptides will tend to induce relatively large conformational distortion of the membrane protein's native conformation via relatively large electrostatic and steric effects. This is highly undesirable since this will prevent generation of fusion protein crystals capable of generating crystallographic data defining the native 3D atomic structure of membrane proteins with optimal accuracy. This is in sharp contrast to the presently described carrier polypeptides which have a molecular weight as low as 9.9 kilodaltons and which enable production/crystallization of membrane proteins having a molecular weight as high as 66 kilodaltons, i.e. about 7-fold larger than the carrier polypeptide. Thus, by virtue of generally enabling for the first time high-grade crystallization of membrane proteins, the presently disclosed methodology generally enables for the first time solution of the 3D atomic structure of such proteins, and hence generally enables for the first time the generally applicable computationally assisted design/identification of optimal drugs for treatment of diseases whose pathogenesis is associated with functionality of a heterologous polypeptide, such as membrane protein, which is normally insoluble and/or suboptimally expressed when expressed by a cell.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and sequences identified by their GenBank accession numbers mentioned in this specification are herein incorporated in their entirety by reference into the specification, to the same extent as if each individual publication, patent, or sequence identified by its GenBank accession number was specifically and individually indicated to be incorporated herein by reference. In addition, citation or identification of any reference in this application shall not be construed as an admission that such reference is available as prior art to the present invention.

What is claimed is:

1. A soluble fusion protein comprising at least one soluble polypeptide and a heterologous polypeptide being fused thereto, said heterologous polypeptide being normally insoluble and/or suboptimally expressed when expressed in an *Escherichia coli* (*E. coli*) cell,
    wherein said at least one soluble polypeptide has an amino acid sequence at least 65 percent similar to SEQ ID NO: 1, as determined using the Standard protein-protein BLAST [blastp] software of the NCBI.

2. The soluble fusion protein of claim 1, wherein said heterologous polypeptide is a membrane polypeptide.

3. The soluble fusion protein of claim 2, wherein said membrane polypeptide is selected from the group consisting of an ion transporter, a neurotransmitter transporter, a sugar transporter and an enzyme.

4. The soluble fusion protein of claim 2, wherein said membrane polypeptide is selected from the group consisting of MntH, Kvlm, GAT1, GAT2, GAT3, GAT4, VMAT and HMG-CoA reductase.

5. The soluble fusion protein of claim 1, wherein said at least one soluble polypeptide comprises at least 2 alpha-helical structures being separated therebetween by at least one polypeptide loop.

6. The soluble fusion protein of claim 1, wherein said at least one soluble polypeptide has a molecular weight which is at least 1.5 times lower than a molecular weight of said heterologous polypeptide.

7. The soluble fusion protein of claim 1, wherein said heterologous polypeptide has a molecular weight of at least 60 kilodaltons.

8. The soluble fusion protein of claim 1, wherein said at least one soluble polypeptide has a molecular weight of 11.5 kilodaltons or less.

9. The soluble fusion protein of claim 1, wherein said at least one soluble polypeptide is directly or indirectly fused to an amino terminus of said heterologous polypeptide.

10. The soluble fusion protein of claim 1, wherein said at least one soluble polypeptide is directly or indirectly fused to a carboxy terminus of said heterologous polypeptide.

11. The soluble fusion protein of claim 1, wherein said at least one soluble polypeptide comprises a first soluble polypeptide which is directly or indirectly fused to an amino terminus of said heterologous polypeptide, and further comprises a second soluble polypeptide which is directly or indirectly fused to a carboxy terminus of said heterologous polypeptide, wherein said second soluble polypeptide is identical or non-identical to said first soluble polypeptide.

12. A method of producing the soluble fusion protein of claim 1 comprising:
    culturing a *E. coli* cell being transfected or transformed with a recombinant polynucleotide encoding the soluble fusion protein of claim 1, said culturing being under conditions causing expression of said polynucleotide in said *E. coli* cell, and:
    optionally, isolating said soluble fusion protein of claim 1 from said *E. coli* cell following said culturing, thereby producing the soluble fusion protein of claim 1.

13. The method of claim 12, wherein said at least one soluble polypeptide comprises at least 2 alpha-helical structures being separated therebetween by at least one polypeptide loop.

14. The method of claim 12, wherein said at least one soluble polypeptide has a molecular weight which is at least 1.5 times lower than a molecular weight of said heterologous polypeptide.

15. The method of claim 12, wherein the heterologous polypeptide has a molecular weight of at least 60 kilodaltons.

16. The method of claim 12, wherein the heterologous polypeptide is a membrane polypeptide.

17. The method of claim 12, wherein said membrane polypeptide is selected from the group consisting of an ion transporter, a neurotransmitter transporter, a sugar transporter and an enzyme.

18. The method of claim 12, wherein said membrane polypeptide is selected from the group consisting fo MntH, Kvlm, GAT1, GAT2, GAT3, GAT4, VMAT and HMG-CoA reductase.

19. The method of claim 12, wherein said at least one soluble polypeptide has a molecular weight of 12 kilodaltons or less.

20. The method of claim 12, wherein said at least one soluble polypeptide is directly or indirectly fused to an amino terminus of the heterologous polypeptide.

21. The method of claim 12, wherein said at least one soluble polypeptide is directly or indirectly fused to a carboxy terminus of the heterologous polypeptide.

22. The method of claim 12, wherein said at least one soluble polypeptide comprises a first soluble polypeptide which is directly or indirectly fused to an amino terminus of the heterologous polypeptide, and further comprises a second soluble polypeptide which is directly or indirectly fused to a carboxy terminus of the heterologous polypeptide, wherein said second soluble polypeptide is identical or non-identical to said first soluble polypeptide.

23. A recombinant polynucleotide encoding a soluble fusion protein which comprises at least one soluble polypeptide and a heterologous polypeptide being fused thereto, wherein the heterologous polypeptide is normally insoluble and/or suboptimally expressed when expressed in an *E. coli* cell, the recombinant polynucleotide comprising:
    at least one first polynucleotide encoding the at least one soluble polypeptide; and
    a second polynucleotide encoding the heterologous polypeptide, said at least one first polynucleotide and said second polynucleotide being positioned in frame with respect to each other so as to encode the soluble fusion protein,
    wherein the at least one soluble polypeptide has an amino acid sequence at least 65 percent similar to SEQ ID NO: 1, as determined using the Standard protein-protein BLAST [blastp] software of the NCBI.

24. The recombinant polynucleotide of claim 23, wherein said heterologous polypeptide is a membrane polypeptide.

25. The recombinant polynucleotide of claim 24, wherein said membrane polypeptide is selected from the group consisting of an ion transporter, a neurotransmitter transporter, a sugar transporter and an enzyme.

26. The recombinant polynucleotide of claim 24, wherein said membrane polypeptide is selected from the group consisting of MntH, Kvlm, GAT1, GAT2, GAT3, GAT4, VMAT and HMG-CoA reductase.

27. The recombinant polynucleotide of claim 23, wherein said at least one soluble polypeptide comprises at least 2 alpha-helical structures being separated therebetween by at least one polypeptide loop.

28. The recombinant polynucleotide of claim 23, wherein said at least one soluble polypeptide has a molecular weight which is at least 1.5 times lower than a molecular weight of said heterologous polypeptide.

29. The recombinant polynucleotide of claim 23, wherein said heterologous polypeptide has a molecular weight of at least 60 kilodaltons.

30. The recombinant polynucleotide of claim 23, wherein said at least one soluble polypeptide has a molecular weight of 12 kilodaltons or less.

31. The recombinant polynucleotide of claim 23, wherein the at least one soluble polypeptide is directly or indirectly fused to an amino terminus of the heterologous polypeptide.

32. The recombinant polynucleotide of claim 23, wherein the at least one soluble polypeptide is directly or indirectly fused to a carboxy terminus of the heterologous polypeptide.

33. The recombinant polynucleotide of claim 23, wherein the at least one soluble polypeptide comprises a first soluble polypeptide which is directly or indirectly fused to an amino terminus of the heterologous polypeptide, and further comprises a second soluble polypeptide which is directly or indirectly fused to a carboxy terminus of the heterologous polypeptide, wherein said second soluble polypeptide is identical or non-identical to said first soluble polypeptide.

34. The recombinant polynucleotide of claim 23, further comprising at least one expression control sequence being operatively linked thereto and capable of controlling expression thereof in an *E. coli* cell.

35. The recombinant polynucleotide of claim 23, being transfected into an *E. coli* cell.

36. A cloning vector comprising a cloning site and at least one first polynucleotide, said at least one first polynucleotide encoding at least one soluble polypeptide, said cloning site being designed to enable cloning of a second polynucleotide encoding a heterologous polypeptide in frame with respect to said at least one first polynucleotide so as to form a recombinant polynucleotide encoding a fusion protein which comprises said at least one soluble polypeptide and said heterologous polypeptide being fused thereto, wherein said at least one soluble polypeptide has an amino acid sequence at least 65 percent similar to SEQ ID NO: 1, as determined using the Standard protein-protein BLAST [blastp] software of the NCBI.

37. The cloning vector of claim 36, wherein said at least one soluble polypeptide comprises at least 2 alpha-helical structures being separated therebetween by at least one polypeptide loop.

38. The cloning vector of claim 36, wherein said at least one soluble polypeptide has a molecular weight of 12 kilodaltons or less.

39. The cloning vector of claim 36, wherein said at least one soluble polypeptide is directly or indirectly fused to an amino terminus of said heterologous polypeptide.

40. The cloning vector of claim 36, wherein said at least one soluble polypeptide is directly or indirectly fused to a carboxy terminus of said heterologous polypeptide.

41. The cloning vector of claim 36, wherein said at least one soluble polypeptide comprises a first soluble polypeptide which is directly or indirectly fused to an amino terminus of said heterologous polypeptide, and further comprises a second soluble polypeptide which is directly or indirectly fused to a carboxy terminus of said heterologous polypeptide, wherein said second soluble polypeptide is identical or non-identical to said first soluble polypeptide.

42. The cloning vector of claim 36, wherein said heterologous polypeptide, is a membrane polypeptide.

43. The cloning vector of claim 36, wherein said membrane polypeptide is selected from the group consisting of an ion transporter, a neurotransmitter transporter, a sugar transporter and an enzyme.

44. The cloning vector of claim 36, wherein said membrane polypeptide is selected from the group consisting of MntH, Kvlm, GAT1, GAT2, GAT3, GAT4, VMAT and HMG-CoA reductase.

45. The cloning vector of claim 36, being transfected or transformed into an *E. coli* cell.

46. A kit for producing an expression vector, the expression vector being for expressing in a *E. coli* cell a soluble fusion protein which comprises a heterologous polypeptide, the heterologous polypeptide being insoluble and/or suboptimally expressed when expressed in a cell, the kit comprising the cloning vector of claim 36.

* * * * *

SEQUENCE LISTING

<160> NUMBER OF SEQ ID NOS: 10

<210> SEQ ID NO 1
<211> LENGTH: 91
<212> TYPE: PRT
<213> ORGANISM: Escherichia coli

<400> SEQUENCE: 1

Met Pro Ser Thr Pro Glu Glu Lys Lys Val Leu Thr Arg Val Arg
1               5                   10                  15

Arg Ile Arg Gly Gln Ile Asp Ala Leu Glu Arg Ser Leu Glu Gly Asp
            20                  25                  30

Ala Glu Cys Arg Ala Ile Leu Gln Gln Ile Ala Ala Val Arg Gly Ala
        35                  40                  45

Ala Asn Gly Leu Met Ala Glu Val Leu Glu Ser His Ile Arg Glu Thr
    50                  55                  60

Phe Asp Arg Asn Asp Cys Tyr Ser Arg Glu Val Ser Gln Ser Val Asp
65                  70                  75                  80

Asp Thr Ile Glu Leu Val Arg Ala Tyr Leu Lys
                85                  90

<210> SEQ ID NO 2
<211> LENGTH: 121
<212> TYPE: PRT
<213> ORGANISM: Escherichia coli

<400> SEQUENCE: 2

Met Asn Lys Val Ala Gln Tyr Tyr Arg Glu Leu Val Ala Ser Leu Ser
1               5                   10                  15

Glu Arg Leu Arg Asn Gly Glu Arg Asp Ile Asp Ala Leu Val Glu Gln
            20                  25                  30

Ala Arg Glu Arg Val Ile Lys Thr Gly Glu Leu Thr Arg Thr Glu Val
        35                  40                  45

Asp Glu Leu Thr Arg Ala Val Arg Arg Asp Leu Glu Glu Phe Ala Met
    50                  55                  60

Ser Tyr Glu Glu Ser Leu Lys Glu Glu Ser Asp Ser Val Phe Met Arg
65                  70                  75                  80

Val Ile Lys Glu Ser Leu Trp Gln Glu Leu Ala Asp Ile Thr Asp Lys
                85                  90                  95

Thr Gln Leu Glu Trp Arg Glu Val Phe Gln Asp Leu Asn His His Gly
            100                 105                 110

Val Tyr His Ser Gly Glu Val Val Gly
        115                 120

<210> SEQ ID NO 3
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 3
tatggatcct ttaagatagg cacgaaccag ttc                          33

<210> SEQ ID NO 4
<211> LENGTH: 31
<212> TYPE: DNA
<213> ORGANISM: Artificial sequence

```
<220> FEATURE:
<223> OTHER INFORMATION: Single strand DNA oligonucleotide

<400> SEQUENCE: 4
tatcatatga ggtgcgaaat gcccagtact c                              31

<210> SEQ ID NO 5
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 5
tgcggccgcc tcgagatgag gtgcgaaatg cccagtac                       38

<210> SEQ ID NO 6
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 6
tatgtcgact ttaagatagg cacgaaccag ttc                            33

<210> SEQ ID NO 7
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 7
tatcatatga acaaggttgc tcaatattac                                30

<210> SEQ ID NO 8
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 8
tatggatccc ccgaccactt ctccgctgtg at                             32

<210> SEQ ID NO 9
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 9
tgcggccgca ctcgagatga acaaggttgc tcaatattac cgt                 43

<210> SEQ ID NO 10
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 10
tatgtcgacc cgaccacttc tccgctgtga t                              31
```